US012667560B2

(12) United States Patent
Luo et al.

(10) Patent No.: US 12,667,560 B2
(45) Date of Patent: Jun. 30, 2026

(54) CO-ADMINISTRATION OF MIRDAMETINIB AND LIFIRAFENIB FOR USE IN TREATING CANCERS

(71) Applicants: BeiGene, Ltd., San Mateo, CA (US); SpringWorks Therapeutics, Inc., Stamford, CT (US)

(72) Inventors: Lusong Luo, San Mateo, CA (US); Zhiyu Tang, San Mateo, CA (US); Badreddin Edris, Stamford, CT (US); Todd Webster Shearer, Stamford, CT (US)

(73) Assignees: SPRINGWORKS THERAPEUTICS, INC., Stamford, CT (US); BEIGENE, LTD., San Mateo, CA (US)

( * ) Notice: Subject to any disclaimer, the term of this patent is extended or adjusted under 35 U.S.C. 154(b) by 469 days.

(21) Appl. No.: 17/995,002

(22) PCT Filed: Apr. 2, 2021

(86) PCT No.: PCT/US2021/025551

§ 371 (c)(1),
(2) Date: Sep. 29, 2022

(87) PCT Pub. No.: WO2021/202981

PCT Pub. Date: Oct. 7, 2021

(65) Prior Publication Data

US 2023/0128315 A1 Apr. 27, 2023

Related U.S. Application Data

(60) Provisional application No. 63/005,153, filed on Apr. 3, 2020.

(51) Int. Cl.

| | |
|---|---|
| ***A61K 31/4375*** | (2006.01) |
| ***A61K 9/48*** | (2006.01) |
| ***A61K 31/166*** | (2006.01) |
| ***A61P 11/00*** | (2006.01) |
| ***A61P 35/00*** | (2006.01) |

(52) U.S. Cl.

CPC ........ *A61K 31/4375* (2013.01); *A61K 9/4858* (2013.01); *A61K 9/4866* (2013.01); *A61K 31/166* (2013.01); *A61P 11/00* (2018.01); *A61P 35/00* (2018.01)

(58) Field of Classification Search

None

See application file for complete search history.

(56) References Cited

U.S. PATENT DOCUMENTS

| | | | |
|---|---|---|---|
| 6,960,614 | B2 | 11/2005 | Barrett et al. |
| 7,060,856 | B2 | 6/2006 | Macikenas et al. |
| 7,411,001 | B2 | 8/2008 | Barrett et al. |
| 10,351,559 | B2 | 7/2019 | Zhang et al. |
| 11,066,358 | B1 | 7/2021 | Irdam |
| 11,084,780 | B1 | 8/2021 | Patterson et al. |
| 12,324,791 | B2 | 6/2025 | Iloeje et al. |
| 2014/0155372 | A1 | 6/2014 | Lee et al. |
| 2016/0355510 | A1 | 12/2016 | Springer et al. |
| 2022/0257543 | A1 | 8/2022 | Patterson et al. |
| 2023/0293465 | A1 | 9/2023 | Baker et al. |

FOREIGN PATENT DOCUMENTS

| | | | |
|---|---|---|---|
| EP | 3560516 | A1 | 10/2019 |
| WO | WO-0200213 | A1 | 1/2002 |
| WO | WO-0206213 | A2 | 1/2002 |
| WO | WO-2004045617 | A1 | 6/2004 |
| WO | WO-2005040098 | A1 | 5/2005 |
| WO | WO-2006061712 | A2 | 6/2006 |
| WO | WO-2006134469 | A1 | 12/2006 |
| WO | WO-2007042885 | A2 | 4/2007 |
| WO | 2019051296 | A1 | 3/2019 |
| WO | 2019113345 | A1 | 6/2019 |
| WO | 2020055760 | A1 | 3/2020 |
| WO | WO-2021202981 | A1 | 10/2021 |

OTHER PUBLICATIONS

Roskoski, Pharmacological Research (2018), 135, p. 239-258.*

Berge, S.M., et al., "Pharmaceutical Salts," Journal of Pharmaceutical Sciences 66(1):1-19, Elsevier, United States (Jan. 1977).

Borght, K.V.D., et al., "BIGL: Biochemically Intuitive Generalized Loewe Null Model for Prediction of the Expected Combined Effect Compatible with Partial Agonism and Antagonism," Scientific Reports 7(1):17935, Nature Publishing Group, United Kingdom (Dec. 2017).

Chapman, P.B., et al., "Improved Survival with Vemurafenib in Melanoma With BRAF V600E Mutation," The New England Journal of Medicine 364(26):2507-2516, Massachusetts Medical Society, United States (Jun. 2011).

Dombi, E., et al., "NF1 Plexiform Neurofibroma Growth Rate by Volumetric MRI: Relationship to Age and Body Weight," Neurology 68(9):643-647, Lippincott Williams & Wilkins, United States (Feb. 2007).

Flaherty, K.T., et al., "Improved Survival With MEK Inhibition in BRAF-mutated Melanoma," The New England Journal of Medicine 367(2):107-114, Massachusetts Medical Society, United States (Jul. 2012).

(Continued)

*Primary Examiner* — Brian J Davis

(74) *Attorney, Agent, or Firm* — Blank Rome LLP

(57) ABSTRACT

The present disclosure relates to methods of treating cancers comprising coadministration of mirdametinib or a pharmaceutically acceptable salt form thereof, and lifirafenib or a pharmaceutically acceptable salt form thereof, to a patient in need thereof. Also disclosed are pharmaceutical compositions of mirdametinib or a pharmaceutically acceptable salt form thereof, and lifirafenib or a pharmaceutically acceptable salt form thereof, for use in such cancer treatment, as well as uses of these compounds for manufacture of medicaments for the treatment of cancers.

16 Claims, 4 Drawing Sheets

(56) References Cited

OTHER PUBLICATIONS

Flaherty, K.T., et al., "Combined BRAF and MEK Inhibition in Melanoma with Braf V600 Mutations," The New England Journal of Medicine 367(18):1694-1703, Massachusetts Medical Society, United States (Nov. 2012).
Florence, A. J., "Polymorph screening in pharmaceutical development," European Pharmaceutical Review, Issue 4, accessed at URL: [https://www.europeanpharmaceuticalreview.com/article/3659/polymorph-screening-inpharmaceutical-development/] on Feb. 14, 2022, 14 pages (Aug. 19, 2010).
Hauschild, A., et al., "Dabrafenib in BRAF-mutated Metastatic Melanoma: A Multicentre, Open-label, Phase 3 Randomised Controlled Trial," Lancet 380(9839):358-365, Elsevier, United Kingdom (Jul. 2012).
International Search Report and Written Opinion for International Application No. PCT/US2021/018373, European Patent Office, Netherlands, mailed on Dec. 8, 2021, 17 pages.
International Search Report and Written Opinion for International Application No. PCT/US2021/018378, European Patent Office, Netherlands, mailed on Nov. 12, 2021, 11 pages.
International Search Report and Written Opinion for International Application No. PCT/US2021/018381, European Patent Office, Netherlands, mailed on Dec. 8, 2021, 22 pages.
International Search Report and Written Opinion for International Application No. PCT/US2021/025551, European Patent Office, Netherlands, mailed on Jul. 28, 2021, 09 pages.
Kwong, L.N., et al., "Co-clinical Assessment Identifies Patterns of BRAF Inhibitor Resistance in Melanoma," The Journal of Clinical Investigation 125(4):1459-1470, American Society for Clinical Investigation, United States (Apr. 2015).
Larkin, J., et al., "Combined Vemurafenib and Cobimetinib in BRAF-mutated Melanoma," The New England Journal of Medicine 371(20):1867-1876, Massachusetts Medical Society, United States (Nov. 2014).
Long, G.V., et al., "Dabrafenib and Trametinib Versus Dabrafenib and Placebo for Val600 BRAF-mutant Melanoma: A Multicentre, Double-blind, Phase 3 Randomised Controlled Trial," Lancet 386(9992):444-451, Elsevier, United Kingdom (Aug. 2015).
NCT00147550, "A Multicenter, Open-Label, Noncomparative Phase 1-2 Clinical And Pharmacokinetic Study Of Oral PD 0325901 In Patients With Advanced Cancer," sponsored by Pfizer, first posted Sep. 7, 2005, accessed at URL:[https://clinicaltrials.gov/ct2/show/NCT00147550] on Sep. 26, 2022, 5 pages.
NCT00174369, "Phase 2 Study Of The MEK Inhibitor PD-0325901 In Patients With Advanced Non-Small Cell Lung Cancer," sponsored by Pfizer, first posted Sep. 15, 2005, accessed at URL:[https://clinicaltrials.gov/ct2/show/NCT00174369] on Sep. 26, 2022, 5 pages.
NCT01347866, "A Multi-arm Phase 1 Dose Escalation Study Of The Safety, Pharmacokinetics, And Pharmacodynamics Of The Dual Pi3k/Mtor Inhibitors Pf-04691502 And Pf-05212384 In Combination With Experimental Or Approved Anticancer Agents In Patients With Advanced Cancer," sponsored by Pfizer, first posted May 4, 2011, accessed at URL:[https://clinicaltrials.gov/ct2/show/NCT01347866] on Sep. 26, 2022, 8 pages.
NCT02022982, "Phase I/II Study of the CDK4/6 Inhibitor Palbociclib (PD-0332991) in Combination With the MEK Inhibitor PD-0325901 for Patients With KRAS Mutant Non-Small Cell Lung Cancer and Other Solid Tumors," sponsored by Dana-Farber Cancer Institute, first posted Dec. 30, 2013, accessed at URL:[https://clinicaltrials.gov/ct2/show/NCT02022982] on Sep. 26, 2022, 6 pages.
NCT02039336, "Phase I/II Study With the Combination of Dacomitinib and PD-0325901 in Metastatic KRAS Mutation Positive Non-small Cell Lung Cancer," sponsored by The Netherlands Cancer Institute, first posted Jan. 17, 2014, accessed at URL:[https://clinicaltrials.gov/ct2/show/NCT02039336] on Sep. 26, 2022, 4 pages.
NCT02096471, "A Phase 2 Trial of the MEK Inhibitor PD-0325901 in Adolescents and Adults With NF1-Associated Morbid Plexiform Neurofibromas," sponsored by University of Alabama at Birmingham, first posted Mar. 26, 2014, accessed at URL:[https://clinicaltrials.gov/ct2/show/NCT02096471] on Sep. 26, 2022, 8 pages.
NCT02510001, "A Sequential Phase I Study of MEK1/2 Inhibitors PD-0325901 or Binimetinib Combined With cMET Inhibitor PF-02341066 in Patients With RAS Mutant and RAS Wild Type (With Aberrant c-MET) Colorectal Cancer," sponsored by University of Oxford, first posted Jul. 28, 2015, accessed at URL:[https://clinicaltrials.gov/ct2/show/NCT02510001] on Sep. 26, 2022, 12 pages.
NCT03170206, "Phase I/II Study of the CDK4/6 Inhibitor Palbociclib (PD-0332991) in Combination With the MEK Inhibitor Binimetinib (MEK 162) for Patients With Advanced KRAS Mutant Non-Small Cell Lung Cancer," sponsored by Dana-Farber Cancer Institute, first posted May 30, 2017, accessed at URL:[https://clinicaltrials.gov/ct2/show/NCT03170206] on Sep. 26, 2022, 7 pages.
NCT03905148, "A Phase 1b, Open-Label, Dose-escalation and Expansion Study to Investigate the Safety, Pharmacokinetics and Antitumor Activities of a RAF Dimer Inhibitor BGB-283 in Combination With MEK Inhibitor PD-0325901 in Patients With Advanced or Refractory Solid Tumors," sponsored by BeiGene, first posted Apr. 5, 2019, accessed at URL:[https://clinicaltrials.gov/ct2/show/NCT0390514] on Sep. 26, 2022, 6 pages.
NCT03962543, "A Phase 2b Trial of the MEK 1/2 Inhibitor (MEKi) PD-0325901 in Adult and Pediatric Patients With Neurofibromatosis Type 1 (NF1)-Associated Inoperable Plexiform Neurofibromas (PNs) That Are Causing Significant Morbidity," sponsored by Spring Works Therapeutics, Inc., first posted May 24, 2019, accessed at URL:[https://clinicaltrials.gov/ct2/show/NCT03962543] on Sep. 26, 2022, 6 pages.
Nguyen, R., et al., "Growth Dynamics of Plexiform Neurofibromas: a Retrospective Cohort Study of 201 Patients with Neurofibromatosis 1," Orphanet Journal of Rare Diseases 7:75, BioMed Central Ltd., United Kingdom (Oct. 2012).
Pacifico, M.P., et al., "False Discovery Control for Random Fields," Journal of the American Statistical Association 99(468):1002-1014, American Statistical Association, United States (Dec. 2011).
Prada, C.E., et al., "Pediatric Plexiform Neurofibromas: Impact on Morbidity and Mortality in Neurofibromatosis Type 1," The Journal of Pediatrics 160(3):461-467, Mosby, United States (Mar. 2012).
Rasmussen, S.A., et al., "Mortality in Neurofibromatosis 1: An Analysis Using U.S. Death Certificates," American Journal of Human Genetics 68(5):1110-1118, Cell Press, United States (May 2001).
Reddy, S.M., et al., "Influences of BRAF Inhibitors on the Immune Microenvironment and the Rationale for Combined Molecular and Immune Targeted Therapy," Current Oncology Reports 18(7):42, Current Science, United States (Jul. 2016).
Rizos, H., et al., "BRAF Inhibitor Resistance Mechanisms in Metastatic Melanoma: Spectrum and Clinical Impact," Clinical Cancer Research 20(7):1965-1977, American Association for Cancer Research, United States (Apr. 2014).
Tang, Z., et al., "BGB-283, a Novel RAF Kinase and EGFR Inhibitor, Displays Potent Antitumor Activity in BRAF-mutated Colorectal Cancers," Molecular Cancer Therapeutics 14(10):2187-2197, American Association for Cancer Research, Inc., United States (Oct. 2015).
Tucker, T., et al., "Different Patterns of Mast Cells Distinguish Diffuse From Encapsulated Neurofibromas in Patients With Neurofibromatosis 1," The Journal of Histochemistry and Cytochemistry 59(6):584-590, SAGE Publications, United States (Jun. 2011).
Tucker, T., et al., "Longitudinal Study of Neurofibromatosis 1 Associated Plexiform Neurofibromas," Journal of Medical Genetics 46(2):81-85, British Medical Association, United Kingdom (Feb. 2009).
The United States Pharmacopeia—National Formulary, "941 X-ray Diffraction," 23rd Edition, NF-18, pp. 1843-1844, The United States Pharmacopeial Convention, United States (1995).
Yuan, X., et al., "RAF Dimer Inhibition Enhances the Antitumor Activity of MEK Inhibitors in K-RAS Mutant Tumors," Molecular Oncology 14(8):1833-1849, John Wiley & Sons, Inc., United States (Aug. 2020).
"Springworks Therapeutics Announces Initiation of Phase 1b Clinical Trial of MEK Inhibitor PD-0325901 in Combination with

(56) References Cited

OTHER PUBLICATIONS

BeiGene's RAF Dimer Inhibitor Lifirafenib in Advanced or Refractory Solid Tumor", 2019, 2 pages, https://ir.springworkstx.com/news-releases/news-release-details/springworks-therapeutics-announces-initiation-phase-1b-clinical/.
Lamba S., et al., "RAF Suppression Synergizes With MEK Inhibition in KRAS Mutant Cancer Cells," Cell Reports, Sep. 2014, vol. 8, pp. 14751483.
Preliminary Prospectus: SpringWorks Therapeutics. Dec. 25, 2019 Sections "Mirdametimib" on p. 126, "Mirdametinib in combination with a RAF dimer inhibitor (lifirafenib)" from p. 133-137, in particular subsections "Preclinical and clinical experience" and "Combination mechanism of action" Citation is not enclosed due to copyright restrictions. A copy may be obtained from the Wayback Machine at https://web.archive.org/web/20191225031612/ https:/www.sec.gov/Archives/edgar/data/1773427/000114420419040443/tv525698-sl.htm.
Study of the Safety and Pharmacokinetics of BGB-283 (Lifirafenib) and PD-0325901 (Mirdametinib) in Participants With Advanced or Refractory Solid Tumors, [online], Nov. 1, 2019., [Apr. 2, 2026]https://clinicaltrials.gov/study/NCT03905148tab=history&a=6#version-content-panel.
Gupta D., et al., "Salts of Therapeutic Agents: Chemical, Physicochemical, and Biological Considerations" Molecules, Jul. 2018, 15 Pages.
Joseph E.W et al., "The RAF inhibitor PLX4032 inhibits ERK signaling and tumor cell proliferation in a V600E BRAFselective manner" PNAS, Aug. 2010, 6 Pages.
"Overview of Pharmaceutical Excipients Used in Tablets and Capsules," Drug Topics, Oct. 2008, 11 Pages.
Torti V.R. et al., "Epithelial Tissue Hyperplasia Induced by the RAF Inhibitor PF-04880594 Is Attenuated by a Clinically Well-Tolerated Dose of the MEK Inhibitor PD-0325901" Molecular cancer therapeutics, Oct. 2012, 10 Pages.

* cited by examiner

G1: Vehicle

G2: Compound B maleate 2.5 mg/kg

G3: Compound B maleate 1.25 mg/kg + Compound A 0.5 mg/kg

G4: Compound B maleate 1.25 mg/kg + Compound A 1.5 mg/kg

G5: Compound B maleate 1.25 mg/kg + Compound A 5 mg/kg

G1: Vehicle

G2: Compound B maleate 2.5 mg/kg

G3: Compound B maleate 1.25 mg/kg + Compound A 0.5 mg/kg

G4: Compound B maleate 1.25 mg/kg + Compound A 1.5 mg/kg

G5: Compound B maleate 1.25 mg/kg + Compound A 5 mg/kg

CO-ADMINISTRATION OF MIRDAMETINIB AND LIFIRAFENIB FOR USE IN TREATING CANCERS

FIELD OF THE INVENTION

The present disclosure relates to methods of treating cancers comprising co-administration of mirdametinib or a pharmaceutically acceptable salt form thereof, and lifirafenib or a pharmaceutically acceptable salt form thereof, to a patient in need thereof. Also disclosed are pharmaceutical compositions of mirdametinib or a pharmaceutically acceptable salt form thereof, and lifirafenib or a pharmaceutically acceptable salt form thereof, for use in such cancer treatment. The disclosure further pertains to use of combinations of mirdametinib or a pharmaceutically acceptable salt form thereof, and lifirafenib or a pharmaceutically acceptable salt form thereof, for the manufacture of medicaments for cancer treatment.

BACKGROUND

N-[(2R)-2,3-dihydroxypropoxy]-3,4-difluoro-2-(2-fluoro-4-iodoanilino)benzamide ("Compound A", "mirdametinib", "PD-0325901") is a small molecule drug which has been designed to inhibit mitogen-activated protein kinase 1 ("MEK1") and mitogen-activated protein kinase 2 ("MEK2"). MEK1 and MEK2 are proteins that play key roles in the mitogen-activated protein kinase ("MAPK") signaling pathway. The MAPK pathway is critical for cell survival and proliferation, and inappropriate activation of this pathway has been shown to help enable tumor growth. Mirdametinib is a highly specific non-ATP-competitive inhibitor of MEK1 and MEK2. By virtue of this mechanism of action, mirdametinib significantly inhibits phosphorylation of the extracellular regulated MAP kinases ERK1 and ERK2, thereby leading to impaired growth of tumor cells both in culture and in vivo. In addition, evidence indicates that inflammatory cytokine-induced increases in MEK/ERK activity contribute to the inflammation, pain, and tissue destruction associated with rheumatoid arthritis and other inflammatory diseases.

5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyrdin-2(1H)-one ("Compound B", "lifirafenib", "BGB-283") is a novel, first-in-class, investigational RAF dimer inhibitor with potent, reversible inhibition of wild-type A-RAF, B-RAF, C-RAF, and B-RAFV600E, as well as EGFR and K-RAS, thereby enabling efficacy in a broad range of tumor types driven by mutations in the MAPK pathway, such as those with K-RAS driver mutations.

Therapeutic agents targeting oncogenic B-RAF were developed within the past decade and clinical studies demonstrated unprecedented clinical responses over the then standard of care, dacarbazine (Chapman 2011), leading to the US FDA approval of 4 agents and 2 combination regimens targeting the MAPK pathway (Chapman 2011; Hauschild 2012; Larkin 2014; Long 2015). Importantly, early efforts focused on B-RAF inhibitor monotherapy; however, resistance developed quickly in most patients, with a progression-free survival ("PFS") of less than 6 months for these agents (Chapman 2011; Hauschild 2012). Insights gained from translational research highlighted MAPK reactivation as a major resistance mechanism (Rizos 2014; Kwong 2015) and led to therapeutic strategies co-targeting B-RAF and MEK—leading to a near doubling in PFS (Larkin 2014; Long 2015). However, resistance still develops in the majority of patients, though a small fraction achieves long-term disease control (Flaherty 2012a; Flaherty 2012b; reviewed by Reddy 2016). Therefore, second-generation B-RAF inhibitors combined with MEK inhibitors are highly desirable as new combinations.

BRIEF SUMMARY OF THE INVENTION

Figure 1:
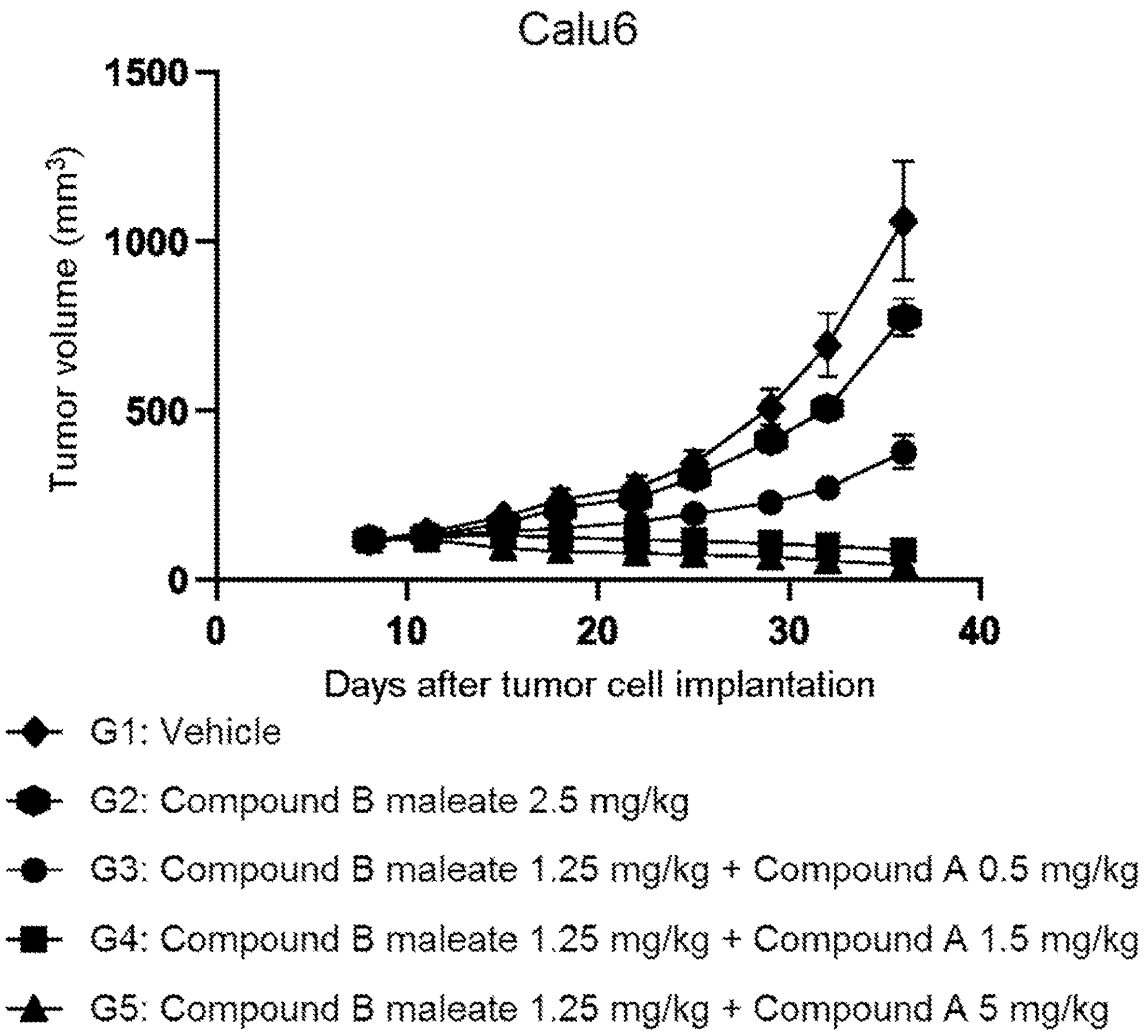
FIG. 1 shows average volume over time of Calu-6 tumors implanted in Balb/c nude mice treated with varying concentrations of Compound A and Compound B maleate.

The present disclosure features useful compositions and methods to treat various cancers comprising co-administration of mirdametinib or a pharmaceutically acceptable salt form thereof, and lifirafenib, or a pharmaceutically acceptable salt form thereof. In some aspects, the present disclosure provides a method of treating a patient having a solid tumor comprising co-administering to the patient a therapeutically effective amount of Compound A or a pharmaceutically acceptable salt form thereof, and a therapeutically effective amount of Compound B or a pharmaceutically acceptable salt form thereof. In some aspects, the present disclosure provides use of a combination of Compound A or a pharmaceutically acceptable salt form thereof, and Compound B or a pharmaceutically acceptable salt form thereof, for the manufacture of a medicament for treating a patient having a solid tumor.

In some aspects, the therapeutically effective amount of Compound A is about 1 mg to about 5 mg per day. In some aspects, the therapeutically effective amount of Compound B, or a pharmaceutically acceptable salt form thereof, is about 5 mg to about 40 mg per day.

In some aspects, the therapeutically effective amount of Compound A is about 1 mg per day and the therapeutically effective amount of Compound B, or a pharmaceutically acceptable salt form thereof, is about 5 mg to about 15 mg per day.

In some aspects, the therapeutically effective amount of Compound A is about 2 mg per day and the therapeutically effective amount of Compound B, or a pharmaceutically acceptable salt form thereof, is about 5 mg to about 40 mg per day. In some aspects, the therapeutically effective amount of Compound A is about 2 mg per day and the therapeutically effective amount of Compound B, or a pharmaceutically acceptable salt form thereof, is about 20 mg to about 35 mg per day.

In some aspects, the therapeutically effective amount of Compound A is about 3 mg per day and the therapeutically effective amount of Compound B, or a pharmaceutically acceptable salt form thereof, is about 5 mg to about 40 mg per day. In some aspects, the therapeutically effective amount of Compound A is about 3 mg per day and the therapeutically effective amount of Compound B, or a pharmaceutically acceptable salt form thereof, is about 20 mg to about 35 mg per day.

In some aspects, the therapeutically effective amount of Compound A is about 4 mg per day and the therapeutically effective amount of Compound B, or a pharmaceutically acceptable salt form thereof, is about 10 mg to about 40 mg per day. In some aspects, the therapeutically effective amount of Compound A is about 4 mg per day and the therapeutically effective amount of Compound B, or a pharmaceutically acceptable salt form thereof, is about 20 mg to about 35 mg per day.

In some aspects, the therapeutically effective amount of Compound A is about 5 mg per day and the therapeutically effective amount of Compound B, or a pharmaceutically acceptable salt form thereof, is about 10 mg to about 40 mg per day. In some aspects, the therapeutically effective amount of Compound A is about 5 mg per day and the therapeutically effective amount of Compound B, or a pharmaceutically acceptable salt form thereof, is about 20 to about 40 mg per day. In some aspects, the therapeutically effective amount of Compound A, or a pharmaceutically acceptable salt thereof, is about 1 mg per day and the therapeutically effective amount of Compound B, or a pharmaceutically acceptable salt form thereof, is about 20 mg per day. In some aspects, the therapeutically effective amount of Compound A, or a pharmaceutically acceptable salt thereof, is about 2 mg per day and the therapeutically effective amount of Compound B, or a pharmaceutically acceptable salt form thereof, is about 15 mg per day, In some aspects, the therapeutically effective amount of Compound A, or a pharmaceutically acceptable salt thereof, is about 2 mg per day and the therapeutically effective amount of Compound B, or a pharmaceutically acceptable salt form thereof, is about 20 mg per day. In some aspects, the therapeutically effective amount of Compound A, or a pharmaceutically acceptable salt thereof, is about 3 mg per day and the therapeutically effective amount of Compound B, or a pharmaceutically acceptable salt form thereof, is about 20 mg per day. In some aspects, the therapeutically effective amount of Compound A, or a pharmaceutically acceptable salt thereof, is about 2 mg per day and the therapeutically effective amount of Compound B, or a pharmaceutically acceptable salt form thereof, is about 15 mg per day. In some aspects, the therapeutically effective amount of Compound A, or a pharmaceutically acceptable salt thereof, is about 3 mg per day and the therapeutically effective amount of Compound B, or a pharmaceutically acceptable salt form thereof, is about 20 mg per day. In some aspects, the therapeutically effective amount of Compound A, or a pharmaceutically acceptable salt thereof, is about 3 mg per day and the therapeutically effective amount of Compound B, or a pharmaceutically acceptable salt form thereof, is about 15 mg per day. In some aspects, the therapeutically effective amount of Compound A, or a pharmaceutically acceptable salt thereof, is about 4 mg per day and the therapeutically effective amount of Compound B, or a pharmaceutically acceptable salt form thereof, is about 20 mg per day. In some aspects, the therapeutically effective amount of Compound A, or a pharmaceutically acceptable salt thereof, is about 4 mg per day and the therapeutically effective amount of Compound B, or a pharmaceutically acceptable salt form thereof, is about 15 mg per day. In some aspects, the therapeutically effective amount of Compound A, or a pharmaceutically acceptable salt thereof, is about 4 mg per day and the therapeutically effective amount of Compound B, or a pharmaceutically acceptable salt form thereof, is about 5 mg per day. In some aspects, the therapeutically effective amount of Compound A, or a pharmaceutically acceptable salt thereof, is about 4 mg per day and the therapeutically effective amount of Compound B, or a pharmaceutically acceptable salt form thereof, is about 10 mg per day. In some aspects, the therapeutically effective amount of Compound A, or a pharmaceutically acceptable salt thereof, is about 8 mg per day and the therapeutically effective amount of Compound B, or a pharmaceutically acceptable salt form thereof, is about 5 mg per day. In some aspects, the therapeutically effective amount of Compound A, or a pharmaceutically acceptable salt thereof, is about 8 mg per day and the therapeutically effective amount of Compound B, or a pharmaceutically acceptable salt form thereof, is about 10 mg per day. In some aspects, the therapeutically effective amount of Compound A, or a pharmaceutically acceptable salt thereof, is about 12 mg per day and the therapeutically effective amount of Compound B, or a pharmaceutically acceptable salt form thereof, is about 5 mg per day. In some aspects, the therapeutically effective amount of Compound A, or a pharmaceutically acceptable salt thereof, is about 12 mg per day and the therapeutically effective amount of Compound B, or a pharmaceutically acceptable salt form thereof, is about 10 mg per day.

In some aspects, Compound B is a pharmaceutically acceptable salt form. In some aspects, the pharmaceutically acceptable salt form of Compound B is a maleate salt. In some aspects, the maleate salt is a sesqui-maleate salt.

In some aspects, the therapeutically effective amount of Compound A is about 1 mg per day and the therapeutically effective amount of Compound B as a maleate salt is about 5 mg to about 10 mg per day. In some aspects, the therapeutically effective amount of Compound A is about 1 mg per day and the therapeutically effective amount of Compound B as a maleate salt is about 7 mg per day.

In some aspects, the therapeutically effective amount of Compound A is about 2 mg per day and the therapeutically effective amount of Compound B as a maleate salt is about 10 mg to about 30 mg per day. In some aspects, the therapeutically effective amount of Compound A is about 2 mg per day and the therapeutically effective amount of Compound B as a maleate salt is about 13 mg per day. In some aspects, the therapeutically effective amount of Compound A is about 2 mg per day and the therapeutically effective amount of Compound B as a maleate salt is about 27 mg per day.

In some aspects, the therapeutically effective amount of Compound A is about 3 mg per day and the therapeutically effective amount of Compound B as a maleate salt is about 15 mg to about 40 mg per day. In some aspects, the therapeutically effective amount of Compound A is about 3 mg per day and the therapeutically effective amount of Compound B as a maleate salt is about 20 mg per day. In some aspects, the therapeutically effective amount of Compound A is about 3 mg per day and the therapeutically effective amount of Compound B as a maleate salt is about 34 mg per day.

In some aspects, the therapeutically effective amount of Compound A is about 4 mg per day and the therapeutically effective amount of Compound B as a maleate salt is about 20 mg to about 40 mg per day. In some aspects, the therapeutically effective amount of Compound A is about 4 mg per day and the therapeutically effective amount of Compound B as a maleate salt is about 27 mg per day.

In some aspects, the therapeutically effective amount of Compound A is about 5 mg per day and the therapeutically effective amount of Compound B as a maleate salt is about 25 mg to about 40 mg per day. In some aspects, the therapeutically effective amount of Compound A is about 5 mg per day and the therapeutically effective amount of Compound B as a maleate salt is about 34 mg per day.

In some aspects, the therapeutically effective amount of Compound A, or a pharmaceutically acceptable salt thereof, is about 1 mg per day and the therapeutically effective amount of Compound B, as a maleate salt, which can be a sesqui-maleate salt, is about 27 mg per day. In some aspects, the therapeutically effective amount of Compound A, or a pharmaceutically acceptable salt thereof, is about 2 mg per day and the therapeutically effective amount of Compound B, as a maleate salt, which can be a sesqui-maleate salt, is about 20 mg per day, In some aspects, the therapeutically effective amount of Compound A, or a pharmaceutically acceptable salt thereof, is about 2 mg per day and the therapeutically effective amount of Compound B, as a maleate salt, which can be a sesqui-maleate salt, is about 27 mg per day. In some aspects, the therapeutically effective amount of Compound A, or a pharmaceutically acceptable salt thereof, is about 3 mg per day and the therapeutically effective amount of Compound B, as a maleate salt, which can be a sesqui-maleate salt, is about 27 mg per day. In some aspects, the therapeutically effective amount of Compound A, or a pharmaceutically acceptable salt thereof, is about 2 mg per day and the therapeutically effective amount of Compound B, as a maleate salt, which can be a sesqui-maleate salt, is about 20 mg per day. In some aspects, the therapeutically effective amount of Compound A, or a pharmaceutically acceptable salt thereof, is about 3 mg per day and the therapeutically effective amount of Compound B, as a maleate salt, which can be a sesqui-maleate salt, is about 27 mg per day. In some aspects, the therapeutically effective amount of Compound A, or a pharmaceutically acceptable salt thereof, is about 3 mg per day and the therapeutically effective amount of Compound B, as a maleate salt, which can be a sesqui-maleate salt, is about 20 mg per day. In some aspects, the therapeutically effective amount of Compound A, or a pharmaceutically acceptable salt thereof, is about 4 mg per day and the therapeutically effective amount of Compound B, as a maleate salt, which can be a sesqui-maleate salt, is about 27 mg per day. In some aspects, the therapeutically effective amount of Compound A, or a pharmaceutically acceptable salt thereof, is about 4 mg per day and the therapeutically effective amount of Compound B, as a maleate salt, which can be a sesqui-maleate salt, is about 20 mg per day. In some aspects, the therapeutically effective amount of Compound A, or a pharmaceutically acceptable salt thereof, is about 4 mg per day and the therapeutically effective amount of Compound B, as a maleate salt, which can be a sesqui-maleate salt, is about 7 mg per day. In some aspects, the therapeutically effective amount of Compound A, or a pharmaceutically acceptable salt thereof, is about 4 mg per day and the therapeutically effective amount of Compound B, or a pharmaceutically acceptable salt form thereof, is about 13 mg per day. In some aspects, the therapeutically effective amount of Compound A, or a pharmaceutically acceptable salt thereof, is about 8 mg per day and the therapeutically effective amount of Compound B, or a pharmaceutically acceptable salt form thereof, is about 7 mg per day. In some aspects, the therapeutically effective amount of Compound A, or a pharmaceutically acceptable salt thereof, is about 8 mg per day and the therapeutically effective amount of Compound B, or a pharmaceutically acceptable salt form thereof, is about 13 mg per day. In some aspects, the therapeutically effective amount of Compound A, or a pharmaceutically acceptable salt thereof, is about 12 mg per day and the therapeutically effective amount of Compound B, or a pharmaceutically acceptable salt form thereof, is about 7 mg per day. In some aspects, the therapeutically effective amount of Compound A, or a pharmaceutically acceptable salt thereof, is about 12 mg per day and the therapeutically effective amount of Compound B, or a pharmaceutically acceptable salt form thereof, is about 13 mg per day.

In some aspects, Compound A, or a pharmaceutically acceptable salt form thereof, and Compound B, or a pharmaceutically acceptable salt form thereof, are administered in the same or different dosage forms. In some aspects, Compound A, or a pharmaceutically acceptable salt form thereof, and Compound B, or a pharmaceutically acceptable salt form thereof, are administered in the same dosage form. In some aspects, Compound A, or a pharmaceutically acceptable salt form thereof, and Compound B, or a pharmaceutically acceptable salt form thereof, are administered orally.

In some aspects, the dosage form is a capsule.

In some aspects, Compound A is administered once per day. In some aspects, Compound B, or a pharmaceutically acceptable salt form thereof, is administered once per day.

In some aspects, the present disclosure provides a pharmaceutical composition comprising:

a. Compound A, or a pharmaceutically acceptable salt form thereof;

b. Compound B, or a pharmaceutically acceptable salt form thereof;

c. a filler;

d. a disintegrant; and e. a lubricant.

In some aspects, the pharmaceutically acceptable salt of Compound B is the maleic acid salt of Compound B.

In some aspects, the pharmaceutical composition comprises about 0.8 mg to about 1.2 mg of Compound A. In some aspects, the pharmaceutical composition comprises Compound A about 1.5 mg to about 2.5 mg.

In some aspects, the pharmaceutical composition comprises about 6 mg to about 8 mg of Compound B as the maleic acid salt. In some aspects, the pharmaceutical composition comprises about 20 mg to about 35 mg of Compound B as the maleic acid salt.

In some aspects, the filler in the pharmaceutical composition is present at about 80 wt/wt % to about 90 wt/wt %. In some aspects, the filler in the pharmaceutical composition is present at about 72.5 wt/wt % to about 85 wt/wt %. In some aspects, the filler in the pharmaceutical composition is selected from the group consisting of microcrystalline cellulose, lactose, mannitol, starch, dibasic calcium phosphate, and combinations thereof. In some aspects, the filler comprises microcrystalline cellulose. In some aspects, the filler in the pharmaceutical composition comprises silicified microcrystalline cellulose.

In some aspects, the disintegrant in the pharmaceutical composition is present at about 3.5 wt/wt % to about 4.5 wt/wt %. In some aspects, the disintegrant is selected from the group consisting of croscarmellose sodium, sodium starch glycolate, crospovidone, alginic acid, and combinations thereof. In some aspects, the disintegrant in the pharmaceutical composition comprises croscarmellose sodium.

In some aspects, the lubricant in the pharmaceutical composition is present at about 1.5 wt/wt % to about 5.0 wt/wt %. In some aspects, the lubricant is selected from the group consisting of sodium stearyl fumarate, magnesium stearate, glyceryl dibehenate, talc, and combinations thereof. In some aspects, the lubricant in the pharmaceutical composition comprises sodium stearyl fumarate. In some aspects, the lubricant in the pharmaceutical composition comprises magnesium stearate.

In some aspects, the pharmaceutical composition comprising Compound A or a pharmaceutically acceptable salt form thereof, and Compound B, or a pharmaceutically acceptable salt form thereof, is a tablet or capsule. In some aspects, the pharmaceutical composition comprising Compound A, or a pharmaceutically acceptable salt form thereof, and Compound B, or a pharmaceutically acceptable salt form thereof, is a capsule.

In some aspects, the capsule comprises about 1 mg of Compound A and about 7 mg of the maleic acid salt of Compound B, wherein each component of the capsule is as follows:

a. about 0.8 wt/wt % to about 1.2 wt/wt % of Compound A;
b. about 6 wt/wt % to about 8 wt/wt % of the maleic acid salt of Compound B;
c. about 80 wt/wt % to about 90 wt/wt % of silicified microcrystalline cellulose;
d. about 3.5 wt/wt % to about 4.5 wt/wt % of croscarmellose sodium;
e. about 1.5 wt/wt % to about 5.0 wt/wt % of sodium stearyl fumarate; and
f. a gelatin capsule which encapsulates components a-e.

In some aspects, the capsule comprises about 2 mg of Compound A and about 27 mg of the maleic acid salt of Compound B, wherein each component of the capsule is as follows:

a. about 0.8 wt/wt % to about 1.3 wt/wt % of Compound A;
b. about 12.3 wt/wt % to about 15.0 wt/wt % of the maleic acid salt of Compound B;
c. about 72.5 wt/wt % to about 85 wt/wt % of silicified microcrystalline cellulose;
d. about 3.5 wt/wt % to about 4.5 wt/wt % of croscarmellose sodium;
e. about 1.5 wt/wt % to about 5.0 wt/wt % of sodium stearyl fumarate; and
f. a gelatin capsule which encapsulates components a-e.

In some aspects, Compound A or a pharmaceutically acceptable salt form thereof, and Compound B or a pharmaceutically acceptable salt form of thereof, are administered to treat a patient having a cancer. In some aspects, the cancer is a solid tumor. In some aspects, the solid tumor is selected from the group consisting of malignant peripheral nerve sheath tumor, biliary tract cancer, breast cancer, cholangiocarcinoma, urothelial cancer, uterine neoplasm, lung adenocarcinoma, squamous non-small cell lung cancer, non-squamous non-small cell lung cancer, gastric cancer, sarcoma, bladder cancer, head and neck cancer, small cell lung cancer, endometrial cancer, esophageal cancer, adenoid cystic carcinoma, gallbladder cancer, colorectal cancer ("CRC"), thyroid cancer, hepatocellular cancer, prostate cancer, oral cancer, cervical cancer, pancreatic carcinoma, ovarian cancer, melanoma, and serous carcinoma to the peritoneum. In some aspects, the patient has non-small cell lung cancer. In some aspects, the patient has endometrial cancer. In some aspects, the patient has ovarian cancer. In some aspects, the patient has low grade serous ovarian cancer. In some aspects, the patient has a confirmed mutation in one or more of KRAS, NRAS, HRAS, BRAF, NF1, MEK1, and MEK2. In some aspects, the patient has a confirmed mutation in RASA1 and/or RAF1.

In some aspects, Compound A or a pharmaceutically acceptable salt form thereof, and Compound B or a pharmaceutically acceptable salt form thereof, are administered on a 28-day dosing cycle comprising: (a) 21 days in which Compound A or a pharmaceutically acceptable salt form thereof, and Compound B or a pharmaceutically acceptable salt form thereof, are both administered; and (b) 7 days in which neither Compound A or a pharmaceutically acceptable salt form thereof, nor Compound B or a pharmaceutically acceptable salt form thereof, is administered. In some aspects, Compound A or a pharmaceutically acceptable salt form thereof, and Compound B or a pharmaceutically acceptable salt form thereof, are administered on a 28-day dosing cycle comprising (a) 21 days in which Compound A or a pharmaceutically acceptable salt form thereof, and Compound B or a pharmaceutically acceptable salt form thereof are both administered; followed by (b) 7 days in which neither Compound A or a pharmaceutically acceptable salt form thereof, nor Compound B or a pharmaceutically acceptable salt form thereof, is administered. In some aspects, Compound A or a pharmaceutically acceptable salt form thereof, and Compound B or a pharmaceutically acceptable salt form thereof, are administered on a 28-day dosing cycle comprising (a) three 7-day periods each comprising (i) 5 days in which Compound A or a pharmaceutically acceptable salt form thereof, and Compound B or a pharmaceutically acceptable salt form thereof, are both administered and (ii) 2 days in which neither Compound A or a pharmaceutically acceptable salt form thereof, nor Compound B or a pharmaceutically acceptable salt form thereof are administered; and (b) 7 days in which neither Compound A or a pharmaceutically acceptable salt form thereof, nor Compound B or a pharmaceutically acceptable salt form thereof, is administered. In some aspects, Compound A or a pharmaceutically acceptable salt form thereof, and Compound B or a pharmaceutically acceptable salt form thereof, are administered on a 28-day dosing cycle comprising (a) three 7-day periods each comprising (i) 5 days in which Compound A or a pharmaceutically acceptable salt form thereof, and Compound B or a pharmaceutically acceptable salt form thereof, are both administered and (ii) 2 days in which neither Compound A or a pharmaceutically acceptable salt form thereof, nor Compound B or a pharmaceutically acceptable salt form thereof, is administered; followed by (b) 7 days in which neither Compound A or a pharmaceutically acceptable salt form thereof, nor Compound B or a pharmaceutically acceptable salt form thereof, is administered. In some aspects, Compound A or a pharmaceutically acceptable salt form thereof, and Compound B or a pharmaceutically acceptable salt form thereof, are administered on a 28-day dosing cycle comprising (a) three 7-day periods each comprising (i) 4 days in which Compound A or a pharmaceutically acceptable salt form thereof, and Compound B or a pharmaceutically acceptable salt form thereof, are both administered and (ii) 3 days in which neither Compound A or a pharmaceutically acceptable salt form thereof, nor Compound B or a pharmaceutically acceptable salt form thereof are administered; and (b) 7 days in which neither Compound A or a pharmaceutically acceptable salt form thereof, nor Compound B or a pharmaceutically acceptable salt form thereof, is administered. In some aspects, Compound A or a pharmaceutically acceptable salt form thereof, and Compound B or a pharmaceutically acceptable salt form thereof, are administered on a 28-day dosing cycle comprising (a) three 7-day periods each comprising (i) 4 days in which Compound A or a pharmaceutically acceptable salt form thereof, and Compound B or a pharmaceutically acceptable salt form thereof, are both administered and (ii) 3 days in which neither Compound A or a pharmaceutically acceptable salt form thereof, nor Compound B or a pharmaceutically acceptable salt form thereof, is administered; followed by (b) 7 days in which neither Compound A or a pharmaceutically acceptable salt form thereof, nor Compound B or a pharmaceutically acceptable salt form thereof, is administered.

In some aspects, the pharmaceutical composition comprising Compound A or a pharmaceutically acceptable salt form thereof, and Compound B or a pharmaceutically acceptable salt form thereof, is administered on a 28-day dosing cycle comprising: (a) 21 days in which the pharmaceutical composition comprising Compound A or a pharmaceutically acceptable salt form thereof, and Compound B or a pharmaceutically acceptable salt form thereof form, is administered; and (b) 7 days in which the pharmaceutical composition comprising Compound A or a pharmaceutically acceptable salt form thereof, and Compound B or a pharmaceutically acceptable salt form thereof, is not administered. In some aspects, the pharmaceutical composition comprising Compound A or a pharmaceutically acceptable salt form thereof, and Compound B or a pharmaceutically acceptable salt form thereof, is administered on a 28-day dosing cycle comprising (a) 21 days in which the pharmaceutical composition comprising Compound A or a pharmaceutically acceptable salt form thereof, and Compound B or a pharmaceutically acceptable salt form thereof, is administered; followed by (b) 7 days in which the pharmaceutical composition comprising Compound A or a pharmaceutically acceptable salt form thereof, and Compound B or a pharmaceutically acceptable salt form thereof is not administered. In some aspects, the pharmaceutical composition comprising Compound A or a pharmaceutically acceptable salt form thereof, and Compound B or a pharmaceutically acceptable salt form of thereof, is administered on a 28-day dosing cycle comprising (a) three 7-day periods each comprising (i) 5 days in which the pharmaceutical composition comprising Compound A or a pharmaceutically acceptable salt form thereof, and Compound B or a pharmaceutically acceptable salt form of thereof is administered and (ii) 2 days in which the pharmaceutical composition comprising Compound A or a pharmaceutically acceptable salt form thereof, and Compound B or a pharmaceutically acceptable salt form of thereof, is not administered; and (b) 7 days in which the pharmaceutical composition comprising Compound A or a pharmaceutically acceptable salt form thereof, and Compound B or a pharmaceutically acceptable salt form thereof, is not administered. In some aspects, the pharmaceutical composition comprising Compound A or a pharmaceutically acceptable salt form thereof, and Compound B or a pharmaceutically acceptable salt form thereof, is administered on a 28-day dosing cycle comprising (a) three 7-day periods each comprising (i) 5 days in which the pharmaceutical composition comprising Compound A or a pharmaceutically acceptable salt form thereof, and Compound B or a pharmaceutically acceptable salt form thereof, is administered and (ii) 2 days in which the pharmaceutical composition comprising Compound A or a pharmaceutically acceptable salt form thereof, and Compound B or a pharmaceutically acceptable salt form thereof, is not administered; followed by (b) 7 days in which the pharmaceutical composition comprising Compound A or a pharmaceutically acceptable salt form thereof, and Compound B or a pharmaceutically acceptable salt form thereof, is not administered. In some aspects, the pharmaceutical composition comprising Compound A or a pharmaceutically acceptable salt form thereof, and Compound B or a pharmaceutically acceptable salt form thereof, is administered on a 28-day dosing cycle comprising (a) three 7-day periods each comprising (i) 4 days in which the pharmaceutical composition comprising Compound A or a pharmaceutically acceptable salt form thereof, and Compound B or a pharmaceutically acceptable salt form thereof, is administered and (ii) 3 days in which the pharmaceutical composition comprising Compound A or a pharmaceutically acceptable salt form thereof, and Compound B or a pharmaceutically acceptable salt form thereof, is administered; and (b) 7 days in which the pharmaceutical composition comprising Compound A or a pharmaceutically acceptable salt form thereof, and Compound B or a pharmaceutically acceptable salt form of thereof, is not administered. In some aspects, the pharmaceutical composition comprising Compound A or a pharmaceutically acceptable salt form thereof, and Compound B or a pharmaceutically acceptable salt form of thereof, is administered on a 28-day dosing cycle comprising (a) three 7-day periods each comprising (i) 4 days in which the pharmaceutical composition comprising Compound A or a pharmaceutically acceptable salt form thereof, and Compound B or a pharmaceutically acceptable salt form of thereof, is administered and (ii) 3 days in which the pharmaceutical composition comprising Compound A or a pharmaceutically acceptable salt form thereof, and Compound B or a pharmaceutically acceptable salt form thereof, is not administered; followed by (b) 7 days in which the pharmaceutical composition comprising Compound A or a pharmaceutically acceptable salt form thereof, and Compound B or a pharmaceutically acceptable salt form thereof, is not administered.

In some aspects, the 28-day dosing cycle is repeated up to a total of 24 consecutive 28-day dosing cycles.

In some aspects, only Compound B, or a pharmaceutically acceptable salt form thereof, is administered for a lead-in period prior to the first of the 28-day dosing cycles discussed above. In some aspects, the amount of Compound B, or a pharmaceutically acceptable salt thereof, administered in the lead-in period is the same or lower than the amount of Compound B, or a pharmaceutically acceptable salt thereof, administered during the first of the 28-day dosing cycles discussed above.

In some aspects, one or both of Compound A, or a pharmaceutically acceptable salt form thereof, and Compound B, or a pharmaceutically acceptable salt form thereof, is administered for a lead-in period prior to the first of the 28-day dosing cycles discussed above at a lower dose than the therapeutically effective amount of Compound A, or a pharmaceutically acceptable salt form thereof, and Compound B, or a pharmaceutically acceptable salt thereof, administered during the first of the 28-day dosing cycles discussed above. In some aspects, the amount of Compound A, or a pharmaceutically acceptable salt thereof, administered in the lead-in period is the same as the amount of Compound A, or a pharmaceutically acceptable salt thereof, administered during the first of the 28-day dosing cycles discussed above. In some aspects, the amount of Compound A, or a pharmaceutically acceptable salt thereof, administered in the lead-in period is lower than the amount of Compound A, or a pharmaceutically acceptable salt thereof, administered during the first of the 28-day dosing cycles discussed above. In some aspects, the amount of Compound B, or a pharmaceutically acceptable salt thereof, administered in the lead-in period is the same as the amount of Compound B, or a pharmaceutically acceptable salt thereof, administered during the first of the 28-day dosing cycles discussed above. In some aspects, the amount of Compound B, or a pharmaceutically acceptable salt thereof, administered in the lead-in period is lower than the amount of Compound B, or a pharmaceutically acceptable salt thereof, administered during the first of the 28-day dosing cycles discussed above.

In some aspects, the amount of Compound A, or a pharmaceutically acceptable salt thereof, administered in the lead-in period is about 1 mg to about 5 mg per day. In some aspects, the amount of Compound A, or a pharmaceutically acceptable salt thereof, administered in the lead-in period about 1 mg per day. In some aspects, the amount of Compound A, or a pharmaceutically acceptable salt thereof, administered in the lead-in period about 2 mg per day. In some aspects, the amount of Compound A, or a pharmaceutically acceptable salt thereof, administered in the lead-in period about 3 mg per day.

In some aspects, the amount of Compound B, or a pharmaceutically acceptable salt thereof, administered in the lead-in period is about 5 mg to about 25 mg per day. In some aspects, the amount of Compound B, or a pharmaceutically acceptable salt thereof, administered in the lead-in period is about 5 mg to about 20 mg per day. In some aspects, the amount of Compound B, or a pharmaceutically acceptable salt thereof, administered in the lead-in period is about 5 mg to about 15 mg per day. In some aspects, the amount of Compound B, or a pharmaceutically acceptable salt thereof, administered in the lead-in period is about 5 mg per day. In some aspects, the amount of Compound B, or a pharmaceutically acceptable salt thereof, administered in the lead-in period is about 10 mg per day. In some aspects, the amount of Compound B, or a pharmaceutically acceptable salt thereof, administered in the lead-in period is about 15 mg per day. In some aspects, the amount of Compound B, or a pharmaceutically acceptable salt thereof, administered in the lead-in period is about 20 mg per day.

In some aspects, the Compound B administered in the lead-in period is a pharmaceutically acceptable salt form. In some aspects, the pharmaceutically acceptable salt form is a maleate salt, which can be a sesqui-maleate salt. In some aspects, the amount of Compound B as a maleate salt, which can be a sesqui-maleate salt, administered in the lead-in period is about 5 mg to about 40 mg per day. In some aspects, the amount of Compound B as a maleate salt, which can be a sesqui-maleate salt, administered in the lead-in period is about 5 mg to about 30 mg per day. In some aspects, the amount of Compound B as a maleate salt, which can be a sesqui-maleate salt, administered in the lead-in period is about 5 mg to about 25 mg per day. In some aspects, the amount of Compound B as a maleate salt, which can be a sesqui-maleate salt, administered in the lead-in period is about 7 mg per day. In some aspects, the amount of Compound B as a maleate salt, which can be a sesqui-maleate salt, administered in the lead-in period is about 13 mg per day. In some aspects, the amount of Compound B as a maleate salt, which can be a sesqui-maleate salt, administered in the lead-in period is about 20 mg per day. In some aspects, the amount of Compound B as a maleate salt, which can be a sesqui-maleate salt, administered in the lead-in period is about 27 mg per day.

In some aspects, the Compound A, or a pharmaceutically acceptable salt thereof, and/or the Compound B, or a pharmaceutically acceptable salt thereof, is administered daily during the lead-in period. In some aspects, the Compound A, or a pharmaceutically acceptable salt thereof, and/or Compound B, or a pharmaceutically acceptable salt thereof, is administered once daily during the lead-in period. In some aspects, Compound A, or pharmaceutically acceptable salt thereof, and Compound B, or a pharmaceutically acceptable salt form thereof, are administered orally during the lead-in period.

In some aspects, the Compound A, or a pharmaceutically acceptable salt thereof, and Compound B, or a pharmaceutically acceptable salt form thereof, are administered in the same or different dosage forms during the lead-in period. In some aspects, the Compound A, or a pharmaceutically acceptable salt thereof, and Compound B, or a pharmaceutically acceptable salt form thereof, are administered in the same dosage form during the lead-in period. In some aspects, the dosage form is a capsule.

In some aspects, Compound A, or a pharmaceutically acceptable salt thereof, and Compound B, or a pharmaceutically acceptable salt form thereof, are administered in different dosage forms during the lead-in period. In some aspects, Compound A is administered before, concomitantly, or subsequently to the administering of Compound B, or a pharmaceutically acceptable salt form thereof during the lead-in period. In some aspects, the dosage form of Compound A, or a pharmaceutically acceptable salt thereof, is a capsule. In some aspects, he dosage form of Compound B, or a pharmaceutically acceptable salt form thereof, is a capsule In some aspects, the lead-in period begins 21 days before the first 28-day dosing cycle. In some aspects, the lead-in period begins 14 days before the first 28-day dosing cycle. In some aspects, the lead-in period begins 10 days before the first 28-day dosing cycle. In some aspects, the lead-in period begins 7 days before the first 28-day dosing cycle.

In some aspects, methods of treating a patient having a solid tumor comprising administering once daily 2 mg Compound A as free base and 15 mg Compound B, or a pharmaceutically acceptable salt thereof, are described herein.

In some aspects, methods of treating a patient having a solid tumor comprising administering once daily 2 mg Compound A as free base and 20 mg Compound B, or a pharmaceutically acceptable salt thereof, are described herein In some aspects, methods of treating a patient having a solid tumor comprising a 7 day cycle that comprises (a) administering once daily 3 mg of Compound A free base and 20 mg of Compound B, or a pharmaceutically acceptable salt form for 5 consecutive days; followed by (b) administering no Compound A or Compound B for 2 consecutive days, are described herein.

In some aspects, methods of treating a patient having a solid tumor comprising:

(a) a lead-in period that comprises administering once daily 3 mg Compound A free base and 10 mg Compound B, or a pharmaceutically acceptable salt form thereof, for 14 consecutive days; followed by (b) a 7 day treatment cycle that comprises (i) administering once daily 3 mg of Compound A free base and 20 mg of Compound B, or a pharmaceutically acceptable salt form therefore, for 5 consecutive days; followed by (ii) administering no Compound A or Compound B for 2 consecutive days, are described herein.

In some aspects, methods of treating a patient having a solid tumor comprising:

(a) a lead-in period that comprises administering a total of 2 mg Compound A free base divided over two doses per day and 15 mg Compound B, or a pharmaceutically acceptable salt form thereof, once daily for 14 consecutive days; followed by (b) a 7 day treatment cycle that comprises (i) administering 1 mg of Compound A free base twice daily and 15 mg of Compound B, or a pharmaceutically acceptable salt form therefore, once daily for 5 consecutive days; followed by (ii) administering no Compound A or Compound B for 2 consecutive days are described herein.

In some aspects, methods of treating a patient having a solid tumor comprising:

(a) a lead-in period that comprises administering 15 mg Compound B, or a pharmaceutically acceptable salt form thereof, once daily for 14 consecutive days; followed by (b) a 7 day treatment cycle that comprises (i) administering once daily 1 mg of Compound A free base and 20 mg of Compound B, or a pharmaceutically acceptable salt form therefore, once daily for 5 consecutive days; followed by (ii) administering no Compound A or Compound B for 2 consecutive days are described herein.

In some aspects, methods of treating a patient having a solid tumor comprising:

(a) a lead-in period that comprises administering 15 mg Compound B, or a pharmaceutically acceptable salt form thereof, once daily for 14 consecutive days; followed by (b) a 7 day treatment cycle that comprises (i) administering once daily 2 mg of Compound A free base and 20 mg of Compound B, or a pharmaceutically acceptable salt form therefore, once daily for 5 consecutive days; followed by (ii) administering no Compound A or Compound B for 2 consecutive days are described herein.

In some aspects, methods of treating a patient having a solid tumor comprising a 7 day cycle that comprises (a) administering once daily 4 mg of Compound A free base and 20 mg of Compound B, or a pharmaceutically acceptable salt form for 5 consecutive days; followed by (b) administering no Compound A or Compound B for 2 consecutive days are described herein.

In some aspects, methods of treating a patient having a solid tumor comprising:

(a) a lead-in period that comprises administering 15 mg Compound B, or a pharmaceutically acceptable salt form thereof, once daily for 14 consecutive days; followed by (b) a 7 day treatment cycle that comprises (i) administering once daily 3 mg of Compound A free base and 20 mg of Compound B, or a pharmaceutically acceptable salt form therefore, once daily for 5 consecutive days; followed by (ii) administering no Compound A or Compound B for 2 consecutive days are provided herein.

In some aspects, methods of treating a patient having a solid tumor comprising:

(a) a lead-in period that comprises administering 15 mg Compound B, or a pharmaceutically acceptable salt form thereof, once daily for 14 consecutive days; followed by (b) a 7 day treatment cycle that comprises (i) administering once daily 4 mg of Compound A free base and 20 mg of Compound B, or a pharmaceutically acceptable salt form therefore, once daily for 5 consecutive days; followed by (ii) administering no Compound A or Compound B for 2 consecutive days are described herein.

In some aspects, methods of treating a patient having a solid tumor comprising:

(a) a lead-in period that comprises administering a total of 3 mg Compound A free base divided over two doses per day and 15 mg Compound B, or a pharmaceutically acceptable salt form thereof, once daily, for 14 consecutive days; followed by (b) a 7 day treatment cycle that comprises (i) administering once daily 3 mg of Compound A free base and 15 mg of Compound B, or a pharmaceutically acceptable salt form therefore, for 5 consecutive days; followed by (ii) administering no Compound A or Compound B for 2 consecutive days are provided herein.

In some aspects, methods of treating a patient having a solid tumor comprising:

(a) a lead-in period that comprises administering a total of 4 mg Compound A free base divided over two doses per day and 15 mg Compound B, or a pharmaceutically acceptable salt form thereof, once daily for 14 consecutive days; followed by (b) a 7 day treatment cycle that comprises (i) administering once daily 4 mg of Compound A free base and 15 mg of Compound B, or a pharmaceutically acceptable salt form therefore, once daily for 5 consecutive days; followed by (ii) administering no Compound A or Compound B for 2 consecutive days are described herein.

In some aspects, methods of treating a patient having a solid tumor comprising administering twice daily 2 mg Compound A as free base and once daily 5 mg Compound B, or a pharmaceutically acceptable salt thereof, are described herein.

In some aspects, methods of treating a patient having a solid tumor comprising administering twice daily 4 mg Compound A as free base and once daily 5 mg Compound B, or a pharmaceutically acceptable salt thereof, are described herein.

In some aspects, methods of treating a patient having a solid tumor comprising administering twice daily 6 mg Compound A as free base and once daily 5 mg Compound B, or a pharmaceutically acceptable salt thereof, are described herein.

In some aspects, methods of treating a patient having a solid tumor comprising administering twice daily 2 mg Compound A as free base and twice daily 5 mg Compound B, or a pharmaceutically acceptable salt thereof, are described herein.

In some aspects, methods of treating a patient having a solid tumor comprising administering twice daily 4 mg Compound A as free base and twice daily 5 mg Compound B, or a pharmaceutically acceptable salt thereof, are described herein.

In some aspects, methods of treating a patient having a solid tumor comprising administering twice daily 6 mg Compound A as free base and twice daily 5 mg Compound B, or a pharmaceutically acceptable salt thereof, are described herein.

Definitions

To facilitate understanding of the disclosure set forth herein, a number of terms are defined below.

Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

In this specification and the appended claims, the singular forms "a," "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The terms "Compound A", "mirdametinib", and "PD-0325901" refer to the single enantiomer N-[(2R)-2,3-dihydroxypropoxy]-3,4-difluoro-2-(2-fluoro-4-iodoanilino)benzamide. The structure of Compound A is as follows:

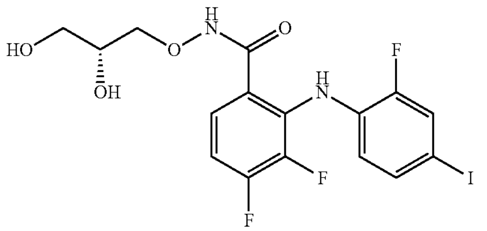 [SMILES: O=C(NOC[C@H](O)CO)c1ccc(F)c(F)c1Nc1ccc(I)cc1F]

The terms "Compound B", "lifirafenib", and "BGB-283" refer to the single enantiomer 5-(((1R,1aS,6bR)-1-(6-(trifluoromethyl)-1H-benzo[d]imidazol-2-yl)-1a,6b-dihydro-1H-cyclopropa[b]benzofuran-5-yl)oxy)-3,4-dihydro-1,8-naphthyrdin-2(1H)-one. The structure of Compound B is below:

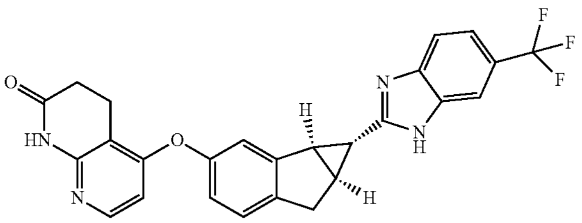 [SMILES: O=C1CCc2c(Oc3ccc4c(c3)[C@@H]3[C@H](C4)[C@H]3c3nc4ccc(C(F)(F)F)cc4[nH]3)ccnc2N1]

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

As used herein, the terms "treat," "treated," and "treating" mean both therapeutic treatment and prophylactic or preventative measures wherein the object is to prevent or slow down (lessen) an undesired physiological condition, disorder, or disease, or obtain beneficial or desired clinical results. Thus, those in need of treatment include those already diagnosed with or suspected of having the disorder. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment. The term "therapeutically effective amount" is meant to include the amount of a compound that, when administered, is sufficient to prevent development of, or alleviate to some extent, one or more of the symptoms of a disorder, disease, or condition being treated. The term "therapeutically effective amount" also refers to the amount of a compound that is sufficient to elicit the biological or medical response of a cell, tissue, system, animal, or human, which is being sought by a researcher, veterinarian, medical doctor, or clinician.

In certain aspects, a subject is successfully "treated" for cancer, e.g., lung cancer or ovarian cancer, according to the methods of the present invention if the patient shows one or more of the following: a reduction in the number of or complete absence of cancer cells; relief of one or more symptoms associated with the specific cancer; reduced morbidity and mortality; improvement in quality of life; increased progression-free survival (PFS), disease-free survival (DFS), overall survival (OS), metastasis-free survival (MFS), complete response (CR), minimal residual disease (MRD), partial response (PR), stable disease (SD), a decrease in progressive disease (PD), an increased time to progression (TTP), or any combination thereof. In some aspects, nationally or internationally accepted standards of treatment outcomes in a given cancer can be used to determine whether the combination of effective amounts of mirdametinib and lifirafenib meets any of these particular endpoints (e.g., CR, PFS, PR).

The terms "pharmaceutically acceptable carrier," "pharmaceutically acceptable excipient," "physiologically acceptable carrier," or "physiologically acceptable excipient" refer to a pharmaceutically acceptable material, composition, or vehicle, such as a liquid or solid filler, diluent, excipient, solvent, or encapsulating material. In one aspect, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See *Remington: The Science and Practice of Pharmacy,* 21$^{st}$ Edition, Lippincott Williams & Wilkins: Philadelphia, PA, 2005; *Handbook of Pharmaceutical Excipients,* 5$^{th}$ Edition, Rowe et al., Eds., The Pharmaceutical Press and the American Pharmaceutical Association: 2005; and *Handbook of Pharmaceutical Additives,* 3$^{rd}$ Edition, Ash and Ash Eds., Gower Publishing Company: 2007; Pharmaceutical Preformulation and Formulation, Gibson Ed., CRC Press LLC: Boca Raton, FL, 2004 (incorporated herein by reference). Excipients can include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration.

Exemplary excipients include, but are not limited to: butylated hydroxytoluene (BHT), calcium carbonate, calcium phosphate (dibasic), calcium stearate, croscarmellose, cross-linked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

The term "pharmaceutical composition," as used herein, represents a composition containing a compound described herein formulated with a pharmaceutically acceptable excipient, and can be manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); for intrathecal injection; for intracerebroventricular injections; for intraparenchymal injection; or in any other pharmaceutically acceptable formulation.

The term "pharmaceutically-acceptable salts" refers to the relatively non-toxic, inorganic and organic acid addition salts of Compound A or Compound B. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J. Pharm. Sci. 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In certain aspects, the compounds of the present invention may contain one or more acidic functional groups and, thus, are capable of forming pharmaceutically acceptable salts with pharmaceutically acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, e.g., Berge et al., supra).

The terms "about" or "approximately" means within a range of an acceptable error for a particular value as determined by one of ordinary skill in the art, which depends in part on how the value is measured or determined. In certain aspects, the term "about" or "approximately" means within 1, 2, 3, or 4 standard deviations. In some aspects, the term "about" or "approximately" means a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

As used herein, the term "administration" refers to the administration of a composition (e.g., a compound or a preparation that includes a compound as described herein) to a subject or system. Administration to an animal subject (e.g., to a human) can be by any appropriate route, such as one described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The terms "co-administration", "co-administering", or "co-administered" refer to administering a combination of therapeutic agents, such as, for example, a combination of mirdametinib and lifirafenib. The combination can be administered as two separate entities, such as, for example, in separate capsules or tablets, or as a single combination entity, such as, for example, in the same capsule or tablet. One therapeutic agent (e.g., Compound A, or a pharmaceutically acceptable salt form thereof) can be administered before, concomitantly, or subsequently to the administering of the other therapeutic agent (e.g., Compound B, or a pharmaceutically acceptable salt form thereof) to the subject.

It is understood that wherever aspects are described herein with the language "comprising," otherwise analogous aspects described in terms of "consisting of" and/or "consisting essentially of" are also provided.

The details of one or more aspects are set forth in the description below. Other features, objects, and advantages will be apparent from the description and from the claims.

DETAILED DESCRIPTION OF THE INVENTION

The present inventors have developed a method of treating certain cancers by co-administering mirdametinib and lifirafenib. Also disclosed are dosage forms comprising these compounds for co-administration, as well as uses of these compounds for manufacture of medicaments for the treatment of certain cancers.

In some aspects, the present disclosure provides a method of treating a patient having a solid tumor comprising co-administering to the patient a therapeutically effective amount of Compound A or a pharmaceutically acceptable salt form thereof, and a therapeutically effective amount of Compound B or a pharmaceutically acceptable salt form thereof.

In some aspects, the therapeutically effective amount of Compound A, or a pharmaceutically acceptable salt form thereof, is about 1 mg to about 15 mg per day. In some aspects, the therapeutically effective amount of Compound A, or a pharmaceutically acceptable salt form thereof, is about 1 mg to about 12 mg per day. In some aspects, the therapeutically effective amount of Compound A, or a pharmaceutically acceptable salt form thereof, is about 1 mg to about 10 mg per day. In some aspects, the therapeutically effective amount of Compound A is about 1 mg to about 5 mg per day. In some aspects, the therapeutically effective amount of Compound A, or a pharmaceutically acceptable salt form thereof, is about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, or about 15 mg.

In some aspects, Compound A is in free base form.

In some aspects, the therapeutically effective amount of Compound B, or a pharmaceutically acceptable salt form thereof, is about 5 mg to about 40 mg per day. In some aspects, the therapeutically effective amount of Compound B, or a pharmaceutically acceptable salt form thereof, is about 5 mg to about 35 mg, about 5 mg to about 30 mg, about 5 mg to about 25 mg, about 5 mg to about 20 mg, about 5 mg to about 15 mg, or about 5 mg to about 10 mg per day. In some aspects, the therapeutically effective amount of Compound B, or a pharmaceutically acceptable salt form thereof, is about 10 mg to about 35 mg, about 10 mg to about 30 mg, about 10 mg to about 25 mg, about 10 mg to about 20 mg, or about 10 mg to about 15 mg per day. In some aspects, the therapeutically effective amount of Compound B, or a pharmaceutically acceptable salt form thereof, is about 15 mg to about 40 mg, about 15 mg to about 35 mg, about 15 mg to about 30 mg, about 15 mg to about 25 mg, or about 15 mg to about 20 mg per day. In some aspects, the therapeutically effective amount of Compound B, or a pharmaceutically acceptable salt form thereof, is about 20 mg to about 40 mg, about 20 mg to about 35 mg, about 20 mg to about 30 mg, or about 20 mg to about 25 mg per day. In some aspects, the therapeutically effective amount of Compound B, or a pharmaceutically acceptable salt form thereof, is about 25 mg to about 40 mg, about 25 mg to about 35 mg, or about 25 mg to about 30 mg per day. In some aspects, the therapeutically effective amount of Compound B, or a pharmaceutically acceptable salt form thereof, is about 2 mg, about 3 mg, about 4 mg, about 5 mg, about 6 mg, about 7 mg, about 8 mg, about 10 mg, about 11 mg, about 12 mg, about 13 mg, about 14 mg, about 15 mg, about 16 mg, about 17 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, or about 40 per day.

In some aspects, the therapeutically effective amount of Compound A is about 1 mg per day and the therapeutically effective amount of Compound B, or a pharmaceutically acceptable salt form thereof, is about 5 mg to about 15 mg per day.

In some aspects, the therapeutically effective amount of Compound A is about 2 mg per day and the therapeutically effective amount of Compound B, or a pharmaceutically acceptable salt form thereof, is about 5 mg to about 40 mg per day. In some aspects, the therapeutically effective amount of Compound A is about 2 mg per day and the therapeutically effective amount of Compound B, or a pharmaceutically acceptable salt form thereof, is about 20 mg to about 35 mg per day.

In some aspects, the therapeutically effective amount of Compound A is about 3 mg per day and the therapeutically effective amount of Compound B, or a pharmaceutically acceptable salt form thereof, is about 5 mg to about 40 mg per day. In some aspects, the therapeutically effective amount of Compound A is about 3 mg per day and the therapeutically effective amount of Compound B, or a pharmaceutically acceptable salt form thereof, is about 20 mg to about 35 mg per day.

In some aspects, the therapeutically effective amount of Compound A is about 4 mg per day and the therapeutically effective amount of Compound B, or a pharmaceutically acceptable salt form thereof, is about 10 mg to about 40 mg per day. In some aspects, the therapeutically effective amount of Compound A is about 4 mg per day and the therapeutically effective amount of Compound B, or a pharmaceutically acceptable salt form thereof, is about 20 mg to about 35 mg per day.

In some aspects, the therapeutically effective amount of Compound A is about 5 mg per day and the therapeutically effective amount of Compound B, or a pharmaceutically acceptable salt form thereof, is about 10 mg to about 40 mg per day. In some aspects, the therapeutically effective amount of Compound A is about 5 mg per day and the therapeutically effective amount of Compound B, or a pharmaceutically acceptable salt form thereof, is about 20 mg to about 40 mg per day.

In some aspects, the therapeutically effective amount of Compound A, or a pharmaceutically acceptable salt thereof, is about 1 mg per day and the therapeutically effective amount of Compound B, or a pharmaceutically acceptable salt form thereof, is about 20 mg per day. In some aspects, the therapeutically effective amount of Compound A, or a pharmaceutically acceptable salt thereof, is about 2 mg per day and the therapeutically effective amount of Compound B, or a pharmaceutically acceptable salt form thereof, is about 15 mg per day, In some aspects, the therapeutically effective amount of Compound A, or a pharmaceutically acceptable salt thereof, is about 2 mg per day and the therapeutically effective amount of Compound B, or a pharmaceutically acceptable salt form thereof, is about 20 mg per day. In some aspects, the therapeutically effective amount of Compound A, or a pharmaceutically acceptable salt thereof, is about 3 mg per day and the therapeutically effective amount of Compound B, or a pharmaceutically acceptable salt form thereof, is about 20 mg per day. In some aspects, the therapeutically effective amount of Compound A, or a pharmaceutically acceptable salt thereof, is about 2 mg per day and the therapeutically effective amount of Compound B, or a pharmaceutically acceptable salt form thereof, is about 15 mg per day. In some aspects, the therapeutically effective amount of Compound A, or a pharmaceutically acceptable salt thereof, is about 3 mg per day and the therapeutically effective amount of Compound B, or a pharmaceutically acceptable salt form thereof, is about 20 mg per day. In some aspects, the therapeutically effective amount of Compound A, or a pharmaceutically acceptable salt thereof, is about 3 mg per day and the therapeutically effective amount of Compound B, or a pharmaceutically acceptable salt form thereof, is about 15 mg per day. In some aspects, the therapeutically effective amount of Compound A, or a pharmaceutically acceptable salt thereof, is about 4 mg per day and the therapeutically effective amount of Compound B, or a pharmaceutically acceptable salt form thereof, is about 20 mg per day. In some aspects, the therapeutically effective amount of Compound A, or a pharmaceutically acceptable salt thereof, is about 4 mg per day and the therapeutically effective amount of Compound B, or a pharmaceutically acceptable salt form thereof, is about 15 mg per day. In some aspects, the therapeutically effective amount of Compound A, or a pharmaceutically acceptable salt thereof, is about 4 mg per day and the therapeutically effective amount of Compound B, or a pharmaceutically acceptable salt form thereof, is about 5 mg per day. In some aspects, the therapeutically effective amount of Compound A, or a pharmaceutically acceptable salt thereof, is about 4 mg per day and the therapeutically effective amount of Compound B, or a pharmaceutically acceptable salt form thereof, is about 10 mg per day. In some aspects, the therapeutically effective amount of Compound A, or a pharmaceutically acceptable salt thereof, is about 8 mg per day and the therapeutically effective amount of Compound B, or a pharmaceutically acceptable salt form thereof, is about 5 mg per day. In some aspects, the therapeutically effective amount of Compound A, or a pharmaceutically acceptable salt thereof, is about 8 mg per day and the therapeutically effective amount of Compound B, or a pharmaceutically acceptable salt form thereof, is about 10 mg per day. In some aspects, the therapeutically effective amount of Compound A, or a pharmaceutically acceptable salt thereof, is about 12 mg per day and the therapeutically effective amount of Compound B, or a pharmaceutically acceptable salt form thereof, is about 5 mg per day. In some aspects, the therapeutically effective amount of Compound A, or a pharmaceutically acceptable salt thereof, is about 12 mg per day and the therapeutically effective amount of Compound B, or a pharmaceutically acceptable salt form thereof, is about 10 mg per day.

In some aspects, Compound B is a pharmaceutically acceptable salt form. In some aspects, the pharmaceutically acceptable salt form is a maleate salt. In some aspects, the maleate salt is a sesqui-maleate salt.

In some aspects, the therapeutically effective amount of the maleate salt form of Compound B is about 5 mg to about 35 mg per day. In some aspects, the therapeutically effective amount of the maleate salt form of Compound B is about 5 mg to about 30 mg, about 5 mg to about 25 mg, about 5 mg to about 20 mg, about 5 mg to about 15 mg, or about 5 mg to about 10 mg per day. In some aspects, the therapeutically effective amount of the maleate salt form of Compound B is about 10 mg to about 30 mg, about 10 mg to about 25 mg, about 10 mg to about 20 mg, or about 10 mg to about 15 mg per day. In some aspects, the therapeutically effective amount of the maleate salt form of Compound B is about 15 mg to about 30 mg, about 15 mg to about 25 mg, or about 15 mg to about 20 mg per day. In some aspects, the therapeutically effective amount of the maleate salt form of Compound B is about 20 mg to about 30 mg or about 20 mg to about 25 mg per day. In some aspects, the therapeutically effective amount of the maleate salt form of Compound B is about 25 mg to about 30 mg per day. In some aspects, the therapeutically effective amount of the maleate salt form of Compound B is about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, or about 35 mg.

In some aspects, the therapeutically effective amount of Compound A is about 1 mg per day and the therapeutically effective amount of Compound B as a maleate salt is about 5 mg to about 10 mg per day. In some aspects, the therapeutically effective amount of Compound A is about 1 mg per day and the therapeutically effective amount of Compound B as a maleate salt is about 7 mg per day.

In some aspects, the therapeutically effective amount of Compound A is about 2 mg per day and the therapeutically effective amount of Compound B as a maleate salt is about 10 mg to about 30 mg per day. In some aspects, the therapeutically effective amount of Compound A is about 2 mg per day and the therapeutically effective amount of Compound B as a maleate salt is about 13 mg per day. In some aspects, the therapeutically effective amount of Compound A is about 2 mg per day and the therapeutically effective amount of Compound B as a maleate salt is about 27 mg per day.

In some aspects, the therapeutically effective amount of Compound A is about 3 mg per day and the therapeutically effective amount of Compound B as a maleate salt is about 15 mg to about 40 mg per day. In some aspects, the therapeutically effective amount of Compound A is about 3 mg per day and the therapeutically effective amount of Compound B as a maleate salt is about 20 mg per day. In some aspects, the therapeutically effective amount of Compound A is about 3 mg per day and the therapeutically effective amount of Compound B as a maleate salt is about 34 mg per day.

In some aspects, the therapeutically effective amount of Compound A is about 4 mg per day and the therapeutically effective amount of Compound B as a maleate salt is about 20 mg to about 40 mg per day. In some aspects, the therapeutically effective amount of Compound A is about 4 mg per day and the therapeutically effective amount of Compound B as a maleate salt is about 27 mg per day.

In some aspects, the therapeutically effective amount of Compound A is about 5 mg per day and the therapeutically effective amount of Compound B as a maleate salt is about 25 mg to about 40 mg per day. In some aspects, the therapeutically effective amount of Compound A is about 5 mg per day and the therapeutically effective amount of Compound B as a maleate salt is about 34 mg per day.

In some aspects, the therapeutically effective amount of Compound A, or a pharmaceutically acceptable salt thereof, is about 1 mg per day and the therapeutically effective amount of Compound B, as a maleate salt, which can be a sesqui-maleate salt, is about 27 mg per day. In some aspects, the therapeutically effective amount of Compound A, or a pharmaceutically acceptable salt thereof, is about 2 mg per day and the therapeutically effective amount of Compound B, as a maleate salt, which can be a sesqui-maleate salt, is about 20 mg per day, In some aspects, the therapeutically effective amount of Compound A, or a pharmaceutically acceptable salt thereof, is about 2 mg per day and the therapeutically effective amount of Compound B, as a maleate salt, which can be a sesqui-maleate salt, is about 27 mg per day. In some aspects, the therapeutically effective amount of Compound A, or a pharmaceutically acceptable salt thereof, is about 3 mg per day and the therapeutically effective amount of Compound B, as a maleate salt, which can be a sesqui-maleate salt, is about 27 mg per day. In some aspects, the therapeutically effective amount of Compound A, or a pharmaceutically acceptable salt thereof, is about 2 mg per day and the therapeutically effective amount of Compound B, as a maleate salt, which can be a sesqui-maleate salt, is about 20 mg per day. In some aspects, the therapeutically effective amount of Compound A, or a pharmaceutically acceptable salt thereof, is about 3 mg per day and the therapeutically effective amount of Compound B, as a maleate salt, which can be a sesqui-maleate salt, is about 27 mg per day. In some aspects, the therapeutically effective amount of Compound A, or a pharmaceutically acceptable salt thereof, is about 3 mg per day and the therapeutically effective amount of Compound B, as a maleate salt, which can be a sesqui-maleate salt, is about 20 mg per day. In some aspects, the therapeutically effective amount of Compound A, or a pharmaceutically acceptable salt thereof, is about 4 mg per day and the therapeutically effective amount of Compound B, as a maleate salt, which can be a sesqui-maleate salt, is about 27 mg per day. In some aspects, the therapeutically effective amount of Compound A, or a pharmaceutically acceptable salt thereof, is about 4 mg per day and the therapeutically effective amount of Compound B, as a maleate salt, which can be a sesqui-maleate salt, is about 20 mg per day. In some aspects, the therapeutically effective amount of Compound A, or a pharmaceutically acceptable salt thereof, is about 4 mg per day and the therapeutically effective amount of Compound B, as a maleate salt, which can be a sesqui-maleate salt, is about 7 mg per day. In some aspects, the therapeutically effective amount of Compound A, or a pharmaceutically acceptable salt thereof, is about 4 mg per day and the therapeutically effective amount of Compound B, or a pharmaceutically acceptable salt form thereof, is about 13 mg per day. In some aspects, the therapeutically effective amount of Compound A, or a pharmaceutically acceptable salt thereof, is about 8 mg per day and the therapeutically effective amount of Compound B, or a pharmaceutically acceptable salt form thereof, is about 7 mg per day. In some aspects, the therapeutically effective amount of Compound A, or a pharmaceutically acceptable salt thereof, is about 8 mg per day and the therapeutically effective amount of Compound B, or a pharmaceutically acceptable salt form thereof, is about 13 mg per day. In some aspects, the therapeutically effective amount of Compound A, or a pharmaceutically acceptable salt thereof, is about 12 mg per day and the therapeutically effective amount of Compound B, or a pharmaceutically acceptable salt form thereof, is about 7 mg per day. In some aspects, the therapeutically effective amount of Compound A, or a pharmaceutically acceptable salt thereof, is about 12 mg per day and the therapeutically effective amount of Compound B, or a pharmaceutically acceptable salt form thereof, is about 13 mg per day.

In some aspects, Compound A, or a pharmaceutically acceptable salt form thereof is administered once per day. In some aspects, Compound B, or a pharmaceutically acceptable salt form thereof, is administered once per day.

In some aspects, Compound A or a pharmaceutically acceptable salt form thereof, and Compound B or a pharmaceutically acceptable salt form thereof, are administered in the same or different dosage forms. In some aspects, Compound A or a pharmaceutically acceptable salt form thereof, and Compound B or a pharmaceutically acceptable salt form thereof, are administered in different dosage forms. In some aspects, Compound A or a pharmaceutically acceptable salt form thereof, is administered before, concomitantly, or subsequently to the administering of Compound B or a pharmaceutically acceptable salt form thereof.

In some aspects, Compound A or a pharmaceutically acceptable salt form thereof, and Compound B or a pharmaceutically acceptable salt form thereof, are administered in the same dosage form. In some aspects, Compound A or a pharmaceutically acceptable salt form thereof, and Compound B or a pharmaceutically acceptable salt form thereof, are administered orally. In some aspects, the dosage form comprising Compound A or a pharmaceutically acceptable salt form thereof, and Compound B or a pharmaceutically acceptable salt form thereof, is a capsule.

In some aspects, the present disclosure provides a pharmaceutical composition comprising:

a. Compound A, or a pharmaceutically acceptable salt form thereof;
b. Compound B, or a pharmaceutically acceptable salt form thereof;
c. a filler;
d. a disintegrant; and
e. a lubricant.

In some aspects, the pharmaceutical composition comprises about 0.8 mg to about 1.2 mg of Compound A. In some aspects, the pharmaceutical composition comprises about 1.5 mg to about 2.5 mg of Compound A. In some aspects, the pharmaceutical composition comprises about 0.8 mg, about 0.9 mg, about 1 mg, about 1.1 mg, about 1.2 mg, about 1.3 mg, about 1.4 mg, about 1.5 mg, about 1.6 mg, about 1.7 mg, about 1.8 mg, about 1.9 mg, about 2 mg, about 2.1 mg, about 2.2 mg, about 2.3 mg, about 2.4 mg, or about 2.5 mg of Compound A.

In some aspects, the pharmaceutical composition comprises about 20 mg to about 35 mg of the maleic acid salt of Compound B. In some aspects, the pharmaceutical composition comprises about 22 to about 34 mg of the maleic acid salt of Compound B. In some aspects, the pharmaceutical composition comprises about 23 mg to about 29 mg of the maleic acid salt of Compound B. In some aspects, the pharmaceutical composition comprises about 25 mg to about 28 mg of the maleic acid salt of Compound B. In some aspects, the pharmaceutical composition comprises 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, or about 35 mg of the maleic acid salt of Compound B.

In some aspects, the pharmaceutical composition comprises a filler. In some aspects, the pharmaceutical composition comprises about 70 wt/wt % to about 90 wt/wt % filler. In some aspects, the pharmaceutical composition comprises about 72.5 wt/wt % to about 85 wt/wt % filler. In some aspects, the pharmaceutical composition comprises about 80 wt/wt % to about 90 wt/wt % filler. In some aspects, the pharmaceutical composition comprises about 70 wt/wt %, about 72.5 wt/wt %, about 75 wt/wt %, about 80 wt/wt %, about 85 wt/wt %, or about 90 wt/wt % filler.

In some aspects, the filler is selected from a group consisting of microcrystalline cellulose, lactose, mannitol, starch, dibasic calcium phosphate, and combinations thereof. In some aspects, the filler comprises microcrystalline cellulose. In some aspects, the microcrystalline cellulose is silicified microcrystalline cellulose. In some aspects, the pharmaceutical composition comprises about 70 wt/wt % to about 90 wt/wt % silicified microcrystalline cellulose. In some aspects, the pharmaceutical composition comprises about 72.5 wt/wt % to about 85 wt/wt % silicified microcrystalline cellulose. In some aspects, the pharmaceutical composition comprises about 80 wt/wt % to about 90 wt/wt % silicified microcrystalline cellulose. In some aspects, the pharmaceutical composition comprises about 70 wt/wt %, about 72.5 wt/wt %, about 75 wt/wt %, about 80 wt/wt %, about 85 wt/wt %, or about 90 wt/wt % silicified microcrystalline cellulose.

In some aspects, the pharmaceutical composition comprises about 3.5 wt/wt % to about 4.5 wt/wt % disintegrant. In some aspects, the pharmaceutical composition comprises about 3.5 wt/wt %, about 4.6 wt/wt %, about 3.7 wt/wt %, about 3.8 wt/wt %, about 3.9 wt/wt %, about 4 wt/wt %, about 4.1 wt/wt %, about 4.2 wt/wt %, about 4.3 wt/wt %, about 4.4 wt/wt %, or about 4.5 wt/wt % disintegrant.

In some aspects, the disintegrant sis selected from the group consisting of croscarmellose sodium, sodium starch glycolate, crospovidone, alginic acid, and combinations thereof. In some aspects, the disintegrant comprises croscarmellose sodium. In some aspects, the pharmaceutical composition comprises about 3.5 wt/wt % to about 4.5 wt/wt % croscarmellose sodium. In some aspects, the pharmaceutical composition comprises about 3.5 wt/wt %, about 4.6 wt/wt %, about 3.7 wt/wt %, about 3.8 wt/wt %, about 3.9 wt/wt %, about 4 wt/wt %, about 4.1 wt/wt %, about 4.2 wt/wt %, about 4.3 wt/wt %, about 4.4 wt/wt %, or about 4.5 wt/wt % croscarmellose sodium.

In some aspects, the pharmaceutical composition comprises about 1.5 wt/wt % to about 5 wt/wt % lubricant. In some aspects, the pharmaceutical composition comprises about 1.5 wt/wt %, about 2 wt/wt %, about 2.5 wt/wt %, about 3 wt/wt %, about 3.5 wt/wt %, about 4 wt/wt %, about 4.5 wt/wt %, or about 5 wt/wt % lubricant.

In some aspects, the lubricant is selected from the group consisting of sodium stearyl fumarate, magnesium stearate, glyceryl dibehenat, talc, and combinations thereof. In some aspects, the lubricant comprises sodium stearyl fumarate or magnesium stearate. In some aspects, the pharmaceutical composition comprises about 1.5 wt/wt %, about 2 wt/wt %, about 2.5 wt/wt %, about 3 wt/wt %, about 3.5 wt/wt %, about 4 wt/wt %, about 4.5 wt/wt %, or about 5 wt/wt % sodium stearyl fumarate. In some aspects, the pharmaceutical composition comprises about 1.5 wt/wt %, about 2 wt/wt %, about 2.5 wt/wt %, about 3 wt/wt %, about 3.5 wt/wt %, about 4 wt/wt %, about 4.5 wt/wt %, or about 5 wt/wt % magnesium stearate.

In some aspects, the pharmaceutical composition to be orally administered. In some aspects, the pharmaceutical composition is a tablet or capsule. In some aspects, the pharmaceutical composition is a capsule.

In some aspects, the capsule comprises about 1 mg of Compound A and about 7 mg of the maleic acid salt of Compound B, wherein each component of the capsule is as follows:

a. about 0.8 wt/wt % to about 1.2 wt/wt % of Compound A;
b. about 6 wt/wt % to about 8 wt/wt % of the maleic acid salt of Compound B;
c. about 80 wt/wt % to about 90 wt/wt % of silicified microcrystalline cellulose;
d. about 3.5 wt/wt % to about 4.5 wt/wt % of croscarmellose sodium;
e. about 1.5 wt/wt % to about 5.0 wt/wt % of sodium stearyl fumarate; and
f. a gelatin capsule which encapsulates components a-e.

In some aspects, the capsule comprises about 2 mg of Compound A and about 27 mg of the maleic acid salt of Compound B, wherein each component of the capsule is as follows:

a. about 0.8 wt/wt % to about 1.3 wt/wt % of Compound A;
b. about 12.3 wt/wt % to about 15.0 wt/wt % of the maleic acid salt of Compound B;
c. about 72.5 wt/wt % to about 85 wt/wt % of silicified microcrystalline cellulose;
d. about 3.5 wt/wt % to about 4.5 wt/wt % of croscarmellose sodium;
e. about 1.5 wt/wt % to about 5.0 wt/wt % of sodium stearyl fumarate; and
f. a gelatin capsule which encapsulates components a-e.

In some aspects, Compound A or a pharmaceutically acceptable salt form thereof, and Compound B or a pharmaceutically acceptable salt form thereof, are administered to treat a patient having a solid tumor. In some aspects, the solid tumor is selected from the group consisting of malignant peripheral nerve sheath tumor, biliary tract cancer, breast cancer, cholangiocarcinoma, urothelial cancer, uterine neoplasm, lung adenocarcinoma, squamous non-small cell lung cancer, non-squamous non-small cell lung cancer, gastric cancer, sarcoma, bladder cancer, head and neck cancer, small cell lung cancer, endometrial cancer, esophageal cancer, adenoid cystic carcinoma, gallbladder cancer, colorectal cancer, thyroid cancer, hepatocellular cancer, prostate cancer, oral cancer, cervical cancer, pancreatic carcinoma, ovarian cancer, melanoma, and serous carcinoma to the peritoneum. In some aspects, the patient has non-small cell lung cancer. In some aspects, the patient has endometrial cancer. In some aspects, the patient has ovarian cancer. In some aspects, the patient has low grade serous ovarian cancer. In some aspects, the patient has a confirmed mutation in one or more of KRAS, NRAS, HRAS, BRAF, NF1, MEK1, and MEK2. In some aspects, the patient has a confirmed mutation in RASA1 and/or RAF1.

In some aspects, Compound A or a pharmaceutically acceptable salt form thereof, and Compound B or a pharmaceutically acceptable salt form thereof, are administered on a 28-day dosing cycle comprising: (a) 21 days in which Compound A or a pharmaceutically acceptable salt form thereof, and Compound B or a pharmaceutically acceptable salt form thereof, are both administered; and (b) 7 days in which neither Compound A or a pharmaceutically acceptable salt form thereof, nor Compound B or a pharmaceutically acceptable salt form thereof, is administered. In some aspects, Compound A or a pharmaceutically acceptable salt form thereof, and Compound B or a pharmaceutically acceptable salt form thereof, are administered on a 28-day dosing cycle comprising (a) 21 days in which Compound A or a pharmaceutically acceptable salt form thereof, and Compound B or a pharmaceutically acceptable salt form thereof are both administered; followed by (b) 7 days in which neither Compound A or a pharmaceutically acceptable salt form thereof, nor Compound B or a pharmaceutically acceptable salt form thereof, is administered. In some aspects, Compound A or a pharmaceutically acceptable salt form thereof, and Compound B or a pharmaceutically acceptable salt form thereof, are administered on a 28-day dosing cycle comprising (a) three 7-day periods each comprising (i) 5 days in which Compound A or a pharmaceutically acceptable salt form thereof, and Compound B or a pharmaceutically acceptable salt form thereof, are both administered and (ii) 2 days in which neither Compound A or a pharmaceutically acceptable salt form thereof, nor Compound B or a pharmaceutically acceptable salt form thereof are administered; and (b) 7 days in which neither Compound A or a pharmaceutically acceptable salt form thereof, nor Compound B or a pharmaceutically acceptable salt form thereof, is administered. In some aspects, Compound A or a pharmaceutically acceptable salt form thereof, and Compound B or a pharmaceutically acceptable salt form thereof, are administered on a 28-day dosing cycle comprising (a) three 7-day periods each comprising (i) 5 days in which Compound A or a pharmaceutically acceptable salt form thereof, and Compound B or a pharmaceutically acceptable salt form thereof, are both administered and (ii) 2 days in which neither Compound A or a pharmaceutically acceptable salt form thereof, nor Compound B or a pharmaceutically acceptable salt form thereof, is administered; followed by (b) 7 days in which neither Compound A or a pharmaceutically acceptable salt form thereof, nor Compound B or a pharmaceutically acceptable salt form thereof, is administered. In some aspects, Compound A or a pharmaceutically acceptable salt form thereof, and Compound B or a pharmaceutically acceptable salt form thereof, are administered on a 28-day dosing cycle comprising (a) three 7-day periods each comprising (i) 4 days in which Compound A or a pharmaceutically acceptable salt form thereof, and Compound B or a pharmaceutically acceptable salt form thereof, are both administered and (ii) 3 days in which neither Compound A or a pharmaceutically acceptable salt form thereof, nor Compound B or a pharmaceutically acceptable salt form thereof are administered; and (b) 7 days in which neither Compound A or a pharmaceutically acceptable salt form thereof, nor Compound B or a pharmaceutically acceptable salt form thereof, is administered. In some aspects, Compound A or a pharmaceutically acceptable salt form thereof, and Compound B or a pharmaceutically acceptable salt form thereof, are administered on a 28-day dosing cycle comprising (a) three 7-day periods each comprising (i) 4 days in which Compound A or a pharmaceutically acceptable salt form thereof, and Compound B or a pharmaceutically acceptable salt form thereof, are both administered and (ii) 3 days in which neither Compound A or a pharmaceutically acceptable salt form thereof, nor Compound B or a pharmaceutically acceptable salt form thereof, is administered; followed by (b) 7 days in which neither Compound A or a pharmaceutically acceptable salt form thereof, nor Compound B or a pharmaceutically acceptable salt form thereof, is administered.

In some aspects, the pharmaceutical composition comprising Compound A or a pharmaceutically acceptable salt form thereof, and Compound B or a pharmaceutically acceptable salt form thereof, is administered on a 28-day dosing cycle comprising: (a) 21 days in which the pharmaceutical composition comprising Compound A or a pharmaceutically acceptable salt form thereof, and Compound B or a pharmaceutically acceptable salt form thereof form, is administered; and (b) 7 days in which the pharmaceutical composition comprising Compound A or a pharmaceutically acceptable salt form thereof, and Compound B or a pharmaceutically acceptable salt form thereof, is not administered. In some aspects, the pharmaceutical composition comprising Compound A or a pharmaceutically acceptable salt form thereof, and Compound B or a pharmaceutically acceptable salt form thereof, is administered on a 28-day dosing cycle comprising (a) 21 days in which the pharmaceutical composition comprising Compound A or a pharmaceutically acceptable salt form thereof, and Compound B or a pharmaceutically acceptable salt form thereof, is administered; followed by (b) 7 days in which the pharmaceutical composition comprising Compound A or a pharmaceutically acceptable salt form thereof, and Compound B or a pharmaceutically acceptable salt form thereof is not administered. In some aspects, the pharmaceutical composition comprising Compound A or a pharmaceutically acceptable salt form thereof, and Compound B or a pharmaceutically acceptable salt form of thereof, is administered on a 28-day dosing cycle comprising (a) three 7-day periods each comprising (i) 5 days in which the pharmaceutical composition comprising Compound A or a pharmaceutically acceptable salt form thereof, and Compound B or a pharmaceutically acceptable salt form of thereof is administered and (ii) 2 days in which the pharmaceutical composition comprising Compound A or a pharmaceutically acceptable salt form thereof, and Compound B or a pharmaceutically acceptable salt form of thereof, is not administered; and (b) 7 days in which the pharmaceutical composition comprising Compound A or a pharmaceutically acceptable salt form thereof, and Compound B or a pharmaceutically acceptable salt form thereof, is not administered. In some aspects, the pharmaceutical composition comprising Compound A or a pharmaceutically acceptable salt form thereof, and Compound B or a pharmaceutically acceptable salt form thereof, is administered on a 28-day dosing cycle comprising (a) three 7-day periods each comprising (i) 5 days in which the pharmaceutical composition comprising Compound A or a pharmaceutically acceptable salt form thereof, and Compound B or a pharmaceutically acceptable salt form thereof, is administered and (ii) 2 days in which the pharmaceutical composition comprising Compound A or a pharmaceutically acceptable salt form thereof, and Compound B or a pharmaceutically acceptable salt form thereof, is not administered; followed by (b) 7 days in which the pharmaceutical composition comprising Compound A or a pharmaceutically acceptable salt form thereof, and Compound B or a pharmaceutically acceptable salt form thereof, is not administered. In some aspects, the pharmaceutical composition comprising Compound A or a pharmaceutically acceptable salt form thereof, and Compound B or a pharmaceutically acceptable salt form thereof, is administered on a 28-day dosing cycle comprising (a) three 7-day periods each comprising (i) 4 days in which the pharmaceutical composition comprising Compound A or a pharmaceutically acceptable salt form thereof, and Compound B or a pharmaceutically acceptable salt form thereof, is administered and (ii) 3 days in which the pharmaceutical composition comprising Compound A or a pharmaceutically acceptable salt form thereof, and Compound B or a pharmaceutically acceptable salt form thereof, is administered; and (b) 7 days in which the pharmaceutical composition comprising Compound A or a pharmaceutically acceptable salt form thereof, and Compound B or a pharmaceutically acceptable salt form of thereof, is not administered. In some aspects, the pharmaceutical composition comprising Compound A or a pharmaceutically acceptable salt form thereof, and Compound B or a pharmaceutically acceptable salt form of thereof, is administered on a 28-day dosing cycle comprising (a) three 7-day periods each comprising (i) 4 days in which the pharmaceutical composition comprising Compound A or a pharmaceutically acceptable salt form thereof, and Compound B or a pharmaceutically acceptable salt form of thereof, is administered and (ii) 3 days in which the pharmaceutical composition comprising Compound A or a pharmaceutically acceptable salt form thereof, and Compound B or a pharmaceutically acceptable salt form thereof, is not administered; followed by (b) 7 days in which the pharmaceutical composition comprising Compound A or a pharmaceutically acceptable salt form thereof, and Compound B or a pharmaceutically acceptable salt form thereof, is not administered.

In some aspects, the 28-day dosing cycle is repeated up to a total of 24 consecutive 28-day dosing cycles.

In some aspects, only Compound B, or a pharmaceutically acceptable salt form thereof, is administered for a lead-in period prior to the first of the 28-day dosing cycles discussed above. In some aspects, the amount of Compound B, or a pharmaceutically acceptable salt thereof, administered in the lead-in period is the same or lower than the amount of Compound B, or a pharmaceutically acceptable salt thereof, administered during the first of the 28-day dosing cycles discussed above.

In some aspects, one or both of Compound A, or a pharmaceutically acceptable salt form thereof, and Compound B, or a pharmaceutically acceptable salt form thereof, is administered for a lead-in period prior to the first of the 28-day dosing cycles discussed above at a lower dose than the therapeutically effective amount of Compound A, or a pharmaceutically acceptable salt form thereof, and Compound B, or a pharmaceutically acceptable salt thereof, administered during the first of the 28-day dosing cycles discussed above. In some aspects, the amount of Compound A, or a pharmaceutically acceptable salt thereof, administered in the lead-in period is the same as the amount of Compound A, or a pharmaceutically acceptable salt thereof, administered during the first of the 28-day dosing cycles discussed above. In some aspects, the amount of Compound A, or a pharmaceutically acceptable salt thereof, administered in the lead-in period is lower than the amount of Compound A, or a pharmaceutically acceptable salt thereof, administered during the first of the 28-day dosing cycles discussed above. In some aspects, the amount of Compound B, or a pharmaceutically acceptable salt thereof, administered in the lead-in period is the same as the amount of Compound B, or a pharmaceutically acceptable salt thereof, administered during the first of the 28-day dosing cycles discussed above. In some aspects, the amount of Compound B, or a pharmaceutically acceptable salt thereof, administered in the lead-in period is lower than the amount of Compound B, or a pharmaceutically acceptable salt thereof, administered during the first of the 28-day dosing cycles discussed above.

In some aspects, the amount of Compound A, or a pharmaceutically acceptable salt thereof, administered in the lead-in period is about 1 mg to about 5 mg per day. In some aspects, the amount of Compound A, or a pharmaceutically acceptable salt thereof, administered in the lead-in period about 1 mg per day. In some aspects, the amount of Compound A, or a pharmaceutically acceptable salt thereof, administered in the lead-in period about 2 mg per day. In some aspects, the amount of Compound A, or a pharmaceutically acceptable salt thereof, administered in the lead-in period about 3 mg per day.

In some aspects, the amount of Compound B, or a pharmaceutically acceptable salt thereof, administered in the lead-in period is about 5 mg to about 25 mg per day. In some aspects, the amount of Compound B, or a pharmaceutically acceptable salt thereof, administered in the lead-in period is about 5 mg to about 20 mg per day. In some aspects, the amount of Compound B, or a pharmaceutically acceptable salt thereof, administered in the lead-in period is about 5 mg to about 15 mg per day. In some aspects, the amount of Compound B, or a pharmaceutically acceptable salt thereof, administered in the lead-in period is about 5 mg per day. In some aspects, the amount of Compound B, or a pharmaceutically acceptable salt thereof, administered in the lead-in period is about 10 mg per day. In some aspects, the amount of Compound B, or a pharmaceutically acceptable salt thereof, administered in the lead-in period is about 15 mg per day. In some aspects, the amount of Compound B, or a pharmaceutically acceptable salt thereof, administered in the lead-in period is about 20 mg per day.

In some aspects, the Compound B administered in the lead-in period is a pharmaceutically acceptable salt form. In some aspects, the pharmaceutically acceptable salt form is a maleate salt, which can be a sesqui-maleate salt. In some aspects, the amount of Compound B as a maleate salt, which can be a sesqui-maleate salt, administered in the lead-in period is about 5 mg to about 40 mg per day. In some aspects, the amount of Compound B as a maleate salt, which can be a sesqui-maleate salt, administered in the lead-in period is about 5 mg to about 30 mg per day. In some aspects, the amount of Compound B as a maleate salt, which can be a sesqui-maleate salt, administered in the lead-in period is about 5 mg to about 25 mg per day. In some aspects, the amount of Compound B as a maleate salt, which can be a sesqui-maleate salt, administered in the lead-in period is about 7 mg per day. In some aspects, the amount of Compound B as a maleate salt, which can be a sesqui-maleate salt, administered in the lead-in period is about 13 mg per day. In some aspects, the amount of Compound B as a maleate salt, which can be a sesqui-maleate salt, administered in the lead-in period is about 20 mg per day. In some aspects, the amount of Compound B as a maleate salt, which can be a sesqui-maleate salt, administered in the lead-in period is about 27 mg per day.

In some aspects, the Compound A, or a pharmaceutically acceptable salt thereof, and/or the Compound B, or a pharmaceutically acceptable salt thereof, is administered daily during the lead-in period. In some aspects, the Compound A, or a pharmaceutically acceptable salt thereof, and/or Compound B, or a pharmaceutically acceptable salt thereof, is administered once daily during the lead-in period. In some aspects, Compound A, or pharmaceutically acceptable salt thereof, and Compound B, or a pharmaceutically acceptable salt form thereof, are administered orally during the lead-in period.

In some aspects, the Compound A, or a pharmaceutically acceptable salt thereof, and Compound B, or a pharmaceutically acceptable salt form thereof, are administered in the same or different dosage forms during the lead-in period. In some aspects, the Compound A, or a pharmaceutically acceptable salt thereof, and Compound B, or a pharmaceutically acceptable salt form thereof, are administered in the same dosage form during the lead-in period. In some aspects, the dosage form is a capsule.

In some aspects, Compound A, or a pharmaceutically acceptable salt thereof, and Compound B, or a pharmaceutically acceptable salt form thereof, are administered in different dosage forms during the lead-in period. In some aspects, Compound A is administered before, concomitantly, or subsequently to the administering of Compound B, or a pharmaceutically acceptable salt form thereof during the lead-in period. In some aspects, the dosage form of Compound A, or a pharmaceutically acceptable salt thereof, is a capsule. In some aspects, he dosage form of Compound B, or a pharmaceutically acceptable salt form thereof, is a capsule In some aspects, the lead-in period begins 21 days before the first 28-day dosing cycle. In some aspects, the lead-in period begins 14 days before the first 28-day dosing cycle. In some aspects, the lead-in period begins 10 days before the first 28-day dosing cycle. In some aspects, the lead-in period begins 7 days before the first 28-day dosing cycle.

In some aspects, methods of treating a patient having a solid tumor comprising administering once daily 2 mg Compound A as free base and 15 mg Compound B, or a pharmaceutically acceptable salt thereof, are described herein. In some aspects, Compound B is administered as a pharmaceutically acceptable salt form. In some aspects, the pharmaceutically acceptable salt form is a maleate salt, which can be a sesqui-maleate salt. In some aspects, the amount of Compound B as a maleate salt, which can be a sesqui-maleate salt, is about 20 mg.

In some aspects, methods of treating a patient having a solid tumor comprising administering once daily 2 mg Compound A as free base and 20 mg Compound B, or a pharmaceutically acceptable salt thereof, are described herein. In some aspects, Compound B is administered as a pharmaceutically acceptable salt form. In some aspects, the pharmaceutically acceptable salt form is a maleate salt, which can be a sesqui-maleate salt. In some aspects, the amount of Compound B as a maleate salt, which can be a sesqui-maleate salt, is about 27 mg In some aspects, methods of treating a patient having a solid tumor comprising a 7 day cycle that comprises (a) administering once daily 3 mg of Compound A free base and 20 mg of Compound B, or a pharmaceutically acceptable salt form for 5 consecutive days; followed by (b) administering no Compound A or Compound B for 2 consecutive days, are described herein. In some aspects, the Compound B is administered as a pharmaceutically acceptable salt form. In some aspects, the pharmaceutically acceptable salt form is a maleate salt, which can be a sesqui-maleate salt. In some aspects, the amount of Compound B as a maleate salt, which can be a sesqui-maleate salt, is about 27 mg In some aspects, methods of treating a patient having a solid tumor comprising:

(a) a lead-in period that comprises administering once daily 3 mg Compound A free base and 10 mg Compound B, or a pharmaceutically acceptable salt form thereof, for 14 consecutive days; followed by (b) a 7 day treatment cycle that comprises (i) administering once daily 3 mg of Compound A free base and 20 mg of Compound B, or a pharmaceutically acceptable salt form therefore, for 5 consecutive days; followed by (ii) administering no Compound A or Compound B for 2 consecutive days, are described herein. In some aspects, the Compound B is administered in both the lead-in period and treatment cycle as a pharmaceutically acceptable salt form. In some aspects, the pharmaceutically acceptable salt form is a maleate salt, which can be a sesqui-maleate salt. In some aspects, the amount of Compound B as a maleate salt, which can be a sesqui-maleate salt, administered in the lead-in period is about 13 mg. In some aspects, the amount of Compound B as a maleate salt, which can be a sesqui-maleate salt, administered in the treatment period is about 27 mg In some aspects, methods of treating a patient having a solid tumor comprising:

(a) a lead-in period that comprises administering a total of 2 mg Compound A free base divided over two doses per day and 15 mg Compound B, or a pharmaceutically acceptable salt form thereof, once daily for 14 consecutive days; followed by (b) a 7 day treatment cycle that comprises (i) administering 1 mg of Compound A free base twice daily and 15 mg of Compound B, or a pharmaceutically acceptable salt form therefore, once daily for 5 consecutive days; followed by (ii) administering no Compound A or Compound B for 2 consecutive days are described herein. In some aspects, the Compound B is administered in both the lead-in period and treatment cycle as a pharmaceutically acceptable salt form. In some aspects, the pharmaceutically acceptable salt form is a maleate salt, which can be a sesqui-maleate salt. In some aspects, the amount of Compound B as a maleate salt, which can be a sesqui-maleate salt, administered in the lead-in period is about 13 mg. In some aspects, the amount of Compound B as a maleate salt, which can be a sesqui-maleate salt, administered in the treatment period is about 20 mg In some aspects, methods of treating a patient having a solid tumor comprising:

(a) a lead-in period that comprises administering 15 mg Compound B, or a pharmaceutically acceptable salt form thereof, once daily for 14 consecutive days; followed by (b) a 7 day treatment cycle that comprises (i) administering once daily 1 mg of Compound A free base and 20 mg of Compound B, or a pharmaceutically acceptable salt form therefore, once daily for 5 consecutive days; followed by (ii) administering no Compound A or Compound B for 2 consecutive days are described herein. In some aspects, the Compound B is administered in both the lead-in period and treatment cycle as a pharmaceutically acceptable salt form. In some aspects, the pharmaceutically acceptable salt form is a maleate salt, which can be a sesqui-maleate salt. In some aspects, the amount of Compound B as a maleate salt, which can be a sesqui-maleate salt, administered in the lead-in period is about 20 mg. In some aspects, the amount of Compound B as a maleate salt, which can be a sesqui-maleate salt, administered in the treatment period is about 27 mg In some aspects, methods of treating a patient having a solid tumor comprising:

(a) a lead-in period that comprises administering 15 mg Compound B, or a pharmaceutically acceptable salt form thereof, once daily for 14 consecutive days; followed by (b) a 7 day treatment cycle that comprises (i) administering once daily 2 mg of Compound A free base and 20 mg of Compound B, or a pharmaceutically acceptable salt form therefore, once daily for 5 consecutive days; followed by (ii) administering no Compound A or Compound B for 2 consecutive days are described herein. In some aspects, Compound B is administered in both the lead-in period and treatment cycle as a pharmaceutically acceptable salt form. In some aspects, the pharmaceutically acceptable salt form is a maleate salt, which can be a sesqui-maleate salt. In some aspects, the amount of Compound B as a maleate salt, which can be a sesqui-maleate salt, administered in the lead-in period is about 20 mg. In some aspects, the amount of Compound B as a maleate salt, which can be a sesqui-maleate salt, administered in the treatment period is about 27 mg.

In some aspects, methods of treating a patient having a solid tumor comprising a 7 day cycle that comprises (a) administering once daily 4 mg of Compound A free base and 20 mg of Compound B, or a pharmaceutically acceptable salt form for 5 consecutive days; followed by (b) administering no Compound A or Compound B for 2 consecutive days are described herein. In some aspects, the Compound B is administered as a pharmaceutically acceptable salt form. In some aspects, the pharmaceutically acceptable salt form is a maleate salt, which can be a sesqui-maleate salt. In some aspects, the amount of Compound B as a maleate salt, which can be a sesqui-maleate salt, is about 27 mg In some aspects, methods of treating a patient having a solid tumor comprising:

(a) a lead-in period that comprises administering 15 mg Compound B, or a pharmaceutically acceptable salt form thereof, once daily for 14 consecutive days; followed by (b) a 7 day treatment cycle that comprises (i) administering once daily 3 mg of Compound A free base and 20 mg of Compound B, or a pharmaceutically acceptable salt form therefore, once daily for 5 consecutive days; followed by (ii) administering no Compound A or Compound B for 2 consecutive days are provided herein. In some aspects, Compound B is administered in both the lead-in period and treatment cycle as a pharmaceutically acceptable salt form. In some aspects, the pharmaceutically acceptable salt form is a maleate salt, which can be a sesqui-maleate salt. In some aspects, the amount of Compound B as a maleate salt, which can be a sesqui-maleate salt, administered in the lead-in period is about 20 mg. In some aspects, the amount of Compound B as a maleate salt, which can be a sesqui-maleate salt, administered in the treatment period is about 27 mg In some aspects, methods of treating a patient having a solid tumor comprising:

(a) a lead-in period that comprises administering 15 mg Compound B, or a pharmaceutically acceptable salt form thereof, once daily for 14 consecutive days; followed by (b) a 7 day treatment cycle that comprises (i) administering once daily 4 mg of Compound A free base and 20 mg of Compound B, or a pharmaceutically acceptable salt form therefore, once daily for 5 consecutive days; followed by (ii) administering no Compound A or Compound B for 2 consecutive days are described herein. In some aspects, Compound B is administered in both the lead-in period and treatment cycle as a pharmaceutically acceptable salt form. In some aspects, the pharmaceutically acceptable salt form is a maleate salt, which can be a sesqui-maleate salt. In some aspects, the amount of Compound B as a maleate salt, which can be a sesqui-maleate salt, administered in the lead-in period is about 20 mg. In some aspects, the amount of Compound B as a maleate salt, which can be a sesqui-maleate salt, administered in the treatment period is about 27 mg.

In some aspects, methods of treating a patient having a solid tumor comprising:

(a) a lead-in period that comprises administering a total of 3 mg Compound A free base divided over two doses per day and 15 mg Compound B, or a pharmaceutically acceptable salt form thereof, once daily, for 14 consecutive days; followed by (b) a 7 day treatment cycle that comprises (i) administering once daily 3 mg of Compound A free base and 15 mg of Compound B, or a pharmaceutically acceptable salt form therefore, for 5 consecutive days; followed by (ii) administering no Compound A or Compound B for 2 consecutive days are provided herein. In some aspects, Compound B is administered in both the lead-in period and treatment cycle as a pharmaceutically acceptable salt form. In some aspects, the pharmaceutically acceptable salt form is a maleate salt, which can be a sesqui-maleate salt. In some aspects, the amount of Compound B as a maleate salt, which can be a sesqui-maleate salt, administered in the lead-in period is about 13 mg. In some aspects, the amount of Compound B as a maleate salt, which can be a sesqui-maleate salt, administered in the treatment period is about 20 mg.

In some aspects, methods of treating a patient having a solid tumor comprising:

(a) a lead-in period that comprises administering a total of 4 mg Compound A free base divided over two doses per day and 15 mg Compound B, or a pharmaceutically acceptable salt form thereof, once daily for 14 consecutive days; followed by (b) a 7 day treatment cycle that comprises (i) administering once daily 4 mg of Compound A free base and 15 mg of Compound B, or a pharmaceutically acceptable salt form therefore, once daily for 5 consecutive days; followed by (ii) administering no Compound A or Compound B for 2 consecutive days are described herein. In some aspects, Compound B is administered in both the lead-in period and treatment cycle as a pharmaceutically acceptable salt form. In some aspects, the pharmaceutically acceptable salt form is a maleate salt, which can be a sesqui-maleate salt. In some aspects, the amount of Compound B as a maleate salt, which can be a sesqui-maleate salt, administered in the lead-in period is about 13 mg. In some aspects, the amount of Compound B as a maleate salt, which can be a sesqui-maleate salt, administered in the treatment period is about 20 mg.

In some aspects, methods of treating a patient having a solid tumor comprising administering twice daily 2 mg Compound A as free base and once daily 5 mg Compound B, or a pharmaceutically acceptable salt thereof, are described herein. In some aspects, Compound B is a pharmaceutically acceptable salt form. In some aspects, the pharmaceutically acceptable salt form is a maleate salt which can be a sesqui-maleate salt. In some aspects, the amount of Compound B, as a maleate salt, which can be a sesqui-maleate salt, is about 7 mg.

In some aspects, methods of treating a patient having a solid tumor comprising administering twice daily 4 mg Compound A as free base and once daily 5 mg Compound B, or a pharmaceutically acceptable salt thereof, are described herein. In some aspects, Compound B is a pharmaceutically acceptable salt form. In some aspects, the pharmaceutically acceptable salt form is a maleate salt which can be a sesqui-maleate salt. In some aspects, the amount of Compound B, as a maleate salt, which can be a sesqui-maleate salt, is about 7 mg.

In some aspects, methods of treating a patient having a solid tumor comprising administering twice daily 6 mg Compound A as free base and once daily 5 mg Compound B, or a pharmaceutically acceptable salt thereof, are described herein. In some aspects, Compound B is a pharmaceutically acceptable salt form. In some aspects, the pharmaceutically acceptable salt form is a maleate salt which can be a sesqui-maleate salt. In some aspects, the amount of Compound B, as a maleate salt, which can be a sesqui-maleate salt, is about 7 mg.

In some aspects, methods of treating a patient having a solid tumor comprising administering twice daily 2 mg Compound A as free base and twice daily 5 mg Compound B, or a pharmaceutically acceptable salt thereof, are described herein. In some aspects, Compound B is a pharmaceutically acceptable salt form. In some aspects, the pharmaceutically acceptable salt form is a maleate salt which can be a sesqui-maleate salt. In some aspects, each dose of Compound B, as a maleate salt, which can be a sesqui-maleate salt, is about 7 mg.

In some aspects, methods of treating a patient having a solid tumor comprising administering twice daily 4 mg Compound A as free base and twice daily 5 mg Compound B, or a pharmaceutically acceptable salt thereof, are described herein. In some aspects, Compound B is a pharmaceutically acceptable salt form. In some aspects, the pharmaceutically acceptable salt form is a maleate salt which can be a sesqui-maleate salt. In some aspects, each dose of Compound B, as a maleate salt, which can be a sesqui-maleate salt, is about 7 mg In some aspects, methods of treating a patient having a solid tumor comprising administering twice daily 6 mg Compound A as free base and twice daily 5 mg Compound B, or a pharmaceutically acceptable salt thereof, are described herein. In some aspects, Compound B is a pharmaceutically acceptable salt form. In some aspects, the pharmaceutically acceptable salt form is a maleate salt which can be a sesqui-maleate salt. In some aspects, each dose of Compound B, as a maleate salt, which can be a sesqui-maleate salt, is about 7 mg

EXAMPLES

It is understood that the examples and aspects described herein are for illustrative purposes only and that various modifications or changes in light thereof will be suggested to persons skilled in the art and are to be included within the spirit and purview of this application.

Example 1: Combination Effect of Compound A and Compound Bin KRAS Mutant NSCLC Cell Lines A cell viability assay was carried out for combinatorial treatment of Compound A (mirdametinib) and Compound B (lifirafenib maleate) in human non-small cell lung cancer and colorectal cancer cell lines harboring K-RAS mutations (A549, NCI-H2122, NCI-H23, Sk-Lu-1, Calu-1, NCI-H1299, NCI-H358).

The mutant cell lines used were grown according to standard cell culture techniques, with varying concentrations from 0-10 μM of mirdametinib and lifirafenib diluted with dimethyl sulfoxide (54686.500, biomol). Cell lines were grown in RPMI1640 medium (22400-089, GIBCO®), McCoy's 5a (16600-082, GIBCO) or, DMEM (11965-092, GIBCO®), each with 10% fetal bovine serum (SH30084.03, Hyclone™) and 1% penicillin-streptomycin (15140-148, Invitrogen).

Briefly, for each experiment, about 3,000 cells were plated in each well of a 96-well plate and the plates were incubated overnight. Varying levels of mirdametinib and lifirafenib were added to each well, and cells were incubated for three days. Cell viability was determined according to manufacturer instructions using CellTiterGlo® Luminescent Cell Viability Assay (G7570, Promega™), with a BMG LABTECH PERAstar FS plate reader.

Results

Compound A (mirdametinib) and Compound B maleate (lifirafenib maleate) synergistically inhibited the proliferation of multiple non-small cell lung cancer and colorectal cell lines harboring K-RAS mutations. In 7 of the 8 cell lines evaluated, the combination of mirdametinib and lifirafenib maleate demonstrated synergistic cell killing activity versus either compound alone.

TABLE 1

| Cell line | KRAS Mutation | Maximum $EC_{50}$ shift |
|---|---|---|
| Calu-6 | Q61K | 59 fold decrease |
| A549 | G12S | 11 fold decrease |
| NCI-H2122 | G12C | 21 fold decrease |
| NCI-H23 | G12C | 22 fold decrease |
| Sk-Lu-1 | G12D | 32 fold decrease |
| NCI-H1299 | Q61K | 16 fold decrease |
| NCI-H358 | G12C | 18 fold decrease |
| Calu-1 | G12C | No shift |

No shift: less than 2 fold $EC_{50}$ shift was detected by combining Compound B maleate with Compound A in the indicated cell line.

Example 2: Efficacy Study of Compound A and Compound B in Calu-6 K-RAS Mutated Human Xenograft Lung Adenocarcinoma Model in Balb/c Nude Mice 1. Study Objective To determine the effects of Compound B Maleate and Compound A, alone or in combination, on growth of subcutaneous Calu-6 tumors which harbor a K-RAS mutation in Balb/c nude mice in an Efficacy Study.

2. Study Design

Experimental designs for the Efficacy study are illustrated in Table 2.

TABLE 2

Experimental groups in the Efficacy Study.

| Group | Mouse | Compound B maleate* (mg/kg) | Compound A (mg/kg) | Route/ Vol | Frequency | Initiation | Termination |
|---|---|---|---|---|---|---|---|
| 1 | 10 | 0 | 0 | p.o./10 ml/kg | BID** | 120-150 $mm^3$ | <2000 $mm^3$ in Veh*** |
| 2 | 10 | 2.5 | 0 | p.o./10 ml/kg | BID** | 120-150 $mm^3$ | <2000 $mm^3$ in Veh*** |
| 3 | 10 | 1.25 | 0.5 | p.o./10 ml/kg | BID** | 120-150 $mm^3$ | <2000 $mm^3$ in Veh*** |
| 4 | 10 | 1.25 | 1.5 | p.o./10 ml/kg | BID** | 120-150 $mm^3$ | <2000 $mm^3$ in Veh*** |

TABLE 2-continued

Experimental groups in the Efficacy Study.

| Group | Mouse | Compound B maleate* (mg/kg) | Compound A (mg/kg) | Route/ Vol | Frequency | Initiation | Termination |
|---|---|---|---|---|---|---|---|
| 5 | 10 | 1.25 | 5 | p.o./10 ml/kg | BID** | 120-150 $mm^3$ | <2000 $mm^3$ in Veh*** |

*Dose for Compound B maleate is based on the free base form.
**For both compounds
***Mean tumor volume of the vehicle-treated group (Group 1)

3. Materials 3.1 Animals and Housing Condition 6-8 week old female Balb/c nude mice with a mean body weight of about 18 g were housed under standard laboratory conditions and given free access to sterile food and water.

3.2 Cells

Calu-6 cell lines were cultured in Minimal Essential Medium (ThermoFisher, #11095080), with phosphate buffered saline (Gibco®, #C20012500BT), non-essential amino acids (ThermoFisher, #11140-050), fetal bovine serum (ExCell™ Bio, #FND500), Matrigel® (Corning, #354234) and penicillin/streptomycin (ThermoFisher, #15140122).

3.4 Formulation Method

The required amount of methylcellulose was slowly added to purified water (approximately 60% to 80% of total volume) with continuous stirring until a clear solution was obtained by visual inspection. Next, purified water was added to reach the final volume and the mixture was stirred until a homogenous solution was obtained by visual inspection. This solution was autoclaved. Tween-80 was then be added to achieve final concentration of 1% (v/v) and solution was stored at 4° C.

Formulation of dosing solutions for Group 1 to Group 5 is illustrated in Table 3 below. Both compounds were formulated as homogenous suspension and prepared once weekly, and stored at 4° C. in dark. Required amount of test article was added to a volume slightly smaller than the calculated volumes of vehicle solution with stirring. Vehicle solution was added to reach the final volume and the mixture was stirred for at least 10 minutes until a homogenous suspension was obtained by visual inspection. The homogenous dosing solution for each group was aliquoted for each dosing day. On the day of dosing, the tubes with aliquoted dosing solutions were vortexed or inverted until a homogenous suspension was achieved before each dosing.

TABLE 3

Formulation of dosing solutions

| Group | Drug Doses | Dosing Solution** | Dosing Volume | Frequency |
|---|---|---|---|---|
| 1 | vehicle solution | vehicle solution | 10 ml/kg | BID |
| 2 | 0.25 mg/ml Compound B | 0.34 mg/ml Compound B maleate** | 10 ml/kg | BID |
| 3 | 0.125 mg/ml Compound B* + 0.05 mg/ml Compound A | 0.17 mg/ml Compound B maleate** + 0.05 mg/ml Compound A | 10 ml/kg | BID |
| 4 | 0.125 mg/ml Compound B* + 0.15 mg/ml Compound A | 0.17 mg/ml Compound B maleate** + 0.15 mg/ml Compound A | 10 ml/kg | BID |

TABLE 3-continued

Formulation of dosing solutions

| Group | Drug Doses | Dosing Solution** | Dosing Volume | Frequency |
|---|---|---|---|---|
| 5 | 0.125 mg/ml Compound B* + 0.5 mg/ml Compound A | 0.17 mg/ml Compound B maleate** + 0.5 mg/ml Compound A | 10 ml/kg | BID |

*The required dose of the free base form of Compound B
**The calculated concentration of Compound B maleate in the dosing solution = Dose of free base × 652.52/478.43

4. Experimental Methods and Procedures:

4.1 Cell Culture

Calu-6 tumor cells were cultured in MEM medium supplemented with 10% FBS, 1% NEAA, 1× penicillin/streptomycin at 37° C. in an atmosphere of 5% $CO_2$. Tumor cells were routinely sub-cultured twice weekly per ATCC instruction.

4.2 Mycoplasma Test and Short Tandem Repeat (STR) Analysis

STR and mycoplasma tests were performed to ensure the authenticity and quality of tumor cells. Results indicated that the Calu-6 cells used in this study were STR correct and mycoplasma negative.

4.3 Tumor Cell Inoculation and Mouse Grouping

Each mouse was inoculated subcutaneously at the right flank with Calu-6 tumor cells ($5\times10^6$ cells in 0.1 ml 50% Matrigel® in MEM). Tubes containing suspended cells and syringes were kept on ice to avoid solidification of Matrigel®. 2× overage was implemented for cell injection. When mean tumor volume reached the indicated sizes in Table 2, animals were randomly assigned to the indicated groups in Table 2 and received the first dosing.

4.4 Dosing

Test articles and vehicle solution were administrated by oral gavage ("p.o.") twice daily (BID, ≥8 h interval between two dosings in one day). Dosing solution was prepared as described in Table 3 once weekly and as complete homogenous suspension before each dosing. Dosing volumes were given based on results from the previous mouse body weight measurement. Animals were treated either throughout the study per parameters described in Table 2.

4.5 Tumor Measurements and Collection

Tumor volumes and mouse body weights were measured three times weekly after tumors became palpable and before randomization and grouping. Afterwards, tumor volumes and mouse body weights were measured twice weekly to termination, in two dimensions using a caliper, and the tumor volumes were expressed in $mm^3$ using the formula: $V=0.5\ L\times W^2$, where L and W were the long and short diameters of the tumor, respectively. The TGI value for the drug A-treated group at Day X was calculated as following:

TGI (%)={1−[mTV(drug at Day X)−mTV(drug at Day 0)]/[mTV(veh at Day X)−mTV(veh at Day 0)]}×100, where mTV represented mean tumor volume.

4.6 Statistical Analysis

A two-way ANOVA was performed to compare tumor volumes among different treatment groups. A $P<0.05$ was considered statistically significant.

5. Summary of Results

Figure 3:
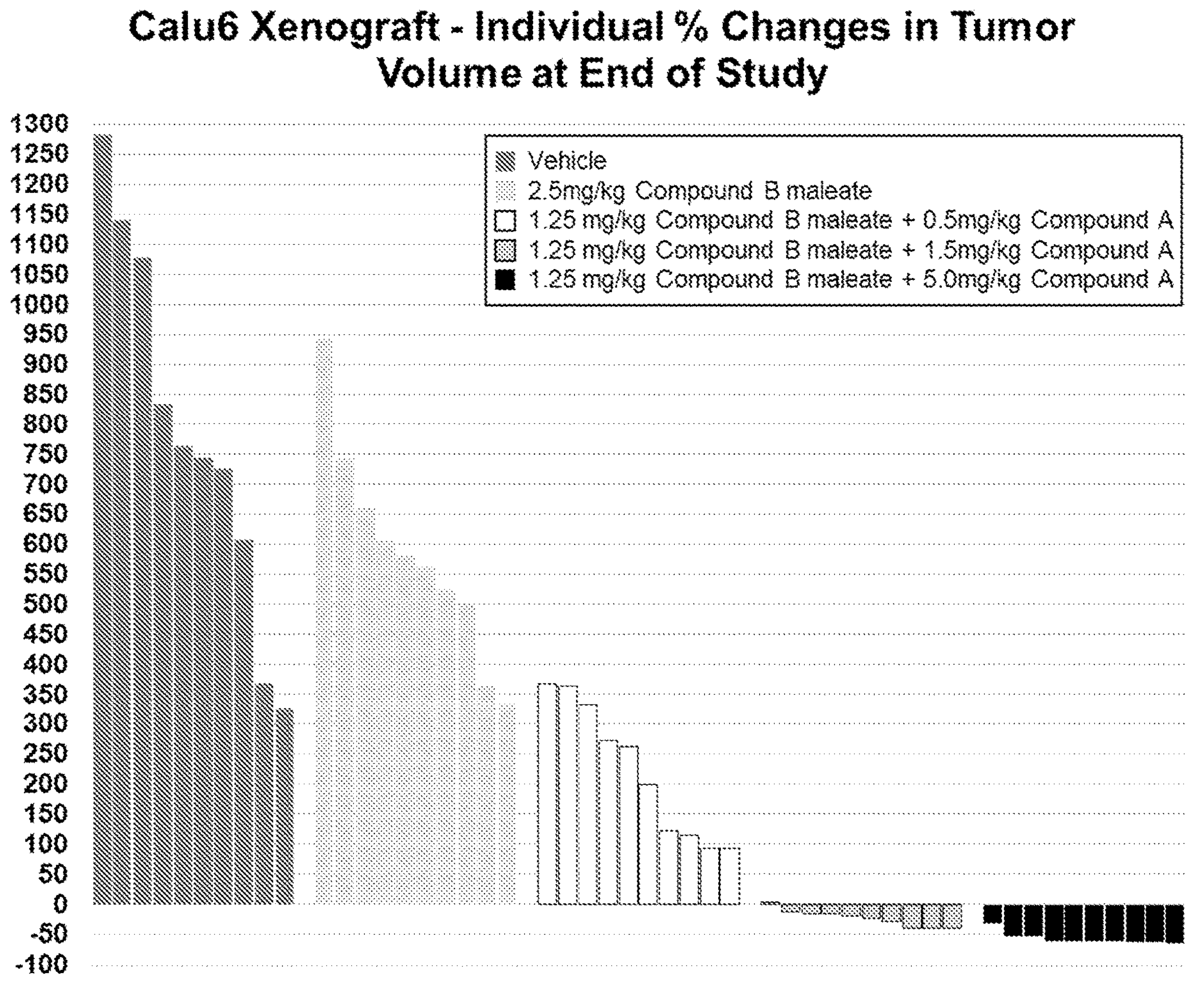
FIG. 3 shows the percentage change in final volumes versus baseline for each of the individual Calu-6 tumors implanted in Balb/c nude mice treated with varying concentrations of Compound A and Compound B maleate.

Compared to the vehicle control, treatment with Compound B maleate and Compound A at all tested doses, alone or in combination, resulted in significant inhibition of Calu-6 tumor growth (FIGS. 1 and 3). Increasing doses of Compound A added to a consistent dose of Compound B maleate led to dose-dependent improvements in tumor growth inhibition, consistent with the in vitro data that demonstrated cell killing synergy between the two compounds in K-RAS mutated cancer cell lines. The greatest tumor growth inhibition in this experiment was observed at a dose 1.25 mg/kg Compound B maleate and 5 mg/kg Compound A.

Figure 2:
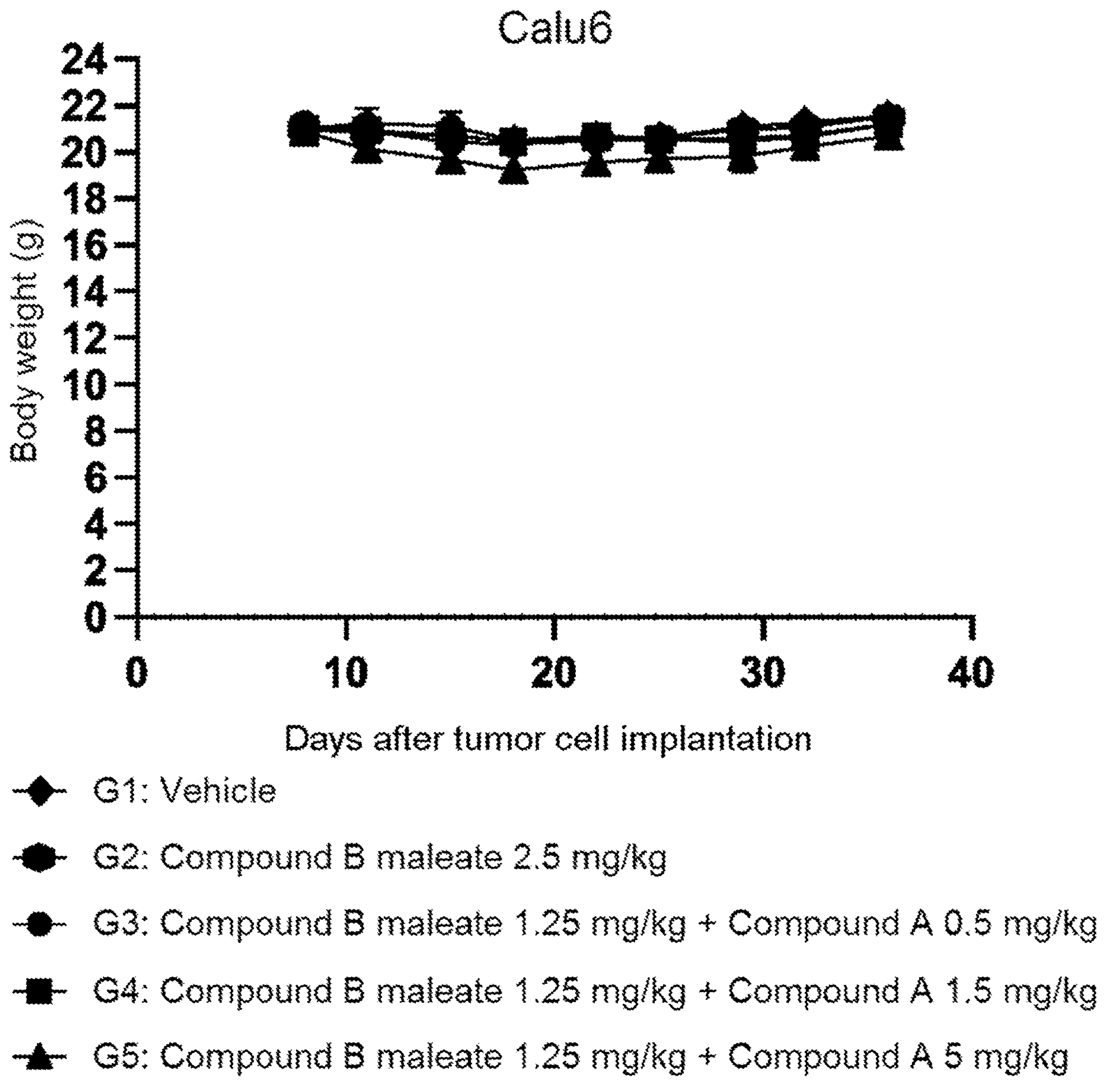
FIG. 2 shows the body weight over time of mice implanted with Calu-6 tumors and treated with varying concentrations of Compound A and Compound B maleate.

FIG. 2 demonstrates a relatively stable mouse body weight over time, with marginal differences between Groups, suggesting that the combination of Compound A and Compound B maleate was well tolerated.

Example 3: Synergistic Effective Between Compound A and Compound B

We applied BIGL methods with Highest Single Agent (HSA) null model to evaluate synergy effect of the combination of a BRAF inhibitor (BGB-283, lifirafenib) and a MEK inhibitor (PD-0325901, mirdametinib) in multiple KRAS mutant cell lines. HSA model does not attempt to model interaction effects and the predicted effect of a combination is the minimum of both monotherapy curves.

Data were collected from 3 plates with identical layout that includes negative and positive controls, 8 doses of each single agent, and 8×8=64 combined doses. The raw signals were normalized by controls before pooling for analysis. Both raw data and normalized were shown in data plots.

The presence of synergistic or antagonistic effects were evaluated by statistical tests. Two types of tests were conducted

- Overall test (meanR): that evaluates how the predicted response surface differs from the observed one. If the null hypothesis is rejected, this test suggests that at least some dose combinations may exhibit either synergistic or antagonistic behaviour.
- Dose combination test (maxR): that evaluates presence of synergistic or antagonistic effects for each dose combination and as such provides a point-by-point classification.

Both of the above test statistics have a well specified null distribution under a set of assumptions, namely normality of Z-scores. If this assumption is not satisfied, distribution of these statistics can be estimated using bootstrap. The results based on both normal and bootstrapping errors were provided.

More statistics analysis details can be found at Van der Borght, K., et al., *Sci Rep* 7:17935 (2017) and the methodology vignette.

TABLE 4

| Cell Line | RAS mutation | Overall test p-value * | Percentage of combinations show synergistic effect ** | Maximum $EC_{50}$ shift for mirdametinib |
|---|---|---|---|---|
| HCT116 | K-RAS$^{G13D}$ | <0.0001 | 34% | >100 fold ↓ |
| LU65 | K-RAS$^{G12C}$ | <0.0001 | 31% | >100 fold ↓ |
| H2122 | K-RAS$^{G12C}$ | <0.0001 | 23% | >100 fold ↓ |
| MiaPaCa-2 | K-RAS$^{G12C}$ | <0.0001 | 19% | 2 fold ↓ |
| Calu-1 | K-RAS$^{G12C}$ | <0.0001 | 13% | NA |
| Sk-Mel-2 | K-RAS$^{Q61R}$ | <0.0001 | 13% | No shift |
| SW837 | K-RAS$^{G12C}$ | <0.0001 | 6% | 3 fold |
| NCI-H358 | K-RAS$^{G12C}$ | <0.0001 | 5% | 2 fold |
| NCI-H2030 | K-RAS$^{G12C}$ | <0.0001 | 2% | NA |
| NCI-H23 | K-RAS$^{G12C}$ | 0.036 | 2% | NA |
| SW620 | K-RAS$^{G12V}$ | <0.0001 | 2% | NA |
| A549 | K-RAS$^{G12S}$ | <0.0001 | 0% | 15 fold ↓ |
| HCT15 | K-RAS$^{G13D}$ | 1.000 | 0% | NA |
| Sk-Mel-119 | K-RAS$^{Q61K}$ | 0.036 | 0% | No shift |
| SK-Mel-285 | K-RAS$^{G12C}$ | 0.929 | 0% | NA |
| Sk-Mel-30 | K-RAS$^{Q61K}$ | 0.143 | 0% | NA |
| SW1573 | K-RAS$^{G12C}$ | <0.0001 | 0% | NA |
| SW480 | K-RAS$^{G12V}$ | 0.679 | 0% | NA |

* p-values for the hypothesis that at least one of the considered dose combinations exhibits either synergistic or antagonistic behavior.

** The percentage of the considered dose combinations with synergy at significance level 0.05.

No shift: less than 2 fold $EC_{50}$ shift was detected

NA: cell line is not sensitive to miradametib alone or in combination with lifirafenib, and no dose dependent curve can be generated

Example 4: Antiproliferation Effect by Combining Compound B with Different MEK Inhibitors in K/N-RAS Mutated NSCLC and CRC Cell The antiproliferative activity of compounds in a panel of RAS mutant NSCLC and CRC cell line has been determined using CellTiter-Glo luminescent cell viability assay (Promega). See, Yuan et al., Molecular Oncology 14 (2020) 1833-1849, the disclosure of which is hereby incorporated by reference in its entirety. The number of cells seeded per well of a 96-well plate was optimized for each cell line to ensure logarithmic growth over the three-day treatment period. Cells were incubated for 16 h and then treated with a 10-point dilution series in duplicate. Following a 3-day exposure to compounds, a volume of CellTiter-Glo reagent equal to the volume of cell culture medium was added into each well. Mixture was mixed on an orbital shaker for 2 min to allow cell lysing, followed by 10-min incubation at RT to allow development and stabilization of luminescent signal. Luminescent signal was measured using PHERAstar FS reader (BMG Labtech).

Excess over Highest Single Agent (EOHSA) is a standard criterion for evaluating drug combinatorial effects on cell growth inhibition. EOHSA was used to analyze the excess inhibition effects produced by the drug combination over the larger effects produced by two single agents at corresponding concentrations. For analysis purpose, it is assumed that the log of the difference of each raw measurement/positive control and the negative control follows a normal distribution with different means but the same variance. The model is fitted by the maximum-likelihood method, and the EOHSA for each dose combination was calculated by applying the fitted model to the EOHSA calculation formula.

Tables 5-7 provide the inhibition observed in multiple cell lines for combinations of Compound B and various MEK inhibitors. The p-values (*) were calculated using the testing procedure described in Perone et al., *J Am Stat Assoc.* 99:1002-14. The calculations were applied to control the false discovery exceedance at 5%, for the hypothesis that at least one of the considered dose combinations has synergy per EOHSA. Tables 5-7 provide the percentage of the considered dose combinations with synergy (**) using the Pacifico approach at significance level 0.05. No shift is defined as less than 2-fold EC50 shift detected after combination of Compound B with the MEK inhibitor.

TABLE 5

Inhibition of the proliferation of multiple NSCLC cell lines harboring K/N-RAS mutations with a combination of Compound A and Compound B.

| Cell Line | EOHSA | | Maximum $EC_{50}$ shift for PD-0325901 |
|---|---|---|---|
| | p-value* | Percentage** | |
| NSCLC: | | | |
| Calu-6 | 0.0001 | 0.17 | 59 fold ↓ |
| A549 | <0.0001 | 0.17 | 11 fold ↓ |
| NCI-H2122 | <0.0001 | 0.16 | 21 fold ↓ |
| NCI-H23 | <0.0001 | 0.22 | 22 fold ↓ |
| SW1573 | <0.0001 | 0.27 | 97 fold ↓ |
| NCI-H358 | 0.2361 | 0.00 | 18 fold ↓ |
| NCI-H1299 | <0.0001 | 0.14 | 16 fold ↓ |
| Calu-1 | 0.8944 | 0.00 | No shift |
| Sk-Lu-1 | 0.0015 | 0.09 | 32 fold ↓ |

TABLE 6

Inhibition of the proliferation of multiple NSCLC and CRC cell lines harboring K/N-RAS mutations with a combination of Compound B and MEK inhibitor pimarsertib

| Cell Line | EOHSA | | Maximum $EC_{50}$ shift for pimarsertib |
|---|---|---|---|
| | p-value* | Percentage** | |
| NSCLC: | | | |
| Calu-6 | <0.0001 | 0.42 | 12 fold ↓ |
| A549 | <0.0001 | 0.30 | 42 fold ↓ |
| NCI-H2122 | <0.0001 | 0.09 | 6 fold ↓ |
| NCI-H23 | <0.0001 | 0.44 | 20 fold ↓ |
| SW1573 | <0.0001 | 0.25 | >100 fold ↓ |
| NCI-H358 | 0.0001 | 0.41 | >100 fold ↓ |
| NCI-H1299 | <0.0001 | 0.27 | 45 fold ↓ |
| Calu-1 | 0.0001 | 0.11 | 7 fold ↓ |
| Sk-Lu-1 | <0.0001 | 0.17 | 9 fold ↓ |
| CRC: | | | |
| LS174T | <0.0001 | 0.16 | 15 fold ↓ |
| Lovo | <0.0001 | 0.19 | 18 fold ↓ |
| T84 | <0.0001 | 0.27 | 44 fold ↓ |
| DLD-1 | <0.0001 | 0.36 | >100 fold ↓ |
| HCT8 | <0.0001 | 0.12 | 54 fold ↓ |
| HCC2998 | <0.0001 | 0.2 | 31 fold ↓ |
| SW480 | <0.0001 | 0.17 | No shift |

TABLE 7

Inhibition of the proliferation of multiple NSCLC cell lines harboring K/N-RAS mutations with a combination of Compound B and MEK inhibitor RO5126766

| Cell Line | EOHSA | | Maximum $EC_{50}$ shift for RO5126766 |
|---|---|---|---|
| | p-value* | Percentage** | |
| NSCLC: | | | |
| Calu-6 | <0.0001 | 0.08 | 5 fold ↓ |
| A549 | <0.0001 | 0.16 | 2 fold ↓ |
| NCI-H2122 | 0.0350 | 0.02 | 3 fold ↓ |
| NCI-H23 | <0.0001 | 0.20 | 4 fold ↓ |

TABLE 7-continued

Inhibition of the proliferation of multiple NSCLC cell lines harboring K/N-RAS mutations with a combination of Compound B and MEK inhibitor RO5126766

| Cell Line | EOHSA | | Maximum $EC_{50}$ shift for RO5126766 |
|---|---|---|---|
| | p-value* | Percentage** | |
| SW1573 | 0.0005 | 0.12 | 5 fold ↓ |
| NCI-H358 | <0.0001 | 0.20 | No shift |
| NCI-H1299 | <0.0001 | 0.17 | No shift |
| Calu-1 | <0.0001 | 0.28 | No shift |
| Sk-Lu-1 | <0.0001 | 0.33 | 5 fold ↓ |

Example 5: Human Clinical Trials

Figure 4:
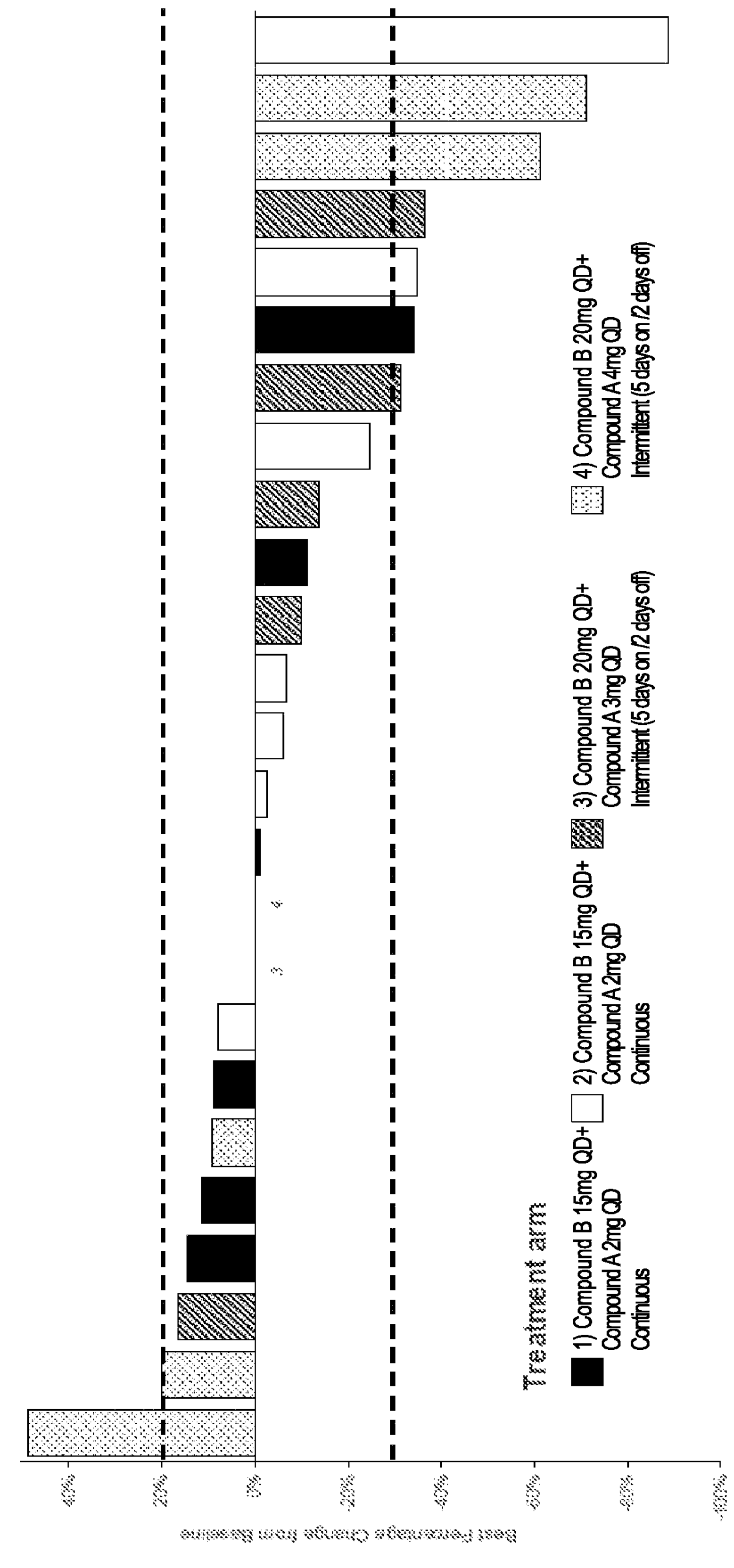
FIG. 4 shows the best change (%) from baseline in tumor size (defined by the sum of the longest diameter of the target lesions) in advanced or refractory solid tumor patients having a mutation in a MAPK gene.

Part 1 (Phase 1b dose escalation) of lifirafenib and mirdametinib has, to date, included 26 patients with advanced, metastatic or unresectable solid cancers. The patients were treated in four sequential dose cohorts. The first two dose cohorts (DL1 and DL2) evaluated lifirafenib and mirdametinib given once daily on the continuous dosing schedule, where the DL1 cohort included 15 mg of lifirafenib combined with 2 mg of mirdametinib in 6 subjects and the DL2 cohort evaluated 20 mg of lifirafenib combined with 2 mg of mirdametinib in 8 subjects. The latter two dose cohorts (DL3a and DL4a) evaluated lifirafenib and mirdametinib on an intermittent dosing schedule (once daily for 5 days followed by 2 days off in every week), where the DL3a cohort included 20 mg of lifirafenib combined with 3 mg of mirdametinib in 6 subjects and the DL4a cohort evaluated 20 mg of lifirafenib combined with 4 mg of mirdametinib in 6 subjects. One treatment cycle in all dose cohorts was 28 days. Initial results in patients having advanced solid cancers (e.g., ovarian, CRC, NSCLC, endometrial) are provided in FIG. 4.

After the completion of dose cohort 4a, Part 1 (Phase 1b dose escalation) will continue in two parallel dose escalation arms (arm b and arm c). In both arms, lifirafenib and mirdametinib will be evaluated in sequential dose escalation cohorts on an intermittent dosing schedule (5 days followed by 2 days off in every week). One treatment cycle will be 28 days. In both arms, the lifirafenib dose will be fixed across all dose escalation cohorts. In arm b, lifirafenib will be given as the lead-in dose of 15 mg once daily during the first 2 weeks (14 days) followed by the target dose of 20 mg once daily during the 28-day treatment period. In arm c, lifirafenib will be given as the lead-in dose of 10 mg once daily during the first 2 weeks (14 days) followed by the target dose of 15 mg once daily during the 28-day treatment period. The starting dose cohort in arm b (DL3b) will evaluate 15 mg and 20 mg of lifirafenib once daily (lead in and target dose, respectively) combined with 3 mg of mirdametinib once daily. The starting dose cohort in arm c (DL3c) will evaluate 10 mg and 15 mg of lifirafenib once daily (lead in and target dose, respectively) combined with 2 mg of mirdametinib twice daily. In subsequent dose escalation cohorts, mirdametinib dose will be escalated by 1-2 mg once daily (arm b) and 1-2 mg twice daily (arm b) if tolerated.

A standalone Phase 1b/2a dose finding study will be conducted to evaluate lifirafenib and mirdametinib patients with advanced, metastatic or unresectable solid cancers. Part 1 (Phase 1b dose escalation) of this study will include two parallel dose escalation arms (arm a and arm b). In both arms, lifirafenib and mirdametinib will be evaluated in 3 sequential dose escalation cohorts. Both drugs will be given on the continuous dosing schedule and one treatment cycle will be 28 days. In both arms, the lifirafenib dose will be fixed across dose escalation cohorts. In arm a, lifirafenib will be given at the dose of 5 mg once daily and in arm b, lifirafenib will be given at the dose of 5 mg twice daily. The starting dose cohort in arm a (DL1a) will evaluate 5 mg of lifirafenib once daily combined with 2 mg of mirdametinib twice daily. The starting dose cohort in arm b (DL1b) will evaluate 5 mg of lifirafenib twice daily combined with 2 mg of mirdametinib twice daily. The dose escalation may proceed in additional 2 sequential cohorts (DL2a-DL3a in arm and DL2b-DL3b in arm b). This means that after the starting dose cohort (DL1a and DL1b), two subsequent dose escalation cohorts in respective arms will evaluate the same lifirafenib doses (5 mg once daily in arm and 5 mg twice daily in arm b), combined with mirdametinib doses escalated by 2 mg twice daily in each escalation step in both arms (4 mg twice daily in DL2a and DL2b and 6 mg twice daily in DL3a and D13b).

Example 4: Capsule Formulations

| | Compound A/Compound B (1/5 mg) | | Compound A/ Compound B (2/20 mg) | |
|---|---|---|---|---|
| Component | % | mg/capsule | % | mg/capsule |
| Compound A | 1.00% | 1.00 | 1.00% | 2.00 |
| Compound B (Maleic acid salt) | 6.82% | 6.82 | 13.64% | 27.28 |
| SMCC50 | 85.93% | 85.93 | 79.11% | 158.22 |
| Croscarmellose sodium | 4.00% | 4.00 | 4.00% | 8.00 |
| Sodium Stearyl Fumarate (intra) | 2.00% | 2.00 | 2.00% | 4.00 |
| Sodium Stearyl Fumarate (extra) | 0.25% | 0.25 | 0.25% | 0.50 |
| Total Gelatin capsule | 100% | 100.00 | 100% | 200.00 |

Other Aspects

All publications, patents, and patent applications mentioned in this specification are incorporated herein by reference in their entirety to the same extent as if each individual publication, patent, or patent application was specifically and individually indicated to be incorporated by reference in its entirety. Where a term in the present application is found to be defined differently in a document incorporated herein by reference, the definition provided herein is to serve as the definition for the term.

While the invention has been described in connection with specific aspects thereof, it will be understood that invention is capable of further modifications and this application is intended to cover any variations, uses, or adaptations following, in general, the principles and including such departures from the present disclosure that come within known or customary practice within the art to which the invention pertains and can be applied to the essential features hereinbefore set forth, and follows in the scope of the claimed.

In addition to the various embodiments described herein, the present disclosure includes the following embodiments numbered E1 through E369. This list of embodiments is presented as an exemplary list and the application is not limited to these embodiments.

E1. A method of treating a patient having a solid tumor comprising co-administering to the patient a therapeutically effective amount of Compound A (mirdametinib), or a pharmaceutically acceptable salt form thereof, and a therapeutically effective amount of Compound B (lifirafenib), or a pharmaceutically acceptable salt form thereof.

E2. The method of E1, wherein the therapeutically effective amount of Compound A is about 1 mg to about 5 mg per day.

E3. The method of E1, wherein the therapeutically effective amount of Compound B, or a pharmaceutically acceptable salt form thereof, is about 5 mg to about 40 mg per day.

E4. The method of E1, wherein the therapeutically effective amount of Compound A is about 1 mg per day and the therapeutically effective amount of Compound B, or a pharmaceutically acceptable salt form thereof, is about 5 mg to about 15 mg per day.

E5. The method of E1, wherein the therapeutically effective amount of Compound A is about 2 mg per day and the therapeutically effective amount of Compound B, or a pharmaceutically acceptable salt form thereof, is about 5 mg to about 40 mg per day.

E6. The method of E1, wherein the therapeutically effective amount of Compound A is about 2 mg per day and the therapeutically effective amount of Compound B, or a pharmaceutically acceptable salt form thereof, is about 20 mg to about 35 mg per day.

E7. The method of E1, wherein the therapeutically effective amount of Compound A is about 3 mg per day and the therapeutically effective amount of Compound B, or a pharmaceutically acceptable salt form thereof, is about 5 mg to about 40 mg per day.

E8. The method of E1, wherein the therapeutically effective amount of Compound A is about 3 mg per day and the therapeutically effective amount of Compound B, or a pharmaceutically acceptable salt form thereof, is about 20 mg to about 35 mg per day.

E9. The method of E1, wherein the therapeutically effective amount of Compound A is about 4 mg per day and the therapeutically effective amount of Compound B, or a pharmaceutically acceptable salt form thereof, is about 10 mg to about 40 mg per day.

E10. The method of E1, wherein the therapeutically effective amount of Compound A is about 4 mg per day and the therapeutically effective amount of Compound B, or a pharmaceutically acceptable salt form thereof, is about 20 mg to about 35 mg per day.

E11. The method of E1, wherein the therapeutically effective amount of Compound A is about 5 mg per day and the therapeutically effective amount of Compound B, or a pharmaceutically acceptable salt form thereof, is about 10 mg to about 40 mg per day.

E12. The method of E1, wherein the therapeutically effective amount of Compound A is about 5 mg per day and the therapeutically effective amount of Compound B, or a pharmaceutically acceptable salt form thereof, is about 20 mg to about 40 mg per day.

E13. The method of any one of E1-E12, wherein Compound B is a pharmaceutically acceptable salt form.

E14. The method of E13, wherein the pharmaceutically acceptable salt form is a maleate salt, which can be a sesqui-maleate salt.

E15. The method of E14, wherein the therapeutically effective amount of Compound A is about 1 mg per day and the therapeutically effective amount of Compound B as a maleate salt, which can be a sesqui-maleate salt, is about 5 mg to about 10 mg per day.

E16. The method of E14, wherein the therapeutically effective amount of Compound A is about 1 mg per day and the therapeutically effective amount of Compound B as a maleate salt, which can be a sesqui-maleate salt, is about 7 mg per day.

E17. The method of E14, wherein the therapeutically effective amount of Compound A is about 2 mg per day and the therapeutically effective amount of Compound B as a maleate salt, which can be a sesqui-maleate salt, is about 10 mg to about 30 mg per day.

E18. The method of E14, wherein the therapeutically effective amount of Compound A is about 2 mg per day and the therapeutically effective amount of Compound B as a maleate salt, which can be a sesqui-maleate salt, is about 13 mg per day.

E19. The method of E14, wherein the therapeutically effective amount of Compound A is about 2 mg per day and the therapeutically effective amount of Compound B as a maleate salt, which can be a sesqui-maleate salt, is about 27 mg per day.

E20. The method of E14, wherein the therapeutically effective amount of Compound A is about 3 mg per day and the therapeutically effective amount of Compound B as a maleate salt, which can be a sesqui-maleate salt, is about 15 mg to about 40 mg per day.

E21. The method of E14, wherein the therapeutically effective amount of Compound A is about 3 mg per day and the therapeutically effective amount of Compound B as a maleate salt, which can be a sesqui-maleate salt, is about 20 mg per day.

E22. The method of E14, wherein the therapeutically effective amount of Compound A is about 3 mg per day and the therapeutically effective amount of Compound B as a maleate salt, which can be a sesqui-maleate salt, is about 34 mg per day.

E23. The method of E14, wherein the therapeutically effective amount of Compound A is about 4 mg per day and the therapeutically effective amount of Compound B as a maleate salt, which can be a sesqui-maleate salt, is about 20 mg to about 40 mg per day.

E24. The method of E14, wherein the therapeutically effective amount of Compound A is about 4 mg per day and the therapeutically effective amount of Compound B as a maleate salt, which can be a sesqui-maleate salt, is about 27 mg per day.

E25. The method of E14, wherein the therapeutically effective amount of Compound A is about 5 mg per day and the therapeutically effective amount of Compound B as a maleate salt, which can be a sesqui-maleate salt, is about 25 mg to about 40 mg per day.

E26. The method of E14, wherein the therapeutically effective amount of Compound A is about 5 mg per day and the therapeutically effective amount of Compound B as a maleate salt is about 34 mg per day.

E27. The method of any one of E1-E26, wherein Compound A and Compound B, or a pharmaceutically acceptable salt form thereof, are administered in the same or different dosage forms.

E28. The method of E27, wherein Compound A and Compound B, or a pharmaceutically acceptable salt form thereof, are administered in the same dosage form.

E29. The method of 328, wherein the dosage form is a capsule.

E30. The method of any one of E1-E29, wherein Compound A is administered once per day.

E31. The method of any one of E1-E30, wherein Compound B, or a pharmaceutically acceptable salt form thereof, is administered once per day.

E32. The method of E27, wherein Compound A and Compound B, or a pharmaceutically acceptable salt form thereof, are administered in different dosage forms.

E33. The method of E32, wherein Compound A is administered before, concomitantly, or subsequently to the administering of Compound B, or a pharmaceutically acceptable salt form thereof.

E34. The method of E27 or E28, wherein the dosage form of Compound A is a capsule.

E35. The method of any one of E27-E34, wherein the dosage form of Compound B, or a pharmaceutically acceptable salt form thereof, is a capsule.

E36. The method of any one of E1-E35, wherein Compound A and Compound B, or a pharmaceutically acceptable salt form thereof, are administered orally.

E37. The method of any one of E1-E36, wherein the solid tumor is selected from the group consisting of malignant peripheral nerve sheath tumor, biliary tract cancer, breast cancer, cholangiocarcinoma, urothelial cancer, uterine neoplasm, lung adenocarcinoma, squamous non-small cell lung cancer, non-squamous non-small cell lung cancer, gastric cancer, sarcoma, bladder cancer, head and neck cancer, small cell lung cancer, endometrial cancer, esophageal cancer, adenoid cystic carcinoma, gallbladder cancer, colorectal cancer, thyroid cancer, hepatocellular cancer, prostate cancer, oral cancer, cervical cancer, pancreatic carcinoma, ovarian cancer, melanoma, and serous carcinoma to the peritoneum.

E38. The method of E37, wherein the patient has non-small cell lung cancer.

E39. The method of E37, wherein the patient has endometrial cancer.

E40. The method of E37, wherein the patient has ovarian cancer.

E41. The method of E40, where the patient has low grade serous ovarian cancer.

E42. The method of any one of E1-E41, wherein the patient has a confirmed mutation in one or more of KRAS, NRAS, HRAS, BRAF, NF1, MEK1, and MEK2

E43. The method of any one of E1-E42, wherein Compound A and Compound B, or a pharmaceutically acceptable salt form thereof, are administered on a 28-day dosing cycle comprising: (a) 21 days in which Compound A and Compound B, or a pharmaceutically acceptable salt form thereof, are both administered; and (b) 7 days in which neither Compound A nor Compound B, or a pharmaceutically acceptable salt form thereof, is administered.

E44. The method of any one of E1-E42, wherein Compound A and Compound B, or a pharmaceutically acceptable salt form thereof, are administered on a 28-day dosing cycle comprising (a) 21 days in which Compound A and Compound B, or a pharmaceutically acceptable salt form thereof are both administered; followed by (b) 7 days in which neither Compound A nor Compound B, or a pharmaceutically acceptable salt form thereof, is administered.

E45. The method of any one of E1-E42, wherein Compound A and Compound B, or a pharmaceutically acceptable salt form thereof, are administered on a 28-day dosing cycle comprising (a) three 7-day periods each comprising (i) 5 days in which Compound A and Compound B, or a pharmaceutically acceptable salt form thereof, are both administered and (ii) 2 days in which neither Compound A nor Compound B, or a pharmaceutically acceptable salt form thereof are administered; and (b) 7 days in which neither Compound A nor Compound B, or a pharmaceutically acceptable salt form thereof, is administered.

E46. The method of any one of E1-E42, wherein Compound A and Compound B, or a pharmaceutically acceptable salt form thereof, are administered on a 28-day dosing cycle comprising (a) three 7-day periods each comprising (i) 5 days in which Compound A and Compound B, or a pharmaceutically acceptable salt form thereof, are both administered and (ii) 2 days in which neither Compound A nor Compound B, or a pharmaceutically acceptable salt form thereof, is administered; followed by (b) 7 days in which neither Compound A nor Compound B, or a pharmaceutically acceptable salt form thereof, is administered.

E47. The method of any one of E1-E42, wherein Compound A and Compound B, or a pharmaceutically acceptable salt form thereof, are administered on a 28-day dosing cycle comprising (a) three 7-day periods each comprising (i) 4 days in which Compound A and Compound B, or a pharmaceutically acceptable salt form thereof, are both administered and (ii) 3 days in which neither Compound A nor Compound B, or a pharmaceutically acceptable salt form thereof are administered; and (b) 7 days in which neither Compound A nor Compound B, or a pharmaceutically acceptable salt form thereof, is administered.

E48. The method of any one of E1-E42, wherein Compound A and Compound B, or a pharmaceutically acceptable salt form thereof, are administered on a 28-day dosing cycle comprising (a) three 7-day periods each comprising (i) 4 days in which Compound A and Compound B, or a pharmaceutically acceptable salt form thereof, are both administered and (ii) 3 days in which neither Compound A nor Compound B, or a pharmaceutically acceptable salt form thereof, is administered; followed by (b) 7 days in which neither Compound A nor Compound B, or a pharmaceutically acceptable salt form thereof, is administered.

E49. The method of any one of E43-E48, wherein the 28-day dosing cycle is repeated up to a total of 24 consecutive 28-day dosing cycles.

E50. The method of any one of E43-E49, wherein only Compound B, or a pharmaceutically acceptable salt form thereof, is administered for a lead-in period prior to a first 28-day dosing cycle.

E51. The method of E50, wherein the amount of Compound B, or a pharmaceutically acceptable salt thereof, administered in the lead-in period is the same or lower than the amount of Compound B, or a pharmaceutically acceptable salt thereof, administered during the first 28-day dosing cycle.

E52. The method of E51, wherein the lead-in period begins 21 days before the first 28-day dosing cycle.

E53. The method of E52, wherein the lead-in period begins 14 days before the first 28-day dosing cycle.

E54. The method of E52, wherein the lead-in period begins 10 days before the first 28-day dosing cycle.

E55. The method of E52, wherein the lead-in period begins 7 days before the first 28-day dosing cycle.

E56. The method of any one of E50-E55, wherein the amount of Compound B, or a pharmaceutically acceptable salt thereof, administered in the lead-in period is about 5 mg to about 25 mg per day.

E57. The method of any one of E50-E55, wherein the amount of Compound B, or a pharmaceutically acceptable salt thereof, administered in the lead-in period is about 5 mg to about 20 mg per day.

E58. The method of any one of E50-E55, wherein the amount of Compound B, or a pharmaceutically acceptable salt thereof, administered in the lead-in period is about 5 mg to about 15 mg per day.

E59. The method of any one of E50-E55, wherein the amount of Compound B, or a pharmaceutically acceptable salt thereof, administered in the lead-in period is about 5 mg per day.

E60. The method of any one of E50-E55, wherein the amount of Compound B, or a pharmaceutically acceptable salt thereof, administered in the lead-in period is about 10 mg per day.

E61. The method of any one of E50-E55, wherein the amount of Compound B, or a pharmaceutically acceptable salt thereof, administered in the lead-in period is about 15 mg per day.

E62. The method of any one of E50-E55, wherein the amount of Compound B, or a pharmaceutically acceptable salt thereof, administered in the lead-in period is about 20 mg per day.

E63. The method of any one of E50-E55, wherein the Compound B administered in the lead-in period is a pharmaceutically acceptable salt form.

E64. The method of E63, wherein the pharmaceutically acceptable salt form is a maleate salt, which can be a sesqui-maleate salt.

E65. The method of E64, wherein the amount of Compound B as a maleate salt, which can be a sesqui-maleate salt, administered in the lead-in period is about 5 mg to about 40 mg per day.

E66. The method of E64, wherein the amount of Compound B as a maleate salt, which can be a sesqui-maleate salt, administered in the lead-in period is about 5 mg to about 30 mg per day.

E67. The method of E64, wherein the amount of Compound B as a maleate salt, which can be a sesqui-maleate salt, administered in the lead-in period is about 5 mg to about 25 mg per day.

E68. The method of E64, wherein the amount of Compound B as a maleate salt, which can be a sesqui-maleate salt, administered in the lead-in period is about 7 mg per day.

E69. The method of E64, wherein the amount of Compound B as a maleate salt, which can be a sesqui-maleate salt, administered in the lead-in period is about 13 mg per day.

E70. The method of E64, wherein the amount of Compound B as a maleate salt, which can be a sesqui-maleate salt, administered in the lead-in period is about 20 mg per day.

E71. The method of E64, wherein the amount of Compound B as a maleate salt, which can be a sesqui-maleate salt, administered in the lead-in period is about 27 mg per day.

E72. The method of any one of E50-E71, wherein the Compound B, or a pharmaceutically acceptable salt thereof, is administered daily during the lead-in period.

E73. The method of any one of E50-E72, wherein the Compound B, or a pharmaceutically acceptable salt thereof, is administered once daily during the lead-in period.

E74. The method of any one of E43-E49, wherein one or both of Compound A, or a pharmaceutically acceptable salt form thereof, and Compound B, or a pharmaceutically acceptable salt form thereof, is administered for a lead-in period prior to a first 28-day dosing cycle at a lower dose than the therapeutically effective amount of Compound A, or a pharmaceutically acceptable salt form thereof, and Compound B, or a pharmaceutically acceptable salt thereof, administered during the first 28-day cycle.

E75. The method of E74, wherein the amount of Compound A, or a pharmaceutically acceptable salt thereof, administered in the lead-in period is the same as the amount of Compound A, or a pharmaceutically acceptable salt thereof, administered during the first 28-day dosing cycle.

E76. The method of E74, wherein the amount of Compound A, or a pharmaceutically acceptable salt thereof, administered in the lead-in period is lower than the amount of Compound A, or a pharmaceutically acceptable salt thereof, administered during the first 28-day dosing cycle.

E77. The method of any one of E74-E76, wherein the amount of Compound A, or a pharmaceutically acceptable salt thereof, administered in the lead-in period is about 1 mg to about 5 mg per day.

E78. The method of any one of E74-E76, wherein the amount of Compound A, or a pharmaceutically acceptable salt thereof, administered in the lead-in period about 1 mg per day.

E79. The method of any one of E74-E76, wherein the amount of Compound A, or a pharmaceutically acceptable salt thereof, administered in the lead-in period about 2 mg per day.

E80. The method of any one of E74-E76, wherein the amount of Compound A, or a pharmaceutically acceptable salt thereof, administered in the lead-in period about 3 mg per day.

E81. The method of any one of E74-E80, wherein the amount of Compound B, or a pharmaceutically acceptable salt thereof, administered in the lead-in period is the same as the amount of Compound B, or a pharmaceutically acceptable salt thereof, administered during the first 28-day dosing cycle.

E82. The method of any one of E74-E80, wherein the amount of Compound B, or a pharmaceutically acceptable salt thereof, administered in the lead-in period is lower than the amount of Compound B, or a pharmaceutically acceptable salt thereof, administered during the first 28-day dosing cycle.

E83. The method of any one of E74-E80, wherein the amount of Compound B, or a pharmaceutically acceptable salt thereof, administered in the lead-in period is about 5 mg to about 25 mg per day.

E84. The method of any one of E74-E80, wherein the amount of Compound B, or a pharmaceutically acceptable salt thereof, administered in the lead-in period is about 5 mg to about 20 mg per day.

E85. The method of any one of E74-E80, wherein the amount of Compound B, or a pharmaceutically acceptable salt thereof, administered in the lead-in period is about 5 mg to about 15 mg per day.

E86. The method of any one of E74-E80, wherein the amount of Compound B, or a pharmaceutically acceptable salt thereof, administered in the lead-in period is about 5 mg per day.

E87. The method of any one of E74-E80, wherein the amount of Compound B, or a pharmaceutically acceptable salt thereof, administered in the lead-in period is about 10 mg per day.

E88. The method of any one of E74-E80, wherein the amount of Compound B, or a pharmaceutically acceptable salt thereof, administered in the lead-in period is about 15 mg per day.

E89. The method of any one of E74-E80, wherein the amount of Compound B, or a pharmaceutically acceptable salt thereof, administered in the lead-in period is about 20 mg per day.

E90. The method of any one of E74-E89, wherein the Compound B administered in the lead-in period is a pharmaceutically acceptable salt form.

E91. The method of E90, wherein the pharmaceutically acceptable salt form is a maleate salt, which can be a sesqui-maleate salt.

E92. The method of E91, wherein the amount of Compound B as a maleate salt, which can be a sesqui-maleate salt, administered in the lead-in period is about 5 mg to about 40 mg per day.

E93. The method of E91, wherein the amount of Compound B as a maleate salt, which can be a sesqui-maleate salt, administered in the lead-in period is about 5 mg to about 30 mg per day.

E94. The method of E91, wherein the amount of Compound B as a maleate salt, which can be a sesqui-maleate salt, administered in the lead-in period is about 5 mg to about 25 mg per day.

E95. The method of E91, wherein the amount of Compound B as a maleate salt, which can be a sesqui-maleate salt, administered in the lead-in period is about 7 mg per day.

E96. The method of E91, wherein the amount of Compound B as a maleate salt, which can be a sesqui-maleate salt, administered in the lead-in period is about 13 mg per day.

E97. The method of E91, wherein the amount of Compound B as a maleate salt, which can be a sesqui-maleate salt, administered in the lead-in period is about 20 mg per day.

E98. The method of E91, wherein the amount of Compound B as a maleate salt, which can be a sesqui-maleate salt, administered in the lead-in period is about 27 mg per day.

E99. The method of any one of E74-E98, wherein the lead-in period begins 21 days before the first 28-day dosing cycle.

E100. The method of any one of E74-E98, wherein the lead-in period begins 14 days before the first 28-day dosing cycle.

E101. The method of any one of E74-E98, wherein the lead-in period begins 10 days before the first 28-day dosing cycle.

E102. The method of any one of E74-E98, wherein the lead-in period begins 7 days before the first 28-day dosing cycle.

E103. The method of any one of E74-E102, wherein the Compound A, or a pharmaceutically acceptable salt thereof, and Compound B, or a pharmaceutically acceptable salt thereof, are each administered daily during the lead-in period.

E104. The method of any one of E74-E102, wherein the Compound A, or a pharmaceutically acceptable salt thereof, and Compound B, or a pharmaceutically acceptable salt thereof, are each administered once daily during the lead-in period.

E105. The method of any one of E74-E104, wherein Compound A, or a pharmaceutically acceptable salt thereof, and Compound B, or a pharmaceutically acceptable salt form thereof, are administered in the same or different dosage forms during the lead-in period.

E106. The method of E105, wherein Compound A, or a pharmaceutically acceptable salt thereof, and Compound B, or a pharmaceutically acceptable salt form thereof, are administered in the same dosage form during the lead-in period.

E107. The method of E106, wherein the dosage form is a capsule.

E108. The method of E105, wherein Compound A, or a pharmaceutically acceptable salt thereof, and Compound B, or a pharmaceutically acceptable salt form thereof, are administered in different dosage forms during the lead-in period.

E109. The method of E108, wherein Compound A is administered before, concomitantly, or subsequently to the administering of Compound B, or a pharmaceutically acceptable salt form thereof during the lead-in period.

E110. The method of E108 or E109, wherein the dosage form of Compound A, or a pharmaceutically acceptable salt thereof, is a capsule.

E111. The method of E108 or E109, wherein the dosage form of Compound B, or a pharmaceutically acceptable salt form thereof, is a capsule.

E112. The method of any one of E74-E111, wherein Compound A, or a pharmaceutically acceptable salt thereof, and Compound B, or a pharmaceutically acceptable salt form thereof, are administered orally during the lead-in period.

E113. The method of any one of E1-E112, wherein the patient has a confirmed mutation in RASA1 and/or RAF1.

E114. The method of E1, wherein the therapeutically effective amount of Compound A, or a pharmaceutically acceptable salt thereof, is about 1 mg per day and the therapeutically effective amount of Compound B, or a pharmaceutically acceptable salt form thereof, is about 20 mg per day.

E115. The method of E1, wherein the therapeutically effective amount of Compound A, or a pharmaceutically acceptable salt thereof, is about 2 mg per day and the therapeutically effective amount of Compound B, or a pharmaceutically acceptable salt form thereof, is about 15 mg per day, E116. The method of E1, wherein the therapeutically effective amount of Compound A, or a pharmaceutically acceptable salt thereof, is about 2 mg per day and the therapeutically effective amount of Compound B, or a pharmaceutically acceptable salt form thereof, is about 20 mg per day.

E117. The method of E1, wherein the therapeutically effective amount of Compound A, or a pharmaceutically acceptable salt thereof, is about 3 mg per day and the therapeutically effective amount of Compound B, or a pharmaceutically acceptable salt form thereof, is about 20 mg per day.

E118. The method of E1, wherein the therapeutically effective amount of Compound A, or a pharmaceutically acceptable salt thereof, is about 2 mg per day and the therapeutically effective amount of Compound B, or a pharmaceutically acceptable salt form thereof, is about 15 mg per day.

E119. The method of E1, wherein the therapeutically effective amount of Compound A, or a pharmaceutically acceptable salt thereof, is about 3 mg per day and the therapeutically effective amount of Compound B, or a pharmaceutically acceptable salt form thereof, is about 20 mg per day.

E120. The method of E1, wherein the therapeutically effective amount of Compound A, or a pharmaceutically acceptable salt thereof, is about 3 mg per day and the therapeutically effective amount of Compound B, or a pharmaceutically acceptable salt form thereof, is about 15 mg per day.

E121. The method of E1, wherein the therapeutically effective amount of Compound A, or a pharmaceutically acceptable salt thereof, is about 4 mg per day and the therapeutically effective amount of Compound B, or a pharmaceutically acceptable salt form thereof, is about 20 mg per day.

E122. The method of E1, wherein the therapeutically effective amount of Compound A, or a pharmaceutically acceptable salt thereof, is about 4 mg per day and the therapeutically effective amount of Compound B, or a pharmaceutically acceptable salt form thereof, is about 15 mg per day.

E123. The method of E1, wherein the therapeutically effective amount of Compound A, or a pharmaceutically acceptable salt thereof, is about 4 mg per day and the therapeutically effective amount of Compound B, or a pharmaceutically acceptable salt form thereof, is about 5 mg per day.

E124. The method of E1, wherein the therapeutically effective amount of Compound A, or a pharmaceutically acceptable salt thereof, is about 4 mg per day and the therapeutically effective amount of Compound B, or a pharmaceutically acceptable salt form thereof, is about 10 mg per day.

E125. The method of E1, wherein the therapeutically effective amount of Compound A, or a pharmaceutically acceptable salt thereof, is about 8 mg per day and the therapeutically effective amount of Compound B, or a pharmaceutically acceptable salt form thereof, is about 5 mg per day.

E126. The method of E1, wherein the therapeutically effective amount of Compound A, or a pharmaceutically acceptable salt thereof, is about 8 mg per day and the therapeutically effective amount of Compound B, or a pharmaceutically acceptable salt form thereof, is about 10 mg per day.

E127. The method of E1, wherein the therapeutically effective amount of Compound A, or a pharmaceutically acceptable salt thereof, is about 12 mg per day and the therapeutically effective amount of Compound B, or a pharmaceutically acceptable salt form thereof, is about 5 mg per day.

E128. The method of E1, wherein the therapeutically effective amount of Compound A, or a pharmaceutically acceptable salt thereof, is about 12 mg per day and the therapeutically effective amount of Compound B, or a pharmaceutically acceptable salt form thereof, is about 10 mg per day E129. The method of any one of E114-E128, wherein Compound B is a pharmaceutically acceptable salt form.

E130. The method of E129, wherein the pharmaceutically acceptable salt form is a maleate salt which can be a sesqui-maleate salt.

E131. The method of E130, wherein the therapeutically effective amount of Compound A, or a pharmaceutically acceptable salt thereof, is about 1 mg per day and the therapeutically effective amount of Compound B, as a maleate salt, which can be a sesqui-maleate salt, is about 27 mg per day.

E132. The method of E130, wherein the therapeutically effective amount of Compound A, or a pharmaceutically acceptable salt thereof, is about 2 mg per day and the therapeutically effective amount of Compound B, as a maleate salt, which can be a sesqui-maleate salt, is about 20 mg per day, E133. The method of E130, wherein the therapeutically effective amount of Compound A, or a pharmaceutically acceptable salt thereof, is about 2 mg per day and the therapeutically effective amount of Compound B, as a maleate salt, which can be a sesqui-maleate salt, is about 27 mg per day.

E134. The method of E130, wherein the therapeutically effective amount of Compound A, or a pharmaceutically acceptable salt thereof, is about 3 mg per day and the therapeutically effective amount of Compound B, as a maleate salt, which can be a sesqui-maleate salt, is about 27 mg per day.

E135. The method of E130, wherein the therapeutically effective amount of Compound A, or a pharmaceutically acceptable salt thereof, is about 2 mg per day and the therapeutically effective amount of Compound B, as a maleate salt, which can be a sesqui-maleate salt, is about 20 mg per day.

E136. The method of E130, wherein the therapeutically effective amount of Compound A, or a pharmaceutically acceptable salt thereof, is about 3 mg per day and the therapeutically effective amount of Compound B, as a maleate salt, which can be a sesqui-maleate salt, is about 27 mg per day.

E137. The method of E130, wherein the therapeutically effective amount of Compound A, or a pharmaceutically acceptable salt thereof, is about 3 mg per day and the therapeutically effective amount of Compound B, as a maleate salt, which can be a sesqui-maleate salt, is about 20 mg per day.

E138. The method of E130, wherein the therapeutically effective amount of Compound A, or a pharmaceutically acceptable salt thereof, is about 4 mg per day and the therapeutically effective amount of Compound B, as a maleate salt, which can be a sesqui-maleate salt, is about 27 mg per day.

E139. The method of E130, wherein the therapeutically effective amount of Compound A, or a pharmaceutically acceptable salt thereof, is about 4 mg per day and the therapeutically effective amount of Compound B, as a maleate salt, which can be a sesqui-maleate salt, is about 20 mg per day.

E140. The method of E130, wherein the therapeutically effective amount of Compound A, or a pharmaceutically acceptable salt thereof, is about 4 mg per day and the therapeutically effective amount of Compound B, as a maleate salt, which can be a sesqui-maleate salt, is about 7 mg per day.

E141. The method of E130, wherein the therapeutically effective amount of Compound A, or a pharmaceutically acceptable salt thereof, is about 4 mg per day and the therapeutically effective amount of Compound B, or a pharmaceutically acceptable salt form thereof, is about 13 mg per day.

E142. The method of E130, wherein the therapeutically effective amount of Compound A, or a pharmaceutically acceptable salt thereof, is about 8 mg per day and the therapeutically effective amount of Compound B, or a pharmaceutically acceptable salt form thereof, is about 7 mg per day.

E143. The method of E130, wherein the therapeutically effective amount of Compound A, or a pharmaceutically acceptable salt thereof, is about 8 mg per day and the therapeutically effective amount of Compound B, or a pharmaceutically acceptable salt form thereof, is about 13 mg per day.

E144. The method of E130, wherein the therapeutically effective amount of Compound A, or a pharmaceutically acceptable salt thereof, is about 12 mg per day and the therapeutically effective amount of Compound B, or a pharmaceutically acceptable salt form thereof, is about 7 mg per day.

E145. The method of E130, wherein the therapeutically effective amount of Compound A, or a pharmaceutically acceptable salt thereof, is about 12 mg per day and the therapeutically effective amount of Compound B, or a pharmaceutically acceptable salt form thereof, is about 13 mg per day.

E146. The method of any one of E114-E145, wherein Compound A, or a pharmaceutically acceptable salt thereof, and Compound B, or a pharmaceutically acceptable salt form thereof, are administered in the same or different dosage forms.

E147. The method of E146, wherein Compound A, or a pharmaceutically acceptable salt thereof, and Compound B, or a pharmaceutically acceptable salt form thereof, are administered in the same dosage form.

E148. The method of E147, wherein the dosage form is a capsule.

E149. The method of any one of E114-E148, wherein Compound A, or a pharmaceutically acceptable salt thereof, is administered once per day.

E150. The method of any one of E114-E149, wherein Compound B, or a pharmaceutically acceptable salt form thereof, is administered once per day.

E151. The method of E146, wherein Compound A, or a pharmaceutically acceptable salt thereof, and Compound B, or a pharmaceutically acceptable salt form thereof, are administered in different dosage forms.

E152. The method of E151, wherein Compound A is administered before, concomitantly, or subsequently to the administering of Compound B, or a pharmaceutically acceptable salt form thereof.

E153. The method of E151 or E152, wherein the dosage form of Compound A, or a pharmaceutically acceptable salt thereof, is a capsule.

E154. The method of E151 or E152, wherein the dosage form of Compound B, or a pharmaceutically acceptable salt form thereof, is a capsule.

E155. The method of any one of E114-E154, wherein Compound A, or a pharmaceutically acceptable salt thereof, and Compound B, or a pharmaceutically acceptable salt form thereof, are administered orally.

E156. The method of any one of E114-E155, wherein the solid tumor is selected from the group consisting of malignant peripheral nerve sheath tumor, biliary tract cancer, breast cancer, cholangiocarcinoma, urothelial cancer, uterine neoplasm, lung adenocarcinoma, squamous non-small cell lung cancer, non-squamous non-small cell lung cancer, gastric cancer, sarcoma, bladder cancer, head and neck cancer, small cell lung cancer, endometrial cancer, esophageal cancer, adenoid cystic carcinoma, gallbladder cancer, colorectal cancer, thyroid cancer, hepatocellular cancer, prostate cancer, oral cancer, cervical cancer, pancreatic carcinoma, ovarian cancer, melanoma, and serous carcinoma to the peritoneum.

E157. The method of E156, wherein the patient has non-small cell lung cancer.

E158. The method of E156, wherein the patient has endometrial cancer.

E159. The method of E156, wherein the patient has ovarian cancer.

E160. The method of E156, where the patient has low grade serous ovarian cancer.

E161. The method of any one of E114-E160, wherein the patient has a confirmed mutation in one or more of KRAS, NRAS, HRAS, BRAF, NF1, MEK1, and MEK2.

E162. The method of any one of E114-E161, wherein the patient has a confirmed mutation in RASA1 and/or RAF1.

E163. The method of any one of E114-162, wherein Compound A, or a pharmaceutically acceptable salt thereof, and Compound B, or a pharmaceutically acceptable salt form thereof, are administered on a 28-day dosing cycle comprising: (a) 21 days in which Compound A and Compound B, or a pharmaceutically acceptable salt form thereof, are both administered; and (b) 7 days in which neither Compound A nor Compound B, or a pharmaceutically acceptable salt form thereof, is administered.

E164. The method of any one of E114-E162, wherein Compound A, or a pharmaceutically acceptable salt thereof, and Compound B, or a pharmaceutically acceptable salt form thereof, are administered on a 28-day dosing cycle comprising (a) 21 days in which Compound A and Compound B, or a pharmaceutically acceptable salt form thereof are both administered; followed by (b) 7 days in which neither Compound A nor Compound B, or a pharmaceutically acceptable salt form thereof, is administered.

E165. The method of any one of E114-E162, wherein Compound A, or a pharmaceutically acceptable salt thereof, and Compound B, or a pharmaceutically acceptable salt form thereof, are administered on a 28-day dosing cycle comprising (a) three 7-day periods each comprising (i) 5 days in which Compound A and Compound B, or a pharmaceutically acceptable salt form thereof, are both administered and (ii) 2 days in which neither Compound A, or a pharmaceutically acceptable salt thereof, nor Compound B, or a pharmaceutically acceptable salt form thereof are administered; and (b) 7 days in which neither Compound A, or a pharmaceutically acceptable salt thereof, nor Compound B, or a pharmaceutically acceptable salt form thereof, is administered.

E166. The method of any one of E114-E162, wherein Compound A, or a pharmaceutically acceptable salt thereof, and Compound B, or a pharmaceutically acceptable salt form thereof, are administered on a 28-day dosing cycle comprising (a) three 7-day periods each comprising (i) 5 days in which Compound A, or a pharmaceutically acceptable salt thereof, and Compound B, or a pharmaceutically acceptable salt form thereof, are both administered and (ii) 2 days in which neither Compound A, or a pharmaceutically acceptable salt thereof, nor Compound B, or a pharmaceutically acceptable salt form thereof, is administered; followed by (b) 7 days in which neither Compound A, or a pharmaceutically acceptable salt thereof, nor Compound B, or a pharmaceutically acceptable salt form thereof, is administered.

E167. The method of any one of E114-E162, wherein Compound A, or a pharmaceutically acceptable salt thereof, and Compound B, or a pharmaceutically acceptable salt form thereof, are administered on a 28-day dosing cycle comprising (a) three 7-day periods each comprising (i) 4 days in which Compound A, or a pharmaceutically acceptable salt thereof, and Compound B, or a pharmaceutically acceptable salt form thereof, are both administered and (ii) 3 days in which neither Compound A, or a pharmaceutically acceptable salt thereof, nor Compound B, or a pharmaceutically acceptable salt form thereof are administered; and (b) 7 days in which neither Compound A, or a pharmaceutically acceptable salt thereof, nor Compound B, or a pharmaceutically acceptable salt form thereof, is administered.

E168. The method of any one of E114-E162, wherein Compound A, or a pharmaceutically acceptable salt thereof, and Compound B, or a pharmaceutically acceptable salt form thereof, are administered on a 28-day dosing cycle comprising (a) three 7-day periods each comprising (i) 4 days in which Compound A, or a pharmaceutically acceptable salt thereof, and Compound B, or a pharmaceutically acceptable salt form thereof, are both administered and (ii) 3 days in which neither Compound A nor Compound B, or a pharmaceutically acceptable salt form thereof, is administered; followed by (b) 7 days in which neither Compound A, or a pharmaceutically acceptable salt thereof, nor Compound B, or a pharmaceutically acceptable salt form thereof, is administered.

E169. The method of any one of E163-E168, wherein the 28-day dosing cycle is repeated up to a total of 24 consecutive 28-day dosing cycles.

E170. The method of any one of E163-E168, wherein only Compound B, or a pharmaceutically acceptable salt form thereof, is administered for a lead-in period prior to a first 28-day dosing cycle.

E171. The method of E170, wherein the amount of Compound B, or a pharmaceutically acceptable salt thereof, administered in the lead-in period is the same or lower than the amount of Compound B, or a pharmaceutically acceptable salt thereof, administered during the first 28-day dosing cycle.

E172. The method of E171, wherein the lead-in period begins 21 days before the first 28-day dosing cycle.

E173. The method of E171, wherein the lead-in period begins 14 days before the first 28-day dosing cycle.

E174. The method of E171, wherein the lead-in period begins 10 days before the first 28-day dosing cycle.

E175. The method of E171, wherein the lead-in period begins 7 days before the first 28-day dosing cycle.

E176. The method of any one of E163-E168, wherein the amount of Compound B, or a pharmaceutically acceptable salt thereof, administered in the lead-in period is about 5 mg to about 25 mg per day.

E177. The method of any one of E163-E168, wherein the amount of Compound B, or a pharmaceutically acceptable salt thereof, administered in the lead-in period is about 5 mg to about 20 mg per day.

E178. The method of any one of E163-E168, wherein the amount of Compound B, or a pharmaceutically acceptable salt thereof, administered in the lead-in period is about 5 mg to about 15 mg per day.

E179. The method of any one of E163-E168, wherein the amount of Compound B, or a pharmaceutically acceptable salt thereof, administered in the lead-in period is about 5 mg per day.

E180. The method of any one of E163-E168, wherein the amount of Compound B, or a pharmaceutically acceptable salt thereof, administered in the lead-in period is about 10 mg per day.

E181. The method of any one of E163-E168, wherein the amount of Compound B, or a pharmaceutically acceptable salt thereof, administered in the lead-in period is about 15 mg per day.

E182. The method of any one of E163-E168, wherein the amount of Compound B, or a pharmaceutically acceptable salt thereof, administered in the lead-in period is about 20 mg per day.

E183. The method of any one of E163-E168, wherein the Compound B administered in the lead-in period is a pharmaceutically acceptable salt form.

E184. The method of E183, wherein the pharmaceutically acceptable salt form is a maleate salt, which can be a sesqui-maleate salt.

E185. The method of E184, wherein the amount of Compound B as a maleate salt, which can be a sesqui-maleate salt, administered in the lead-in period is about 5 mg to about 40 mg per day.

E186. The method of E184, wherein the amount of Compound B as a maleate salt, which can be a sesqui-maleate salt, administered in the lead-in period is about 5 mg to about 30 mg per day.

E187. The method of E184, wherein the amount of Compound B as a maleate salt, which can be a sesqui-maleate salt, administered in the lead-in period is about 5 mg to about 25 mg per day.

E188. The method of E184, wherein the amount of Compound B as a maleate salt, which can be a sesqui-maleate salt, administered in the lead-in period is about 7 mg per day.

E189. The method of E184, wherein the amount of Compound B as a maleate salt, which can be a sesqui-maleate salt, administered in the lead-in period is about 13 mg per day.

E190. The method of E184, wherein the amount of Compound B as a maleate salt, which can be a sesqui-maleate salt, administered in the lead-in period is about 20 mg per day.

E191. The method of E184, wherein the amount of Compound B as a maleate salt, which can be a sesqui-maleate salt, administered in the lead-in period is about 27 mg per day.

E192. The method of any one of E170-E191, wherein the Compound B, or a pharmaceutically acceptable salt thereof, is administered daily during the lead-in period.

E193. The method of any one of E170-E192, wherein the Compound B, or a pharmaceutically acceptable salt thereof, is administered once daily during the lead-in period.

E194. The method of any one of E163-E168, wherein one or both of Compound A, or a pharmaceutically acceptable salt form thereof, and Compound B, or a pharmaceutically acceptable salt form thereof, is administered for a lead-in period prior to a first 28-day dosing cycle at a lower dose than the therapeutically effective amount of Compound A, or a pharmaceutically acceptable salt form thereof, and Compound B, or a pharmaceutically acceptable salt thereof, administered during the first 28-day cycle.

E195. The method of E194, wherein the amount of Compound A, or a pharmaceutically acceptable salt thereof, administered in the lead-in period is the same as the amount of Compound A, or a pharmaceutically acceptable salt thereof, administered during the first 28-day dosing cycle.

E196. The method of E194, wherein the amount of Compound A, or a pharmaceutically acceptable salt thereof, administered in the lead-in period is lower than the amount of Compound A, or a pharmaceutically acceptable salt thereof, administered during the first 28-day dosing cycle.

E197. The method of any one of E194-E196, wherein the amount of Compound A, or a pharmaceutically acceptable salt thereof, administered in the lead-in period is about 1 mg to about 5 mg per day.

E198. The method of any one of E194-E196, wherein the amount of Compound A, or a pharmaceutically acceptable salt thereof, administered in the lead-in period about 1 mg per day.

E199. The method of any one of E194-E196, wherein the amount of Compound A, or a pharmaceutically acceptable salt thereof, administered in the lead-in period about 2 mg per day.

E200. The method of any one of E194-E196, wherein the amount of Compound A, or a pharmaceutically acceptable salt thereof, administered in the lead-in period about 3 mg per day.

E201. The method of any one of E194-E200, wherein the amount of Compound B, or a pharmaceutically acceptable salt thereof, administered in the lead-in period is the same as the amount of Compound B, or a pharmaceutically acceptable salt thereof, administered during the first 28-day dosing cycle.

E202. The method of any one of E194-E200, wherein the amount of Compound B, or a pharmaceutically acceptable salt thereof, administered in the lead-in period is lower than the amount of Compound B, or a pharmaceutically acceptable salt thereof, administered during the first 28-day dosing cycle.

E203. The method of any one of E194-E202, wherein the amount of Compound B, or a pharmaceutically acceptable salt thereof, administered in the lead-in period is about 5 mg to about 25 mg per day.

E204. The method of any one of E194-E202, wherein the amount of Compound B, or a pharmaceutically acceptable salt thereof, administered in the lead-in period is about 5 mg to about 20 mg per day.

E205. The method of any one of E194-E202, wherein the amount of Compound B, or a pharmaceutically acceptable salt thereof, administered in the lead-in period is about 5 mg to about 15 mg per day.

E206. The method of any one of E194-E202, wherein the amount of Compound B, or a pharmaceutically acceptable salt thereof, administered in the lead-in period is about 5 mg per day.

E207. The method of any one of E194-E202, wherein the amount of Compound B, or a pharmaceutically acceptable salt thereof, administered in the lead-in period is about 10 mg per day.

E208. The method of any one of E194-E202, wherein the amount of Compound B, or a pharmaceutically acceptable salt thereof, administered in the lead-in period is about 15 mg per day.

E209. The method of any one of E194-E202, wherein the amount of Compound B, or a pharmaceutically acceptable salt thereof, administered in the lead-in period is about 20 mg per day.

E210. The method of any one of E194-E209, wherein the Compound B administered in the lead-in period is a pharmaceutically acceptable salt form.

E211. The method of E210, wherein the pharmaceutically acceptable salt form is a maleate salt, which can be a sesqui-maleate salt.

E212. The method of E211, wherein the amount of Compound B as a maleate salt, which can be a sesqui-maleate salt, administered in the lead-in period is about 5 mg to about 40 mg per day.

E213. The method of E211, wherein the amount of Compound B as a maleate salt, which can be a sesqui-maleate salt, administered in the lead-in period is about 5 mg to about 30 mg per day.

E214. The method of E211, wherein the amount of Compound B as a maleate salt, which can be a sesqui-maleate salt, administered in the lead-in period is about 5 mg to about 25 mg per day.

E215. The method of E211, wherein the amount of Compound B as a maleate salt, which can be a sesqui-maleate salt, administered in the lead-in period is about 7 mg per day.

E216. The method of E211, wherein the amount of Compound B as a maleate salt, which can be a sesqui-maleate salt, administered in the lead-in period is about 13 mg per day.

E217. The method of E211, wherein the amount of Compound B as a maleate salt, which can be a sesqui-maleate salt, administered in the lead-in period is about 20 mg per day.

E218. The method of E211, wherein the amount of Compound B as a maleate salt, which can be a sesqui-maleate salt, administered in the lead-in period is about 27 mg per day.

E219. The method of any one of E194-E218, wherein the lead-in period begins 21 days before the first 28-day dosing cycle.

E220. The method of any one of E194-E218, wherein the lead-in period begins 14 days before the first 28-day dosing cycle.

E221. The method of any one of E194-E218, wherein the lead-in period begins 10 days before the first 28-day dosing cycle.

E222. The method of any one of E194-E218, wherein the lead-in period begins 7 days before the first 28-day dosing cycle.

E223. The method of any one of E194-E222, wherein the Compound A, or a pharmaceutically acceptable salt thereof, and Compound B, or a pharmaceutically acceptable salt thereof, are each administered daily during the lead-in period.

E224. The method of any one of E194-E222, wherein the Compound A, or a pharmaceutically acceptable salt thereof, and Compound B, or a pharmaceutically acceptable salt thereof, are each administered once daily during the lead-in period.

E225. The method of any one of E194-222, wherein Compound A, or a pharmaceutically acceptable salt thereof, and Compound B, or a pharmaceutically acceptable salt form thereof, are administered in the same or different dosage forms during the lead-in period.

E226. The method of E225, wherein Compound A, or a pharmaceutically acceptable salt thereof, and Compound B, or a pharmaceutically acceptable salt form thereof, are administered in the same dosage form during the lead-in period.

E227. The method of E226, wherein the dosage form is a capsule.

E228. The method of E225, wherein Compound A, or a pharmaceutically acceptable salt thereof, and Compound B, or a pharmaceutically acceptable salt form thereof, are administered in different dosage forms during the lead-in period.

E229. The method of E228, wherein Compound A is administered before, concomitantly, or subsequently to the administering of Compound B, or a pharmaceutically acceptable salt form thereof during the lead-in period.

E230. The method of E228 or E229, wherein the dosage form of Compound A, or a pharmaceutically acceptable salt thereof, is a capsule.

E231. The method of E228 or E229, wherein the dosage form of Compound B, or a pharmaceutically acceptable salt form thereof, is a capsule.

E232. The method of any one of E194-E231, wherein Compound A, or a pharmaceutically acceptable salt thereof, and Compound B, or a pharmaceutically acceptable salt form thereof, are administered orally during the lead-in period.

E233. The method of any one of E1-E232, wherein Compound A is provided in a pharmaceutically acceptable salt form.

E234. The method of any one of E1-E232, wherein Compound A is provided in free base form.

E235. A method of treating a patient having a solid tumor comprising administering once daily 2 mg Compound A as free base and 15 mg Compound B, or a pharmaceutically acceptable salt thereof.

E236. The method of E235, wherein the Compound B is administered as a pharmaceutically acceptable salt form.

E237. The method of E236, wherein the pharmaceutically acceptable salt form is a maleate salt, which can be a sesqui-maleate salt.

E238. The method of E237, wherein the amount of Compound B as a maleate salt, which can be a sesqui-maleate salt, is about 20 mg.

E239. A method of treating a patient having a solid tumor comprising administering once daily 2 mg Compound A as free base and 20 mg Compound B, or a pharmaceutically acceptable salt thereof.

E240. The method of E239, wherein the Compound B is administered as a pharmaceutically acceptable salt form.

E241. The method of E240, wherein the pharmaceutically acceptable salt form is a maleate salt, which can be a sesqui-maleate salt.

E242. The method of E241, wherein the amount of Compound B as a maleate salt, which can be a sesqui-maleate salt, is about 27 mg.

E243. A method of treating a patient having a solid tumor comprising a 7 day cycle that comprises (a) administering once daily 3 mg of Compound A free base and 20 mg of Compound B, or a pharmaceutically acceptable salt form for 5 consecutive days; followed by (b) administering no Compound A or Compound B for 2 consecutive days.

E244. The method of E243, wherein the Compound B is administered as a pharmaceutically acceptable salt form.

E245. The method of E244, wherein the pharmaceutically acceptable salt form is a maleate salt, which can be a sesqui-maleate salt.

E246. The method of E245, wherein the amount of Compound B as a maleate salt, which can be a sesqui-maleate salt, is about 27 mg.

E247. A method of treating a patient having a solid tumor comprising:

(a) a lead-in period that comprises administering once daily 3 mg Compound A free base and 10 mg Compound B, or a pharmaceutically acceptable salt form thereof, for 14 consecutive days; followed by (b) a 7 day treatment cycle that comprises (i) administering once daily 3 mg of Compound A free base and 20 mg of Compound B, or a pharmaceutically acceptable salt form therefore, for 5 consecutive days; followed by (ii) administering no Compound A or Compound B for 2 consecutive days.

E248. The method of E247, wherein the Compound B is administered in both the lead-in period and treatment cycle as a pharmaceutically acceptable salt form.

E249. The method of E248, wherein the pharmaceutically acceptable salt form is a maleate salt, which can be a sesqui-maleate salt.

E250. The method of E249, wherein the amount of Compound B as a maleate salt, which can be a sesqui-maleate salt, administered in the lead-in period is about 13 mg.

E251. The method of E250, wherein the amount of Compound B as a maleate salt, which can be a sesqui-maleate salt, administered in the treatment period is about 27 mg.

E252. A method of treating a patient having a solid tumor comprising:

(a) a lead-in period that comprises administering a total of 2 mg Compound A free base divided over two doses per day and 15 mg Compound B, or a pharmaceutically acceptable salt form thereof, once daily for 14 consecutive days; followed by (b) a 7 day treatment cycle that comprises (i) administering 1 mg of Compound A free base twice daily and 15 mg of Compound B, or a pharmaceutically acceptable salt form therefore, once daily for 5 consecutive days; followed by (ii) administering no Compound A or Compound B for 2 consecutive days.

E253. The method of E252, wherein the Compound B is administered in both the lead-in period and treatment cycle as a pharmaceutically acceptable salt form.

E254. The method of E253, wherein the pharmaceutically acceptable salt form is a maleate salt, which can be a sesqui-maleate salt.

E255. The method of E254, wherein the amount of Compound B as a maleate salt, which can be a sesqui-maleate salt, administered in the lead-in period is about 13 mg.

E256. The method of E255, wherein the amount of Compound B as a maleate salt, which can be a sesqui-maleate salt, administered in the treatment period is about 20 mg.

E257. A method of treating a patient having a solid tumor comprising a 7 day cycle that comprises (a) administering once daily 4 mg of Compound A free base and 20 mg of Compound B, or a pharmaceutically acceptable salt form for 5 consecutive days; followed by (b) administering no Compound A or Compound B for 2 consecutive days.

E258. The method of E257, wherein the Compound B is administered as a pharmaceutically acceptable salt form.

E259. The method of E258, wherein the pharmaceutically acceptable salt form is a maleate salt, which can be a sesqui-maleate salt.

E260. The method of E259, wherein the amount of Compound B as a maleate salt, which can be a sesqui-maleate salt, is about 27 mg.

E261. A method of treating a patient having a solid tumor comprising:

(a) a lead-in period that comprises administering 15 mg Compound B, or a pharmaceutically acceptable salt form thereof, once daily for 14 consecutive days; followed by (b) a 7 day treatment cycle that comprises (i) administering once daily 1 mg of Compound A free base and 20 mg of Compound B, or a pharmaceutically acceptable salt form therefore, once daily for 5 consecutive days; followed by (ii) administering no Compound A or Compound B for 2 consecutive days.

E262. The method of E261, wherein the Compound B is administered in both the lead-in period and treatment cycle as a pharmaceutically acceptable salt form.

E263. The method of E262, wherein the pharmaceutically acceptable salt form is a maleate salt, which can be a sesqui-maleate salt.

E264. The method of E263, wherein the amount of Compound B as a maleate salt, which can be a sesqui-maleate salt, administered in the lead-in period is about 20 mg.

E265. The method of E264, wherein the amount of Compound B as a maleate salt, which can be a sesqui-maleate salt, administered in the treatment period is about 27 mg.

E266. A method of treating a patient having a solid tumor comprising:

(a) a lead-in period that comprises administering 15 mg Compound B, or a pharmaceutically acceptable salt form thereof, once daily for 14 consecutive days; followed by (b) a 7 day treatment cycle that comprises (i) administering once daily 2 mg of Compound A free base and 20 mg of Compound B, or a pharmaceutically acceptable salt form therefore, once daily for 5 consecutive days; followed by (ii) administering no Compound A or Compound B for 2 consecutive days.

E267. The method of E266, wherein the Compound B is administered in both the lead-in period and treatment cycle as a pharmaceutically acceptable salt form.

E268. The method of E267, wherein the pharmaceutically acceptable salt form is a maleate salt, which can be a sesqui-maleate salt.

E269. The method of E268, wherein the amount of Compound B as a maleate salt, which can be a sesqui-maleate salt, administered in the lead-in period is about 20 mg.

E270. The method of E269, wherein the amount of Compound B as a maleate salt, which can be a sesqui-maleate salt, administered in the treatment period is about 27 mg.

E271. A method of treating a patient having a solid tumor comprising:

(a) a lead-in period that comprises administering 15 mg Compound B, or a pharmaceutically acceptable salt form thereof, once daily for 14 consecutive days; followed by (b) a 7 day treatment cycle that comprises (i) administering once daily 3 mg of Compound A free base and 20 mg of Compound B, or a pharmaceutically acceptable salt form therefore, once daily for 5 consecutive days; followed by (ii) administering no Compound A or Compound B for 2 consecutive days.

E272. The method of E271, wherein the Compound B is administered in both the lead-in period and treatment cycle as a pharmaceutically acceptable salt form.

E273. The method of E272, wherein the pharmaceutically acceptable salt form is a maleate salt, which can be a sesqui-maleate salt.

E274. The method of E273, wherein the amount of Compound B as a maleate salt, which can be a sesqui-maleate salt, administered in the lead-in period is about 20 mg.

E275. The method of E274, wherein the amount of Compound B as a maleate salt, which can be a sesqui-maleate salt, administered in the treatment period is about 27 mg.

E276. A method of treating a patient having a solid tumor comprising:

(a) a lead-in period that comprises administering 15 mg Compound B, or a pharmaceutically acceptable salt form thereof, once daily for 14 consecutive days; followed by (b) a 7 day treatment cycle that comprises (i) administering once daily 4 mg of Compound A free base and 20 mg of Compound B, or a pharmaceutically acceptable salt form therefore, once daily for 5 consecutive days; followed by (ii) administering no Compound A or Compound B for 2 consecutive days.

E277. The method of E276, wherein the Compound B is administered in both the lead-in period and treatment cycle as a pharmaceutically acceptable salt form.

E278. The method of E277, wherein the pharmaceutically acceptable salt form is a maleate salt, which can be a sesqui-maleate salt.

E279. The method of E278, wherein the amount of Compound B as a maleate salt, which can be a sesqui-maleate salt, administered in the lead-in period is about 20 mg.

E280. The method of E279, wherein the amount of Compound B as a maleate salt, which can be a sesqui-maleate salt, administered in the treatment period is about 27 mg.

E281. A method of treating a patient having a solid tumor comprising:

(a) a lead-in period that comprises administering a total of 3 mg Compound A free base divided over two doses per day and 15 mg Compound B, or a pharmaceutically acceptable salt form thereof, once daily, for 14 consecutive days; followed by (b) a 7 day treatment cycle that comprises (i) administering once daily 3 mg of Compound A free base and 15 mg of Compound B, or a pharmaceutically acceptable salt form therefore, for 5 consecutive days; followed by (ii) administering no Compound A or Compound B for 2 consecutive days.

E282. The method of E281, wherein the Compound B is administered in both the lead-in period and treatment cycle as a pharmaceutically acceptable salt form.

E283. The method of E282, wherein the pharmaceutically acceptable salt form is a maleate salt, which can be a sesqui-maleate salt.

E284. The method of E283, wherein the amount of Compound B as a maleate salt, which can be a sesqui-maleate salt, administered in the lead-in period is about 13 mg.

E285. The method of E284, wherein the amount of Compound B as a maleate salt, which can be a sesqui-maleate salt, administered in the treatment period is about 20 mg.

E286. A method of treating a patient having a solid tumor comprising:

(a) a lead-in period that comprises administering a total of 4 mg Compound A free base divided over two doses per day and 15 mg Compound B, or a pharmaceutically acceptable salt form thereof, once daily for 14 consecutive days; followed by (b) a 7 day treatment cycle that comprises (i) administering once daily 4 mg of Compound A free base and 15 mg of Compound B, or a pharmaceutically acceptable salt form therefore, once daily for 5 consecutive days; followed by (ii) administering no Compound A or Compound B for 2 consecutive days.

E287. The method of E286, wherein the Compound B is administered in both the lead-in period and treatment cycle as a pharmaceutically acceptable salt form.

E288. The method of E287, wherein the pharmaceutically acceptable salt form is a maleate salt, which can be a sesqui-maleate salt.

E289. The method of E288, wherein the amount of Compound B as a maleate salt, which can be a sesqui-maleate salt, administered in the lead-in period is about 13 mg.

E290. The method of E289, wherein the amount of Compound B as a maleate salt, which can be a sesqui-maleate salt, administered in the treatment period is about 20 mg.

E291. A method of treating a patient having a solid tumor comprising administering twice daily 2 mg Compound A as free base and once daily 5 mg Compound B, or a pharmaceutically acceptable salt thereof.

E292. A method of treating a patient having a solid tumor comprising administering twice daily 4 mg Compound A as free base and once daily 5 mg Compound B, or a pharmaceutically acceptable salt thereof.

E293. A method of treating a patient having a solid tumor comprising administering twice daily 6 mg Compound A as free base and once daily 5 mg Compound B, or a pharmaceutically acceptable salt thereof.

E294. A method of treating a patient having a solid tumor comprising administering twice daily 2 mg Compound A as free base and twice daily 5 mg Compound B, or a pharmaceutically acceptable salt thereof.

E295. A method of treating a patient having a solid tumor comprising administering twice daily 4 mg Compound A as free base and twice daily 5 mg Compound B, or a pharmaceutically acceptable salt thereof.

E296. A method of treating a patient having a solid tumor comprising administering twice daily 6 mg Compound A as free base and twice daily 5 mg Compound B, or a pharmaceutically acceptable salt thereof.

E297. The method of any one of E292-E296, wherein Compound B is a pharmaceutically acceptable salt form.

E298. The method of E297, wherein the pharmaceutically acceptable salt form is a maleate salt which can be a sesqui-maleate salt.

E299. The method of E297, wherein each dose of Compound B, as a maleate salt, which can be a sesqui-maleate salt, is about 7 mg.

E300. The method of any one of E235-E299, wherein Compound A and Compound B, or a pharmaceutically acceptable salt form thereof, in the lead-in period and/or treatment period are administered in the same or different dosage forms.

E301. The method of E301, wherein Compound A and Compound B, or a pharmaceutically acceptable salt form thereof, in the lead-in period and/or treatment period are administered in the same dosage form.

E302. The method of E302, wherein the dosage form is a capsule.

E303. The method of any one of E235-E300, wherein Compound A and Compound B, or a pharmaceutically acceptable salt form thereof, in the lead-in period and/or treatment period are administered in different dosage forms.

E304. The method of E303, wherein Compound A is administered before, concomitantly, or subsequently to the administering of Compound B, or a pharmaceutically acceptable salt form thereof.

E305. The method of E303 or E304, wherein the dosage form of Compound A is a capsule.

E306. The method of any one of E303-E305, wherein the dosage form of Compound B, or a pharmaceutically acceptable salt form thereof, is a capsule.

E307. The method of any one of E235-E306, wherein Compound A and Compound B, or a pharmaceutically acceptable salt form thereof, are administered orally.

E308. The method of any one of E235-E307, wherein the solid tumor is selected from the group consisting of malignant peripheral nerve sheath tumor, biliary tract cancer, breast cancer, cholangiocarcinoma, urothelial cancer, uterine neoplasm, lung adenocarcinoma, squamous non-small cell lung cancer, non-squamous non-small cell lung cancer, gastric cancer, sarcoma, bladder cancer, head and neck cancer, small cell lung cancer, endometrial cancer, esophageal cancer, adenoid cystic carcinoma, gallbladder cancer, colorectal cancer, thyroid cancer, hepatocellular cancer, prostate cancer, oral cancer, cervical cancer, pancreatic carcinoma, ovarian cancer, melanoma, and serous carcinoma to the peritoneum.

E309. The method of E308, wherein the patient has non-small cell lung cancer.

E310. The method of E308, wherein the patient has endometrial cancer.

E311. The method of E308, wherein the patient has ovarian cancer.

E312. The method of E311, where the patient has low grade serous ovarian cancer.

E313. The method of any one of E235-E312, wherein the patient has a confirmed mutation in one or more of KRAS, NRAS, HRAS, BRAF, NF1, MEK1, and MEK2.

E314. The method of any one of E235-E313, wherein the patient has a confirmed mutation in RASA1 and/or RAF1.

E315. A pharmaceutical composition comprising:

a. Compound A;
b. Compound B, or a pharmaceutically acceptable salt form thereof
c. a filler;
d. a disintegrant; and
e. a lubricant.

E316. The pharmaceutical composition of E315, wherein Compound A is present at about 0.8 mg to about 1.2 mg.

E317. The pharmaceutical composition of E315, wherein Compound A is present at about 1.5 mg to about 2.5 mg.

E318. The pharmaceutical composition of any one of E315-E317, wherein the pharmaceutically acceptable salt of Compound B is the maleic acid salt, which can be a sesqui-maleate salt, of Compound B and is present at about 6 mg to about 8 mg.

E319. The pharmaceutical composition of any one of E315-E317, wherein the pharmaceutically acceptable salt of Compound B is the maleic acid salt, which can be a sesqui-maleate salt, of Compound B and is present at about 20 mg to about 35 mg.

E320. The pharmaceutical composition of any one of E315-E319, wherein the filler is present at about 80 wt/wt % to about 90 wt/wt %.

E321. The pharmaceutical composition of any one of E315-E319, wherein the filler is present at about 72.5 wt/wt % to about 85 wt/wt %.

E322. The pharmaceutical composition of any one of E315-E321, wherein the disintegrant is present at about 3.5 wt/wt % to about 4.5 wt/wt %.

E323. The pharmaceutical composition of any one of E315-E322, wherein the lubricant is present at about 1.5 wt/wt % to about 5.0 wt/wt %.

E324. The pharmaceutical composition of any one of E315-E323, wherein the filler is selected from the group consisting of microcrystalline cellulose, lactose, mannitol, starch, dibasic calcium phosphate, and combinations thereof.

E325. The pharmaceutical composition of E324, wherein the filler comprises microcrystalline cellulose.

E326. The pharmaceutical composition of E325, wherein the microcrystalline cellulose is silicified microcrystalline cellulose.

E327. The pharmaceutical composition of any one of E315-E326, wherein the disintegrant is selected from the group consisting of croscarmellose, sodium starch glycolate, crospovidone, alginic acid, and combinations thereof.

E328. The pharmaceutical composition of E327, wherein the disintegrant comprises croscarmellose sodium.

E329. The pharmaceutical composition of any one of E315-E328, wherein the lubricant is selected from the group consisting of sodium stearyl fumarate, magnesium stearate, glyceryl dibehenate, talc, or combinations thereof.

E330. The pharmaceutical composition of E329, wherein the lubricant comprises sodium stearyl fumarate.

E331. The pharmaceutical composition of E329, wherein the lubricant comprises magnesium stearate.

E332. The pharmaceutical composition of any one of E315-E331, wherein the pharmaceutically acceptable salt of Compound B is the maleic acid salt of Compound B, which can be a sesqui-maleate salt.

E333. The pharmaceutical composition of any one of E315-E332, wherein the pharmaceutical composition is a tablet or capsule.

E334. The pharmaceutical composition of E333, wherein the pharmaceutical composition is a capsule.

E335. The pharmaceutical composition of E334, wherein the capsule comprises about 1.0 mg of Compound A and about 7 mg of the maleic acid salt of Compound B, which can be a sesqui-maleate salt, wherein each component of the capsule is as follows:

a. about 0.8 wt/wt % to about 1.2 wt/wt % of Compound A;
b. about 6 wt/wt % to about 8 wt/wt % of the maleic acid salt of Compound B, which can be a sesqui-maleate salt;
c. about 80 wt/wt % to about 90 wt/wt % of silicified microcrystalline cellulose;
d. about 3.5 wt/wt % to about 4.5 wt/wt % of croscarmellose sodium;
e. about 1.5 wt/wt % to about 5.0 wt/wt % of sodium stearyl fumarate; and
f. a gelatin capsule which encapsulates components a-e.

E336. The pharmaceutical composition of E334, wherein the capsule comprises about 2.0 mg of Compound A and about 27 mg of the maleic acid salt, which can be a sesqui-maleate salt, of Compound B, wherein each component of the capsule is as follows:

a. about 0.8 wt/wt % to about 1.3 wt/wt % of Compound A;
b. about 12.3 wt/wt % to about 15.0 wt/wt % of the maleic acid salt of Compound B, which can be a sesqui-maleate salt;
c. about 72.5 wt/wt % to about 85 wt/wt % of silicified microcrystalline cellulose;
d. about 3.5 wt/wt % to about 4.5 wt/wt % of croscarmellose sodium;
e. about 1.5 wt/wt % to about 5.0 wt/wt % of sodium stearyl fumarate; and
f. a gelatin capsule which encapsulates components a-e.

E337. A method of treating a patient having a solid tumor comprising administering to the patient in need thereof, a pharmaceutical composition of any one of E315-E336.

E338. The method of E337, wherein the solid tumor is selected from the group consisting of malignant peripheral nerve sheath tumor, biliary tract cancer, breast cancer, cholangiocarcinoma, urothelial cancer, uterine neoplasm, lung adenocarcinoma, squamous non-small cell lung cancer, non-squamous non-small cell lung cancer, gastric cancer, sarcoma, bladder cancer, head and neck cancer, small cell lung cancer, endometrial cancer, esophageal cancer, adenoid cystic carcinoma, gallbladder cancer, colorectal cancer, thyroid cancer, hepatocellular cancer, prostate cancer, oral cancer, cervical cancer, pancreatic carcinoma, ovarian cancer, melanoma, and serous carcinoma to the peritoneum.

E339. The method of E338, wherein the patient has non-small cell lung cancer.

E340. The method of E338, wherein the patient has endometrial cancer.

E341. The method of E338, wherein the patient has ovarian cancer.

E342. The method of E341, where the patient has low grade serous ovarian cancer.

E343. The method of any one of E338-E342, wherein the patient has a confirmed mutation in one or more of KRAS, NRAS, HRAS, BRAF, NF1, MEK1, and MEK2.

E344. The method of any one of E338-E343, wherein the pharmaceutical composition of any one of E315-E335 is administered on a 28-day dosing cycle comprising: (a) 21 days in which the pharmaceutical composition comprising Compound A and Compound B, or a pharmaceutically acceptable salt form thereof form, is administered; and (b) 7 days in which the pharmaceutical composition comprising Compound A and Compound B, or a pharmaceutically acceptable salt form thereof, is not administered.

E345. The method of any one of E338-E343, wherein the pharmaceutical composition of any one of E315-E335 is administered on a 28-day dosing cycle comprising (a) 21 days in which the pharmaceutical composition comprising Compound A and Compound B, or a pharmaceutically acceptable salt form thereof, is administered; followed by (b) 7 days in which the pharmaceutical composition comprising Compound A and Compound B, or a pharmaceutically acceptable salt form thereof, is not administered.

E346. The method of any one of E338-E343, wherein the pharmaceutical composition of any one of E315-E335 is administered on a 28-day dosing cycle comprising (a) three 7-day periods each comprising (i) 5 days in which the pharmaceutical composition comprising Compound A and Compound B, or a pharmaceutically acceptable salt form thereof, is administered and (ii) 2 days in which the pharmaceutical composition comprising Compound A and Compound B, or a pharmaceutically acceptable salt form thereof, is not administered; and (b) 7 days in which the pharmaceutical composition comprising Compound A and Compound B, or a pharmaceutically acceptable salt form thereof, is not administered.

E347. The method of any one of E338-E344, wherein the pharmaceutical composition of any one of E315-E335 is administered on a 28-day dosing cycle comprising (a) three 7-day periods each comprising (i) 5 days in which the pharmaceutical composition comprising Compound A and Compound B, or a pharmaceutically acceptable salt form thereof, is administered and (ii) 2 days in which the pharmaceutical composition comprising Compound A and Compound B, or a pharmaceutically acceptable salt form thereof, is not administered; followed by (b) 7 days in which the pharmaceutical composition comprising Compound A and Compound B, or a pharmaceutically acceptable salt form thereof, is not administered.

E348. The method of any one of E338-E343, wherein the pharmaceutical composition of any one of E315-E335 is administered on a 28-day dosing cycle comprising (a) three 7-day periods each comprising (i) 4 days in which the pharmaceutical composition comprising Compound A and Compound B, or a pharmaceutically acceptable salt form thereof, is administered and (ii) 3 days in which the pharmaceutical composition comprising Compound A and Compound B, or a pharmaceutically acceptable salt form thereof, is administered; and (b) 7 days in which the pharmaceutical composition comprising Compound A and Compound B, or a pharmaceutically acceptable salt form thereof, is not administered.

E349. The method of any one of E338-E343, wherein the pharmaceutical composition of any one of E315-E335 is administered on a 28-day dosing cycle comprising (a) three 7-day periods each comprising (i) 4 days in which the pharmaceutical composition comprising Compound A and Compound B, or a pharmaceutically acceptable salt form thereof, is administered and (ii) 3 days in which the pharmaceutical composition comprising Compound A and Compound B, or a pharmaceutically acceptable salt form thereof, is not administered; followed by (b) 7 days in which the pharmaceutical composition comprising Compound A and Compound B, or a pharmaceutically acceptable salt form thereof, is not administered.

E350. The method of any one of E334-E349, wherein the 28-day dosing cycle is repeated up to a total of 24 consecutive 28-day dosing cycles.

E351. The method of any one of E338-E343, wherein the pharmaceutical composition of any one of E315-E335 is administered on a 7-day dosing cycle comprising (a) 5 days in which the pharmaceutical composition comprising Compound A and Compound B, or a pharmaceutically acceptable salt form thereof, is administered; followed by (b) 2 days in which the pharmaceutical composition comprising Compound A and Compound B, or a pharmaceutically acceptable salt form thereof, is not administered.

E352. The method of any one of E338-E351, wherein the patient has a confirmed mutation in RASA1 and/or RAF1.

E353. Use of a combination of Compound A, or a pharmaceutically acceptable salt form thereof, and Compound B, or a pharmaceutically acceptable salt form thereof, for the manufacture of a medicament for treating a patient having a solid tumor.

E354. The use of E353, wherein Compound A and Compound B, or a pharmaceutically acceptable salt form thereof, are in the same or different dosage forms.

E355. The use of E354, wherein Compound A and Compound B, or a pharmaceutically acceptable salt form thereof, are in the same dosage form.

E356. The use of E355, wherein the dosage form is the pharmaceutical composition of any one of E315-E350.

E357. The use of E354, wherein Compound A and Compound B, or a pharmaceutically acceptable salt form thereof, are administered in different dosage forms.

E358. The use of E357, wherein Compound A is administered before, concomitantly, or subsequently to the administering of Compound B, or a pharmaceutically acceptable salt form thereof.

E359. The use of E357 or E358, wherein the dosage form of Compound A is a capsule.

E360. The use of any one of E357-E359, wherein the dosage form of Compound B, or a pharmaceutically acceptable salt form thereof, is a capsule.

E361. The use of any one of E357-E359, wherein the pharmaceutically acceptable salt of Compound B is the maleic acid salt of Compound B.

E362. The use of any one of E357-E360, wherein Compound A and Compound B, or a pharmaceutically acceptable salt form thereof, are administered orally.

E363. The use of any one of E353-E360, wherein the solid tumor is selected from the group consisting of malignant peripheral nerve sheath tumor, biliary tract cancer, breast cancer, cholangiocarcinoma, urothelial cancer, uterine neoplasm, lung adenocarcinoma, squamous non-small cell lung cancer, non-squamous non-small cell lung cancer, gastric cancer, sarcoma, bladder cancer, head and neck cancer, small cell lung cancer, endometrial cancer, esophageal cancer, adenoid cystic carcinoma, gallbladder cancer, colorectal cancer, thyroid cancer, hepatocellular cancer, prostate cancer, oral cancer, cervical cancer, pancreatic carcinoma, ovarian cancer, melanoma, and serous carcinoma to the peritoneum.

E364. The use of E363, wherein the patient has non-small cell lung cancer.

E365. The use of E363, wherein the patient has endometrial cancer.

E366. The use of E363, wherein the patient has ovarian cancer.

E367. The use of E366, where the patient has low grade serous ovarian cancer.

E368. The use of any one of E353-E367, wherein the patient has a confirmed mutation in one or more of KRAS, NRAS, HRAS, BRAF, NF1, MEK1, and MEK2.

E369. The use of any one of E353-E367, wherein the patient has a confirmed mutation in RASA1 and/or RAF1.

LIST OF REFERENCES

Chapman P B, Hauschild A, Robert C, et al. Improved survival with vemurafenib in melanoma with BRAF V600E mutation. N Engl J Med. 2011; 364(26):2507-16.

Hauschild A, Grob J J, Demidov L V, et al. Dabrafenib in BRAF-mutated metastatic melanoma: a multicentre, open-label, phase 3 randomised controlled trial. Lancet. 2012; 380(9839):358-65.

Kwong, Lawrence N., et al. “Co-clinical assessment identifies patterns of BRAF inhibitor resistance in melanoma.” The Journal of clinical investigation 125.4 (2015): 1459-1470.

Larkin, James, et al. “Combined vemurafenib and cobimetinib in BRAF-mutated melanoma.” New England Journal of Medicine 371.20 (2014): 1867-1876.

Long, Georgina V., et al. “Dabrafenib and trametinib versus dabrafenib and placebo for Val600 BRAF-mutant melanoma: a multicentre, double-blind, phase 3 randomised controlled trial.” The Lancet 386.9992 (2015): 444-451.

Flaherty, Keith T., et al. “Combined BRAF and MEK inhibition in melanoma with BRAF V600 mutations.” New England Journal of Medicine 367.18 (2012): 1694-1703

Flaherty K T, Robert C, Hersey P, et al. Improved survival with MEK inhibition in BRAF-mutated melanoma. N Engl J Med. 2012; 367(2):107-14.

Reddy, Sangeetha M., Alexandre Reuben, and Jennifer A. Wargo. “Influences of BRAF inhibitors on the immune microenvironment and the rationale for combined molecular and immune targeted therapy.” Current oncology reports 18.7 (2016): 42

Rizos, Helen, et al. “BRAF inhibitor resistance mechanisms in metastatic melanoma: spectrum and clinical impact.” Clinical cancer research 20.7 (2014): 1965-1977

What is claimed:

1. A method of treating a patient having a solid tumor comprising co-administering to the patient a therapeutically effective amount of mirdametinib or a pharmaceutically acceptable salt thereof, and a therapeutically effective amount of lifirafenib, or a pharmaceutically acceptable salt thereof.

2. The method of claim 1, wherein the therapeutically effective amount of mirdametinib is about 1 mg to about 5 mg per day.

3. The method of claim 1, wherein the therapeutically effective amount of lifirafenib, or a pharmaceutically acceptable salt thereof, is about 5mg to about 40 mg per day.

4. The method of claim 1, wherein mirdametinib is administered once per day.

5. The method of claim 1, wherein lifirafenib, or a pharmaceutically acceptable salt thereof, is administered once per day.

6. The method of claim 1, wherein the solid tumor is selected from the group consisting of malignant peripheral nerve sheath tumor, biliary tract cancer, breast cancer, cholangiocarcinoma, urothelial cancer, uterine neoplasm, lung adenocarcinoma, squamous non-small cell lung cancer, non-squamous non-small cell lung cancer, gastric cancer, sarcoma, bladder cancer, head and neck cancer, small cell lung cancer, endometrial cancer, esophageal cancer, adenoid cystic carcinoma, gallbladder cancer, colorectal cancer, thyroid cancer, hepatocellular cancer, prostate cancer, oral cancer, cervical cancer, pancreatic carcinoma, ovarian cancer, melanoma, and serous carcinoma to the peritoneum.

7. The method of claim 6, wherein the patient has non-small cell lung cancer.

8. The method of claim 6, wherein the patient has endometrial cancer.

9. The method of claim 6, wherein the patient has ovarian cancer.

10. The method of claim 9, where the patient has low grade serous ovarian cancer.

11. A pharmaceutical composition comprising:

a) mirdametinib, or a pharmaceutically acceptable salt thereof;

b) lifirafenib, or a pharmaceutically acceptable salt thereof;

c) optionally a filler;

d) optionally a disintegrant; and e) optionally a lubricant.

12. The pharmaceutical composition of claim 11, wherein mirdametinib is present at about 0.8 mg to about 1.2 mg.

13. The pharmaceutical composition of claim 11, wherein mirdametinib is present at about 1.5 mg to about 2.5 mg.

14. The pharmaceutical composition of claim 11, comprising a filler, a disintegrant, and a lubricant.

15. The pharmaceutical composition of claim 14, wherein mirdametinib is present at about 0.8 mg to about 1.2 mg.

16. The pharmaceutical composition of claim 14, wherein mirdametinib is present at about 1.5 mg to about 2.5 mg.

* * * * *